US008324258B2

(12) United States Patent
Glick et al.

(10) Patent No.: US 8,324,258 B2
(45) Date of Patent: Dec. 4, 2012

(54) F₁F₀-ATPASE INHIBITORS AND RELATED METHODS

(75) Inventors: Gary D. Glick, Ann Arbor, MI (US); Gina Ney, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/677,598

(22) PCT Filed: Sep. 11, 2008

(86) PCT No.: PCT/US2008/076021
§ 371 (c)(1),
(2), (4) Date: May 10, 2010

(87) PCT Pub. No.: WO2009/036175
PCT Pub. Date: Mar. 19, 2009

(65) Prior Publication Data
US 2010/0222400 A1  Sep. 2, 2010

Related U.S. Application Data

(60) Provisional application No. 60/972,553, filed on Sep. 14, 2007.

(51) Int. Cl.
*A61K 31/41* (2006.01)
*A61K 31/405* (2006.01)
*C07D 207/00* (2006.01)
*C07D 209/00* (2006.01)
*C07D 257/04* (2006.01)

(52) U.S. Cl. ........ 514/383; 514/403; 514/408; 514/415; 548/262.2; 548/356.1; 548/400; 548/452

(58) Field of Classification Search .................. 514/383, 514/403, 408, 415; 548/262.2, 356.1, 400, 548/452
See application file for complete search history.

(56) References Cited

U.S. PATENT DOCUMENTS

| 3,261,828 A | 7/1966 | Uskokovic |
| 3,374,264 A | 3/1968 | Uskokovic |
| 3,384,635 A | 5/1968 | Calabateas |
| 3,415,814 A | 12/1968 | Calabateas |
| 3,847,905 A | 11/1974 | Bub |
| 4,076,823 A | 2/1978 | Wade |
| 4,088,756 A | 5/1978 | Voorhees |
| 4,108,852 A | 8/1978 | Bub |
| 4,110,337 A | 8/1978 | Szarvasi |
| RE30,293 E | 6/1980 | Bub |
| 4,495,101 A | 1/1985 | Klaubert |
| 4,551,480 A | 11/1985 | Stiefel |
| 4,560,684 A | 12/1985 | Sugasawa |
| 4,623,646 A | 11/1986 | Casals-Stenzel |
| 4,751,223 A | 6/1988 | Glamkowski |
| 4,820,834 A | 4/1989 | Evans |
| 4,894,366 A | 1/1990 | Okuhara |
| 4,898,861 A | 2/1990 | Morgan |
| 4,916,138 A | 4/1990 | Ueda |
| 4,929,611 A | 5/1990 | Okuhara |
| 4,946,778 A | 8/1990 | Ladner |
| 5,004,741 A | 4/1991 | Evans |
| 5,041,438 A | 8/1991 | Hsu |
| 5,141,930 A | 8/1992 | Nakao |
| 5,147,872 A | 9/1992 | Golwyn |
| 5,216,148 A | 6/1993 | Klaus |
| 5,288,514 A | 2/1994 | Ellman |
| 5,324,726 A | 6/1994 | Bock |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa |
| 5,591,227 A | 1/1997 | Dinh |
| 5,597,915 A | 1/1997 | Chambers |
| 5,599,352 A | 2/1997 | Dihn |
| 5,633,251 A | 5/1997 | Claremon |
| 5,677,282 A | 10/1997 | Oleksyszyn |
| 5,697,967 A | 12/1997 | Dihn |
| 5,763,437 A | 6/1998 | Sato |
| 5,776,946 A | 7/1998 | McGeer |
| 5,861,380 A | 1/1999 | Gyorkos |
| 5,962,337 A | 10/1999 | Ohlmeyer |
| 6,004,942 A | 12/1999 | Firestein |
| 6,074,859 A | 6/2000 | Hirokawa |
| 6,080,568 A | 6/2000 | Day |
| 6,100,254 A | 8/2000 | Budde |
| 6,239,131 B1 | 5/2001 | Shinozaki |
| 6,277,844 B1 | 8/2001 | Spector |

(Continued)

FOREIGN PATENT DOCUMENTS

CA   2372150   11/2000

(Continued)

OTHER PUBLICATIONS

Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosia,"Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).

(Continued)

*Primary Examiner* — Susannah Chung
(74) *Attorney, Agent, or Firm* — Casimir Jones SC

(57) ABSTRACT

The present invention relates to a family of guanidine-based F1F0-ATPase inhibitors, e.g., mitochondrial F1F0-ATPase inhibitors, methods for their discovery, and their use as therapeutic agents for treating certain disorders.

15 Claims, No Drawings

U.S. PATENT DOCUMENTS

| | | | |
|---|---|---|---|
| 6,319,931 B1 | 11/2001 | Kroemer | |
| 6,506,744 B1 | 1/2003 | Alig | |
| 6,524,623 B1 | 2/2003 | Hodosh | |
| 6,524,832 B1 | 2/2003 | Kufe | |
| 2,457,405 A1 | 3/2003 | Glick | |
| 6,579,854 B1 | 6/2003 | Mitchell | |
| 6,605,593 B1 | 8/2003 | Naicker | |
| 6,613,739 B1 | 9/2003 | Naicker | |
| 6,767,533 B1 | 7/2004 | Casellas | |
| 6,824,561 B2 | 11/2004 | Soykan | |
| 6,916,813 B2 * | 7/2005 | Atwal et al. | 514/235.8 |
| 7,125,866 B1 | 10/2006 | Glick | |
| 7,144,880 B2 | 12/2006 | Glick | |
| 7,150,433 B2 | 12/2006 | Healy | |
| 7,175,953 B2 | 2/2007 | Licha | |
| 7,220,739 B2 | 5/2007 | Glick | |
| 7,250,410 B2 | 7/2007 | Bourguignon | |
| 7,276,348 B2 | 10/2007 | Glick | |
| 7,351,241 B2 | 4/2008 | Bendett | |
| 7,351,421 B2 | 4/2008 | Sung | |
| 7,572,788 B2 | 8/2009 | Glick | |
| 7,638,624 B2 | 12/2009 | Glick | |
| 7,683,046 B2 | 3/2010 | Glick | |
| 7,851,465 B2 | 12/2010 | Glick | |
| 2002/0025946 A1 | 2/2002 | Buchanan | |
| 2002/0048566 A1 | 4/2002 | El-Deiry | |
| 2002/0128208 A1 | 9/2002 | Snyder | |
| 2003/0044776 A1 | 3/2003 | Dykens | |
| 2003/0119029 A1 | 6/2003 | Glick | |
| 2004/0009972 A1 | 1/2004 | Ding | |
| 2004/0087489 A1 | 5/2004 | Ruiz | |
| 2004/0157833 A1 | 8/2004 | Harris | |
| 2004/0176358 A1 | 9/2004 | Glick | |
| 2005/0113460 A1 | 5/2005 | Glick | |
| 2005/0261176 A1 | 11/2005 | Glick | |
| 2005/0272723 A1 | 12/2005 | Glick | |
| 2006/0025388 A1 | 2/2006 | Glick | |
| 2006/0052369 A1 | 3/2006 | Glick | |
| 2006/0166975 A1 | 7/2006 | Glick | |
| 2007/0036854 A1 | 2/2007 | Glick | |
| 2007/0043033 A1 | 2/2007 | Glick | |
| 2007/0105844 A1 | 5/2007 | Glick | |
| 2007/0111994 A1 | 5/2007 | Glick | |
| 2007/0135418 A1 | 6/2007 | Glick | |
| 2007/0299059 A1 | 12/2007 | Glick | |
| 2008/0064686 A1 | 3/2008 | Durrani | |

FOREIGN PATENT DOCUMENTS

| | | |
|---|---|---|
| CA | 2457405 | 2/2003 |
| CA | 2372150 | 11/2007 |
| DE | 1810423 | 10/1969 |
| EP | 0 349 949 | 1/1990 |
| EP | 0227539 | 5/1990 |
| EP | 0 906 907 | 7/1999 |
| EP | 1143946 | 10/2001 |
| EP | 1423122 | 2/2003 |
| EP | 1398033 | 3/2004 |
| EP | 1398033 | 6/2004 |
| EP | 1622684 | 2/2006 |
| EP | 1742460 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/067988 | 9/2002 |
| WO | 02/098865 | 12/2002 |
| WO | 03/015703 | 2/2003 |
| WO | 03/014658 | 5/2003 |
| WO | 03/045901 | 6/2003 |
| WO | 03/050261 | 6/2003 |
| WO | 03/106628 | 12/2003 |
| WO | 2004/050610 | 6/2004 |
| WO | 2005/004988 | 1/2005 |
| WO | 2006/007532 | 1/2006 |
| WO | 2006/014526 | 2/2006 |
| WO | 2006/029245 | 3/2006 |
| WO | 2006/073448 | 7/2006 |
| WO | 2006/074358 | 7/2006 |
| WO | 2007/050587 | 5/2007 |
| WO | 2007/053193 | 5/2007 |
| WO | 2007/053725 | 5/2007 |
| WO | 2007/146167 | 12/2007 |
| WO | 2008/012553 | 9/2008 |
| WO | 2008/116156 | 9/2008 |
| WO | 2008/133635 | 11/2008 |
| WO | 2009/036175 | 3/2009 |
| WO | 2009/061916 | 5/2009 |

OTHER PUBLICATIONS

Wyllie, A.H., "The Genetic Regulation of Apoptosis," Current Opinion in Genetics & Development 5:97-104 (1995).

Zamzami, N., et al., "Mitochondrial Control of Nuclear Apoptosis," J. Exp. Med. 183:1533-1544 1996.

Zoratti, M., et al., "The Mitochondrial Permeability Transition," Biochimica et Biophysica Acta 1241:139-176 (1995).

International Search Report, International Patent Application No. PCT/US05/24060, dated Dec. 13, 2006.

International Search Report, International Patent Application No. PCT/US02/26171 dated Aug. 8, 2003.

International Search Report, International Patent Application No. PCT/US01/11599 dated Mar. 6, 2001.

International Search Report, International Patent Application No. PCT/US005/031942 dated Sep. 21, 2006.

Kerver et al, "In situ detection of spontaneous superoxide anion and singlet oxygen production by mitochondria in . . . ", Histochem. J., 29:229-237 [1997] (Abstract only).

Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Koopman, W.J., et al., "The MRL-lpr/lpr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 1992.

Kozbor, et al.• "The production of monoclonal antibodies from human lymphocytes", Immunol. Today, 4:72 [1983].

Lee, Sunwoo, et al., "Improved Catalysts for the Palladium-Catalyzed Synthesis of Oxindoles by . . . ", J. Org. Chem. 2001, 66, pp. 3402-3415.

Lewis et al., "Editors' view: Cancer pharmacotherapy: 21st century 'magic bullets' and changing paradigms", British Journal of Clinical Pharmacology, 2006, 62:1,pp. 1-4.

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity-10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)—Eds. John Wile & Sons, New York.

Malgrange, B., et al., "I•-Carbolines Induce Apoptotic Death of Cerebellar Granule Neurones in Cultures," NeuroReport 7(18):3041-3045 (1996).
Marino, M., et al., "Prevention of Systemic Lupus Erythematosus in MRL/lpr Mice by Administration of an Immunoglobulin . . . ," Nature Biotechnology—18:735-739 (2000).
McDonnell'—349:254-256T'J"et al., "Progression from Lymphoid Hyperplasia to High-Grade . . . Nature—349:254-256 (1991).
Miccoli, et al., "Potentiation of Lonidamine and Diazepam . . . ", Journal of the National Cancer Institute, vol. 90, No. 18, pp. 1400-1406, Sep. 1998.
Miernik et al., "The antimitotic activities of some benzodiazepines", Experientia, 1986, 42, pp. 956-958.
Miller, K.A., et al., "Benzodiazepines Prevent Neuronal Death by Apoptosis & Necrosis . . . ,"Society for Neuroscience Abstracts—24(1-2):979 (1998).
Monks, A., et., Feasibility of High-Flux Anticancer Drug Screen Using a Diverse Panel of Cultured Human Tumor Cell Lines, Journal of the National Cancer Institute, 83:757-766 (1991).
Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).
Okuyama, H., et al., "Analysis of Defective Delayed-Type Hypersensitivity in Autoimmune Mice Bearing lpr Gene," Clln. Ex p. ImmunoL 63:87-94 1986.
Okuyama, H., et al., "Effect of Cyclophosphamide Pretreatment on Defective Delayed-Type Hypersensitivity . . . ," Int Arch. Allergy Appl. Immunol. 88:394-40 (1989).
Ozols, R.F., "Paclitaxel Plus Carboplatin in the Treatment of Ovarian Cancer," Seminars in Oncology 26(1) (Supp.2:84-89 (1999).
Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042. (2000).
Parks, Daniel J. "1,4-benzodiazepine-2,5-diones as small molecule antagonists of the HDM2-p53 interaction . . . " Bioorg Med Chem. Ltrs,. 15,(2005), 765-770.
Paull, K.D., et al., "Display and analysis of patterns of differential activity of drugs against human tumor . . . ", J. Natl. Cancer Inst., 81:1088-1092 [1989] (Abstract only).
Pestell, K.E., et al., "Charactehsation of the P53 Status, BCL-2 Expression and Radiation and Platinum Drug Sensitivity of . . . ," Int J. Cancer—77:913-918 (1998).
Raboisson, P. "Structure-based design, synthesis and biological evaluative of novel 1,4-diazepines as HDM2 antagonists," Bioorg Med Chem. Ltrs., 15,(2005), 1857-1861.
Ramdas et al., "Benzodiazepine compounds as inhibitors of the Src protein tyrosine kinase . . . " Archives of Biochemistry and Biophysics 368 (1999) 394-400.
Raynaud, F.I., et al., "Intracellular Metabolism of the Orally Active Platinum Drug JM216: Influence of Glutathione Levels," Br. J. Cancer 74(3) :380-?386 (1996).
Russell, J.H., et al., "Mature T Cells of Autoimmune lpr/lpr Mice have a Defect in Antigen-Stimulated Suicide,"Proc. Nat. Acad. Sci. USA 90:4409-4413 (1993).
Sakata, K., et al., "Role of Fas/FasL Interaction in Physiology and Pathology: The Good and the Bad," Clinical Immunology and Immunopathology 87(1):1-7 (1998).
Sandstrom, P.A., et al., Autocrine Production of Extracellular Catalase Prevents Apoptosis.. Proc. Natl. Acad. Sci. USA—90:4708-4712 (1993).
Schlumpf, M., et al., "Delayed Developmental Immunotoxicity of Prenatal Benzodiazepines," Toxic. In Vitro—8 (5):1061-1065(1994).
Schoemaker, H., et al., "Specific High-Affinity Binding Sites for [3H]Ro5—4864 in Rat Brain and Kidney," The J. of Pharm and Experimental Therapeutics—225(1)61-69 (1983).
Schwab, M., et al., "Amplified DNA with Limited Homology to myc Cellular Oncogene is Shared by Human Neuroblastoma Cell Lines and . . . ," Nature—305:245-248 (1983).
Scott, C.F., et al., "Comparison of Antigen-Specific T Cell Responses in Autoimmune MRL/mp-lpr/lpr and MRUMp-++Mice," The Journal of Immunology—1322:633-639 (1994.
Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . . " J. Org. Chem. 1998, 63, pp. 6546-6553.
Sheppard, R.C., et al., "Acid-Labile Resin Linkage Agents for Use in Solid Phase Peptide Synthesis;" Int J. Peptide Protein Res. 20:451-454 (1982).
Snyder, Jane R., et al, "Dissection of melanogenesis with small molecules identifies prohibition as a regulator", Chemistry & Biol. 12:477-484, 4(2005).
Stevens, S.Y., et al., "Non Nucleic Acid Inhibitors of Protein-DNA Interactions Identified Through Combinatorial Chemistry," J. Am. Chem.Soc—118:10650-10651 (1996).
Sugimoto, T., et al., Determination of Cell Surface Membrane Antigens . . . JNCI-73: (1):51-57 (1984).
Swanson et al, "Ligand recognition by anti-DNA Autoantibodies," Biochemistry, 35:1624-1633 [1996] (Abstract only).
Swanson, P.C., et al., "Ligand Recognition by Murine Anti-DNA Autoantibodies," J. Clin. Invest 97(7):1748-1760 (1996).
Swanson, P.C.,et al., "High Resolution Ephope Mapping of an Anti-DNA Autoantibody Using Model DNA Ligands," J. Immunology 71 152(5):2601-2612 (1994).
Takahashi, T., et al., "Generalized Lymphoproliferative Disease in Mice, Caused by a Point Mutation in the Fas Ligand;" Cell 76:969-976 (1994).
Tanimoto, Y., et al., Benzodiazepine Receptor Agonists Modulate Thymocyte Apoptosis Through Reduction of the Mitochondrial . . . Jpn. J. Pharmacol. 79:177-183 (1999).
Taupin, V., et al., Endogenous Anxiogenic peptide, ODN-Diazepam-Binding Inhibitor, and Benzodiazepines . . . Lymphokine and Cytoklne Research 10(1):7-13 (1991).
Theoffopoulous, AN, et al., "Murine Models of Systemic Lupus Erythematosus," Advances in Immunology 37:269-390 (1985).
AU Patent Application No. 2006203946 Examiner's Report dated Sep. 10, 2008.
EP Search, EP Patent Application No. 05856659, mailed Dec. 9, 2008.
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochodrial ATP Synthase," The Journal of Biological Chemistry, vol. 267, No. 18,m Issue of Jun. 25, pp. 12860-12867, 1992.
Giuseppe Piedimonte, et al., "Association of Tyrosine Protein Kinase Activity With Mitochondria in Human Fibroblasts," Journal of Cellular Biochemistry 32:113-123 (1986).
EP Search, EP Patent Application No. 04 775 923.8, dated Dec. 15, 2008.
Appleby, et al., "Murine chronic graft-versus-host disease as a model of osystemic lupus erythematosus: effect of immunosuppressive drugs on disease development," Clin. Exp. Immunol. (1989) 78, 449-453.
Bastian, et al., "Casein Interference in Bovine Plasmin Assays Using a Synthetic Substrate," (1991) J Dairy Sci 74:4119-4124.
Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.
Gupta et al., "Psychitripic drugs in dermatology . . . " Database:EMbase (AN:86111413), Journal of the American Academy of Dermatology, 1986, vol. 14, No. 4, pp. 633-645.
Lowe, "Systemic treatment of severe psoriasis," The New England Journal of Medicine, 324 (5), Feb. 7, 1991, pp. 333-334.
Laupacis, et al., "Cyclosporin A: a powerful immunosuppressant", CMA Journal, May 1, 1982, vol. 126, pp. 1041-1046.
Otto, M.W., et al. (2005) J. Clin. Psychiatry 66 Suppl. 2:34-38.
Yoshi, M., et al., (2005) Nippon Yakurigaku Zasshi 125(1):33-36.
Yasuda, K., (2004) Nippon Rinsho. 62 Suppl. 12:360-363.
Dacaudin, D. (2004) 15(8):737-745.
Bonnot, O., et al., (2003) Encephale. 29(6):553-559.
International Search Report and Written Opinion, PCT/US2008/082629, mailed Jun. 1, 2009.

Lacapere, J.J., et al. (2003) Steroids 68(7-8):569-585.
Galiegue, S., et al. (2003) Curr. Med. Chem (10(16):1563-1572.
Papadopoulo, V. (2003) Ann. Pharm. Fr. 61(1):30-50.
Goethals, I., et al. (2003) Eur. J. Nucl. Med. Mol. Imaging 30(2):325-328.
Casedo, M., et al. (2002) J. Exp. Med. 196(9):1121-1125.
Buffett-Jerrott S.E. et al. (2002) Curr. Pharm. Des. 8(1):45-58.
Smyth, W.F., et al. (1998) Electrophoresis 19(16-17):2870-2882.
Yoshii, M., et al. (1998) Nihon Shinkeo Seishin Yakurigaku Zasshi, 18(2):49-54.
Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.
Varani, J., et al. (2001), J. Invest. Dermatol., 117:1335-1341.
Varani, et al., (1994), J. Clin. Invest., 94:1747-1753.
Griffith, C.E., Br. J. Dermatol., Apr. 2001; 144(4):679-81.
Stern, R.S. (1995), dermatol. clin. 13:717-722.
Fry, L (1988), Brit. J. Dermatol., 119:445-461.
Krueger GC, et al., (1984), J. Am. Acad. Dermatol., 11:937-947.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiner's Report, AU Patent App. No. 2005323519 dated Nov. 27, 2007.
EP Search, EP Patent App. No. 03 027 484.9-2117, dated Jan. 31, 2005.
Canadian Patent Search, CA Patent Application No. 2,457,405, dated Feb. 6, 2007.
Wolvetang, et al., FEBS Letters (1994), 339, 40-44.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
Godic, "New approaches to psoriasis treatment. A review." 2004. Acta Dermatoven APA, vol. 13, No. 2, pp. 50-57.
Bisaha, S.N., et al., A switch in enantiomer preference between mitochondrial F1F0-ATPase chemotypes, Bioorganic & Medicinal Chemistry Letters, 2005 15(11), pp. 2749-2751.
International Search Report and Written Opinion dated Mar. 27, 2009, PCT/US2008/076021.
Chinese Office Action, CN Patent Application No. 200580029827.4, dated Apr. 17, 2009.

Bolli, M.H., et al., "Novel Benzo[1,4]diazepin-2-one-Derivaties as Endothelin Receptor Antagonists", Journal of Medicinal Chemistry, vol. 47, No. 11, Apr. 23, 2004, pp. 2776-2795.
Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.
Cunha, 2006, "The first bismuth(III)-catalyzed guanylation of thioureas", Tetrahedron Letters 47:6955-56.
Cunha, 2002, "Bismuth nitrate pentahydrate: a new and environmentally benign reagent for guanidylation of N-benzoylthioureas", Tetrahedron Letters 43: 49-52.
Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, Mar. 26, 1999, vol. 64, No. 8, pp. 2914-2918.
Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.
Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.
Mohiuddin, G., et al., "A Versatile Synthesis of 3H-1(H), 4(H)-Benzodiazepin-2,5-diones," Indian Journal of Chenmistry, 1985, vol. 24B, pp. 905-907.
Akssira, M., et al., "New Routes to 1,4-benzodiazepin-2,5-diones," Tetrahedron (1994), vol. 50, No. 30, pp. 9051-9060.
Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.
Marc, Casper, et al., "High Yield Phase Transfer N-Alkylation of Some Benzodiazepinese by Esters of w-Halo Acids," Synthetic Communications (1998) vol. 28, No. 7, pp. 1143-1157.
Bhagavathula, Narasimharao, et al., "7-Chloro-t-(4-hydroxyphenyl_-1-methyl-3-(naphthalen-2-ylmethyl) . . . ", J. Pharmacol & Exp Ther 324: 938-947 (2008).
Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.
Mahrle, et al., Br. J. Bermatol. 1974, 91, 529-540.
Mui et al. Br. J. Dermatol. 1975, 92, 255-262.
EP Search Report dated Nov. 26, 2009, EP Patent Application No. 09003224.4.
Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.
Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.
Bossu, et al., "IL-18 cDNA vaccination protects mice from spontaneous lupus-like automimmune disease," PNAS 2003, 100: 14181-14186.
De Bandt, et al., "Systemic lupus erythematosus induced by anti-tumour necrosis factor alpha therapy: a French national survey," Arthritis Res. & Ther., 2005, 7: R545-R551.
Abunasser, et al., "Etanercept-Induced Lupus Erythematosus Presenting as a Unilateral Pleural Effusion," Chest 2008, 134: 850-853.
Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.
Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).
Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

Adachi, M., et al., "Aberrant Transcription Caused by the Insertion an Early Transposable Element . . . ," PNAS. USA—90:1756-1760 (1993).

Adelman, N.E., et al., Treatment of (NZB × NZW)F1 Disease with Anti-I-A Monoclonal Antibodies; J. Exp. Med.—158:1350.1355 (1983).

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research—14:221-228 (1994).

Beale, P.J., et al., "BCL-2 Family Protein Expression and Platinum Drug Resistance in Ovarian Carcinoma," British Journal of Cancer—82 (2) :436-440 (2000).

Beurdeley-Thomas, et al., "The peripheral benzodiazepine receptors: a review," Journal of Neuro-Oncology 46 (2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. and Demonstration of Synthesis Generality," J. Org. Chem.—62:1240-1256 (1997).

Bunin et al., "Synthesis and evaluation of 1,4-benzodiazepine libraries", Methods in Enzymology, 1996, 267, pp. 448-465.

Bunin, B.A., et al., "The Combinatorial Synthesis and Chemical and Biological Evaluation of a 1,4-Benzodiazepine Libra ," PNAS USA—91:4708-4712 (1994).

Bunin, BA., et al., "A General and Expedient Method for the Solid-Phase Synthesis of 1,4-Benzodlazepine Derivatives," J. Am. Chem. Soc.—114:10997-10998 (1992).

Chumakov,A.M., et al., "Analysis of p53 Transactivation Through High-Affinity Bindir•g Sites," Oncogene—8:3005o3011 (1993).

Churcher et al., "A new series of potent benzodiazepine y-Secretase inhibitors," Bioorganic & Medicinal Chemistry Letters 13 (2003) 179-.

Cohen, P.L., et al., "Lpr and gld: Single Gen• Models of Systemic Autoimmunity and Lymphoproliferative Disease,"Annu. Rev. Immunol. 9:243-269 (1991).

Cole et al., "The EBV-Hybridoma Technique and its Application to Human Lung Cancer", Monoclonal Antibodies and Cancer Therapy, Alan R. Liss, Inc., pp. 77-96 [1985].

Colosi, et al,"Mutational analysis of the intracellular domain of the human growth hormone recetor", J. Biol. Chem., 268:12617 [1993].

Crabtree, R.H., "A New Type of Hydrogen Bond," Science 282:2000-2001 1998.

Darrow et al., "Structurally similar small molecule photoaffinity CCK-A Agonists and Antagonists as Novel Tools . . . ", Bioorganic & Medicinal Chemistry Letters 8 (1998) 3127-3132.

Desoize, B., "Anticancer Drug Resistance and Inhibition of Apoptosis," Anicancer Research—14:2291-2294 1994.

Dichek, David A., et al., "Seeding of intravascular stents with genetically engineered endothelial cells," Laboratory Investigation, 80:5 pp. 1347-1353 (1989).

Doble, A., et al., "Labelling of Peripheral-Type Benzodiazepine B Human Brain with [aH]I 1195: Anatomical and Subcellular Distribution," Brain Research Bulletin,18:49-61 1987.

Don, A. et al., Cancer Cell, vol. 3, May 2003 497-509.

Donadio, J.V., et al., Immunosuppressive Drug Therapy in Lupus Nephritis, American Journal of Kidney Diseases 21 (3):239-250 1993.

Ermak, T.H., et al., "Treatment of Murine Lupus with Monoclonal Antibody to L3T4," Laboratory Investigation 61(4):447-456 1989.

Fuh et al, "Rational design of potent antagonists to the human growth hormone receptor", Science, 256:1677 [1992].

Gallant, J.E., et al.,"Incidence and Natural History of Cytomegalovirus Disease in Patients with Advanced Human . . . " The Journal of Infect. Disease, 166: 1223-122 (1992).

Garcia-Calvo, M., et al. "Inhibition of Human Caspases by Peptide-Based and Macromolecular Inhibitors," The Journal of Biological Chemistry 273(49):32608-32613 1998.

Gorczyca, W., et al., "Induction of DNA Slrand Breaks Associated with Apoptosis During Treatment of Leukemias," Leukemia 7(5):659-670 1993.

Gordon, C., et al.. "Chronic Therapy with Recombinant Tumor Necrosis Factor-or in Autoimmune NZB/NZW Fi Mice,"Clinical Immunology and Immunopatholoy—52:421-434 (1989).

Gordon, E.M., et al., Applications of Combinatorial Technologies to Drug Discovery. 2. Combinatorial Organic 52 Synthesis, Library Screening . . . Journal of Med. Chem. 37(10): (1994).

Grasberger, Bruce L., "Discovery and cocrystal structure of benzodiazepinedione HDM2 antagonists that activate p53 in cells", J. Med. Chem., 48, (2005), 909-912.

Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.

Hahn, B.H., et al.; "Influence of Cyclophosphamide and Other Immunosuppressive Drugs on Immune Disorders . . . ," Arthritis and Rheumatism—18(2):145-152 (1975).

Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).

Hang, L., et al., "A Spontaneous Rheumatoid Arthritis-Like Disease in MR/1 Mice," J. Exp. Mod.—155:1690-1701 1982.

Herranz, R., "Cholesystokinin Antagonists: Pharmacological and Therapeutic Potential", Medicinal Research Reviews 23 (2003) 559-603.

Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).

Horowitz, R.E., et al., "Cyclophosphamide Treatment of Mouse Systemic Lupus Erythematosus," Laboratory Investigation 21 (3): 199-206 1969.

Hulme, C. J. "Improved procedure for the solution phase preparation of 1,4-benzodiazepine-2,5-dione libraries . . . ", Org. Chem., 63,(1998), 8021-8023.

Huse et al., "Generation of a Large Combinatorial Library of the Immunoglobulin Repertoire in Phage Lambda", Science, 246:1275-1281 [1989].

International Search Report and Written Opinion of PCT/US2008/057827 dated Oct. 6, 2008.

IPER and ISR for PCT/us02/31942 mailed Feb. 2, 2007.

Itoh, N., et al., "The Polypeptide Encoded by the cDNA for Human Cell Surface Antigen Fas Can Mediate Apoptosis," Cell 66:233-243 (1991).

Jones, The non-conalent interaction of pyrrolo[2, 1-c][benzodiazepines-5, 11-diones with DNA, Anti-Cancer Drug Design, 5:249-264 (1990).

Kamal, A., "Synthesis of DNA-interactive Pyrrolo[2,1-c][1,4] benzodiazepines by employing polymer-supported reagents . . . ," Synlett, 14,(2004), 2533-35.

EP Search Report dated Jun. 23, 2010, EP Patent Application No. 10 003 823.1.

EP Search Report dated Aug. 10, 2010, EP Patent Application No. 08731682.4.

Office Action Mailed Apr. 3, 2009, U.S. Appl. No. 11/176,719, filed Jul. 6, 2005.

Office Action Mailed Aug. 19, 2009, U.S. Appl. No. 11/176,719, filed Jul. 6, 2005.

Office Action Mailed May 24, 2010, U.S. Appl. No. 11/176,719, filed Jul. 6, 2005.

EP Supplementary Search Report, EP Application No. 02794914.8 dated Nov. 6, 2008.

Lee, et al., J. Org. Chem. 1999, 64, 3060-3065.

Solomko, et al., Chemistry of Heterocyclic Compounds, vol. 11, No. 11, Nov. 1975, pp. 1231-1248.

EP Patent Application No. 05 80 4417 Supplementary European Search Report dated Mar. 26, 2009.

Algarra, et al., "Application of the Photo-Fries Rearrangement of Aryl N-Chloroacetylanthranylates as Key Step in the . . . ", Heterocycles, vol. 36 1993, pp. 2335-2344.

EP Patent Application No. 06 717616 Supplementary Search Report dated Mar. 26, 2009.

Levitzki, Alexander, "Protein Tyrosine Kinase Inhibitors as Novel Therapeutic Agents," Pharmacol. Ther. vol. 82, Nos. 2-3, pp. 231-239 (1999).

Sanchez, et al., "Tumorigenic activity of the BCR-ABL oncogenes is mediated by BCL2" Proc Natl Acad Sci U S A (Jun. 6, 1995) 92(12) 5287-5291.

Ji Yang, et al., "Prevention of Apoptosis by BCL-2; Release of Cytochrome c from Mitochondria Blocked" Science vol. 275, No. 5303, pp. 1129-113221 (1997).

Prindull, "Apoptosis in the embryo and tumorigenesis" European Journal of Cancer, vol. 31, Issue 1 (1995) pp. 116-123.

Tarpley, et al., J. Chroni Diseases (1965), 18 (abstract only).

Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.

Elz et al., 1989 Eur. J. Med Chem. 259-262.

Atwal et al., Tet Lett. 30, 1989, 7313.

Johnson, K.M., et al., Chemistry & Biology, 2005, 12:486-496.

Gatza, et al., "Manipulating the Bioenergetics of Alloreactive T Cells Causes Their Selective Apoptosis and Arrests Graft-Versus-Host Disease," Sci. Transl. Med. 3(67ra8): 1-8 (2011).

Shoemaker, et al., "The NC160 Human Tumour Cell Line Anticancer Drug Screen," Nat. Rev. Cancer 6:813-823 (2006).

Yano, Masafumi, et al., "Effect of Milrinone on Left Ventricular Relaxation and Ca2+ Uptake Function of Cardiac Sarcoplasmic Reticulum," Am. J. Physiol. Heart Circ. Physiol, 279: H1898-H1905 (2000).

* cited by examiner

$F_1F_0$-ATPASE INHIBITORS AND RELATED METHODS

RELATED APPLICATIONS

This application is a national stage of International (PCT) Patent Application Serial No. PCT/US2008/076021, filed Sep. 11, 2008, and published under PCT Article 21(2) in English, which claims the benefit of priority to U.S. Provisional Patent Application Ser. No. 60/972,553, filed Sep. 14, 2007, the contents of each of which are hereby incorporated by reference.

STATEMENT REGARDING FEDERALLY SPONSORED RESEARCH OR DEVELOPMENT

This invention was made with government support under AI047450 awarded by the National Institutes of Health. The government has certain rights in the invention.

FIELD OF THE INVENTION

The present invention relates to inhibitors of $F_1F_0$-ATPases (e.g., mitochondrial $F_1F_0$-ATPases), methods for their discovery, and their therapeutic use. In particular, the present invention relates to guanidine compounds that inhibit $F_1F_0$-ATPase, and methods of using guanidine compounds as therapeutic agents to treat a number of conditions.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also a component of the primary defense against cells and invaders (e.g., viruses) which threaten the well being of the organism.

Not surprisingly many diseases are associated with dysregulation of apoptotic cell death. Experimental models have established a cause-effect relationship between aberrant apoptotic regulation and the pathagenicity of various neoplastic, autoimmune and viral diseases. For instance, in the cell-mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of immune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

It is apparent that controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative immune disorders like lupus erythematosus and rheumatoid arthritis.

Many cytotoxic agents in clinical use exert their effect by damaging DNA (e.g., cis-diaminodichloroplatanim(II) cross-links DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations in p53 and related proteins. Based on these considerations, ideal cytotoxic drugs should only kill diseased cells and not be susceptible to chemoresistance.

One strategy to selectively kill diseased cells or block their growth is to develop drugs that selectively recognize molecules expressed in diseased cells. Thus, effective cytotoxic chemotherapeutic agents, would recognize disease indicative molecules and induce (either directly or indirectly) the death of the diseased cell. Although markers on some types of cancer cells have been identified and targeted with therapeutic antibodies and small molecules, unique traits for diagnostic and therapeutic exploitation are not known for most cancers. Moreover, for diseases like lupus, specific molecular targets for drug development have not been identified.

The need exists for improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers).

SUMMARY

The present invention provides inhibitors of $F_1F_0$-ATPases (e.g., mitochondrial $F_1F_0$-ATPases), methods for the discovery of inhibitors of $F_1F_0$-ATPases, and methods for treating various conditions using such inhibitors.

In one aspect, the invention provides a compound represented by Formula I:

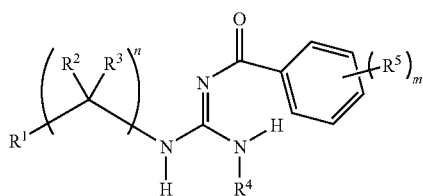

including salts, esters, and prodrugs thereof, wherein,
$R^1$ is imidazolidonyl or a heteroaryl containing at least 1 ring nitrogen atom;
$R^2$ and $R^3$ represent independently for each occurrence hydrogen or ($C_1$-$C_4$)alkyl;
$R^4$ is

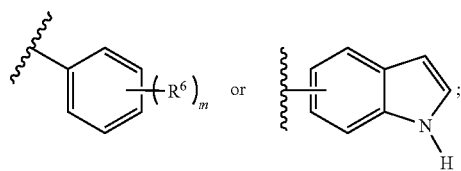

$R^5$ represents independently for each occurrence hydrogen, halogen, alkyl, haloalkyl, aryl, heteroaryl, —$NO_2$, —CN, —C(O)aryl, —C(O)heteroaryl, —C(O)N($R^2$)aryl, or —C(O)N($R^2$)heteroaryl;
$R^6$ represents independently for each occurrence hydrogen, halogen, alkyl, haloalkyl, alkoxy, aryl, heteroaryl, —$NO_2$, —CN, —$SO_2$alkyl, or —$SO_2$N(alkyl)$_2$;
n is 0, 1, 2, 3, or 4;
m represents independently for each occurrence 1 or 2; and
the stereochemical configuration at a stereocenter in a compound represented by Formula I is R, S, or a mixture thereof.

The foregoing compounds can be present in pharmaceutical compositions comprising a compound described herein and a pharmaceutically acceptable carrier.

Another aspect of the invention relates to a method of treating a subject suffering from a medical condition, comprising administering to the subject a therapeutically effective amount of one or more guanidine-based compounds described herein. A large number of diseases can be treated using the guanidine compounds described herein. For example, the compounds described herein can be used to treat diseases characterized by dysregulation of necrosis and/or apoptosis processes in a cell or tissue, diseases characterized by aberrant cell growth and/or hyperproliferation, etc., or lupus, rheumatoid arthritis, psoriasis, graft-versus-host disease, cardiovascular disease, myeloma, lymphoma, cancer, and bacterial infection.

In certain embodiments, the compositions of the present invention are used to treat immune/chronic inflammatory conditions (e.g., psoriasis, autoimmune disorders, organ-transplant rejection, and epidermal hyperplasia). In even further embodiments, the compositions of the present invention are used in conjunction with stenosis therapy to treat compromised (e.g., occluded) vessels. In some embodiments, the composition comprising a guanidine compound is administered under conditions (e.g., timing, dose, co-administration with other agent, mode of administration, selection of subject, use of targeting agents, etc.) that maximize desired effects directed at the $F_1F_0$-ATPase. In some embodiments, the subject is also administered Bz-423 or a related compound (see, e.g., U.S. Pat. Nos. 7,144,880 and 7,125,866, U.S. patent application Ser. Nos. 11/586,097, 11/585,492, 11/445,010, 11/324,419, 11/176,719, 11/110,228, 10/935,333, 10/886,450, 10/795,535, 10/634,114, 10/427, 211, 10/217,878, and 09/767,283, and U.S. Provisional Patent Nos. 60/878,519, 60/812,270, 60/802,394, 60/732,045, 60/730,711, 60/704, 102, 60/686,348, 60/641,040, 60/607,599, and 60/565,788).

In one aspect, the invention provides a method of treating a disorder selected from the group consisting of lupus, rheumatoid arthritis, psoriasis, graft-versus-host disease, myeloma, and lymphoma, comprising administering a therapeutically effective amount of a compound of Formula II to a patient in need thereof to ameliorate a symptom of the disorder, wherein Formula II is represented by:

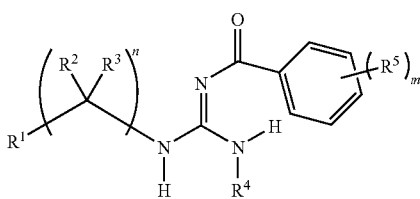

including salts, esters and prodrugs thereof, wherein
$R^1$ is a heterocyclic group;
$R^2$ and $R^3$ represent independently for each occurrence hydrogen, alkyl, aryl, heteroaryl, aralkyl, or heteroaralkyl;
$R^4$ is aryl, heteroaryl, aralkyl, or heteroaralkyl;
$R^5$ represents independently for each occurrence hydrogen, halogen, alkyl, haloalkyl, aryl, aralkyl, heteroaryl, —$NO_2$, —CN, —C(O)aryl, —C(O)heteroaryl, —C(O)N($R^2$)aryl, or —C(O)N($R^2$)heteroaryl;
n is 0, 1, 2, 3, or 4;
m is 1 or 2; and
the stereochemical configuration at a stereocenter in a compound represented by Formula II is R, S, or a mixture thereof.

In certain embodiments, the compound is embraced by the Formula I described above. In certain other embodiments, the compound is one of the compounds listed in Tables 1-6.

In another aspect, the invention provides a method of treating a disorder selected from the group consisting of cardiovascular disease and cancer. The method comprises administering a therapeutically effective amount of a compound of Formula I, as described herein, to a patient in need thereof to ameliorate a symptom of the disorder.

In another aspect, the invention provides a method of treating a bacterial infection. The method comprises administering a therapeutically effective amount of a compound of Formula I, as described herein, to a patient in need thereof to ameliorate a symptom of the bacterial infection.

In another aspect, the invention provides a method of inhibiting an $F_1F_0$-ATPase, for example, a mitochondrial $F_1F_0$-ATPase. The method comprises exposing the $F_1F_0$-ATPase to a compound of Formula I, as described herein.

In another aspect, the invention provides a method for identifying an $F_1F_0$-ATPase inhibiting agent. The method comprises the steps of: (a) providing (i) a sample comprising mitochondrial $F_1F_0$-ATPases, (ii) a first composition comprising a guanidine compound of Formula I, as described herein, and (iii) a second composition comprising a candidate $F_1F_0$-ATPase inhibiting agent; (b) contacting the sample with the first composition and the second composition; (c) measuring the mitochondrial $F_1F_0$-ATPase binding affinity for the guanidine compound and the candidate $F_1F_0$-ATPase inhibiting agent; (d) comparing the mitochondrial $F_1F_0$-ATPase binding affinity for the guanidine compound and the candidate $F_1F_0$-ATPase inhibiting agent; and (e) identifying an candidate $F_1F_0$-ATPase inhibiting agent as an $F_1F_0$-ATPase inhibiting agent by assessing the binding affinity for the candidate $F_1F_0$-ATPase inhibiting agent and cell viability of the sample.

In another aspect, the invention provides a method of identifying mitochondrial $F_1F_0$-ATPase inhibiting agents. The method comprises the steps of: (a) providing (i) first and second samples comprising mitochondrial $F_1F_0$-ATPases, (ii) a first composition comprising a guanidine compound of Formula I, as described herein, and (iii) a second composition comprising a candidate mitochondrial $F_1F_0$-ATPase inhibiting agent; (b) contacting the first sample with the first composition; (c) contacting the second sample with the second composition; (d) measuring the mitochondrial $F_1F_0$-ATPase activity for the first and second samples; (e) comparing the mitochondrial $F_1F_0$-ATPase activity for the first and second samples; and (f) identifying the candidate mitochondrial $F_1F_0$-ATPase inhibiting agent as a mitochondrial $F_1F_0$-ATPase inhibiting agent by assessing mitochondrial $F_1F_0$-ATPase activity.

In another aspect, the invention provides a method for identifying mitochondrial $F_1F_0$-ATPase inhibiting agents. The method comprises the steps of: (a) providing one or more compounds represented by Formula I, as described herein; (b) modifying the chemical structure of the one or more compounds of Formula I to generate a library of candidate mitochondrial $F_1F_0$-ATPase inhibiting agents; (c) exposing the library to samples comprising mitochondrial $F_1F_0$-ATPases; and (d) identifying as mitochondrial $F_1F_0$-ATPase inhibiting agents the candidate mitochondrial $F_1F_0$-ATPase inhibiting agents that inhibit the mitochondrial $F_1F_0$-ATPase activity in the respective sample.

DEFINITIONS

To facilitate an understanding of the present invention, a number of terms and phrases are defined below.

The term "chemical moiety" refers to any chemical compound containing at least one carbon atom. Examples of chemical moieties include, but are not limited to, aromatic chemical moieties, chemical moieties comprising sulfur, chemical moieties comprising nitrogen, oxygen, hydrophilic chemical moieties, and hydrophobic chemical moieties.

As used herein, the term "guanidine" refers to a compound having the following core structure:

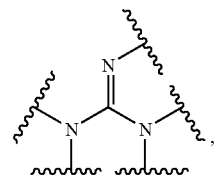

including pharmaceutically acceptable salt forms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. The aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. The term "haloaryl" refers to an aryl group that is substituted with at least one halogen.

The "heteroaryl" is art-recognized and refers to aromatic groups that include at least one ring heteroatom. In certain instances, a heteroaryl group contains 1, 2, 3, or 4 ring heteroatoms. Representative examples of heteroaryl groups includes pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. The heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. The term "haloheteroaryl" refers to an heteroaryl group that is substituted with at least one halogen.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like.

The term "imidazolidonyl" refers to a group having the formula:

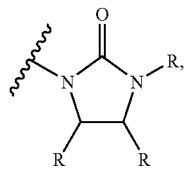

wherein R represents independently for each occurrence hydrogen, alkyl, aryl, heteroaryl, aralkyl, or heteroaralkyl.

The term "derivative" of a compound, as used herein, refers to a chemically modified compound wherein the chemical modification takes place either at a functional group of the compound (e.g., aromatic ring) or on the guanidine backbone. Such derivatives include, but are not limited to, esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

The term "$IC_{40}$" is art-recognized and refers to the concentration of a compound that is required for 40% inhibition of its target.

The term "$EC_{50}$" is art-recognized and refers to the concentration of a compound at which 50% of its maximal effect is observed.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by the dysregulation of apoptotic processes.

In some embodiments, the "target cells" of the compositions and methods of the present invention include, refer to, but are not limited to, lymphoid cells or cancer cells. Lymphoid cells include B cells, T cells, and granulocytes. Granulocycles include eosinophils and macrophages. In some embodiments, target cells are continuously cultured cells or uncultered cells obtained from patient biopsies.

In one specific embodiment, the target cells exhibit pathological growth or proliferation. As used herein, the term "pathologically proliferating or growing cells" refers to a localized population of proliferating cells in an animal that is not governed by the usual limitations of normal growth.

As used herein, the term "un-activated target cell" refers to a cell that is either in the $G_o$ phase or one to which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more cytotoxins, cytokines, or other related membrane-associated proteins characteristic of the cell type (e.g., $CD8^+$ or $CD4^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause signal transduction. An activated cancer cell may or may not be in the $G_O$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, superoxide, or hydroxyl radical levels; the activity of enzymes like kinases or phosphatases; or the energy state of the cell. For cancer cells, activating agents also include transforming oncogenes.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "dysregulation of the process of cell death" refers to any aberration in the ability (e.g., predisposition) of a cell to undergo cell death via either necrosis or apoptosis. Dysregulation of cell death is associated with or induced by a variety of conditions, including for example, immune disorders (e.g., systemic lupus erythematosus, autoimmune disorders, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an immune disorder or a chronic inflammatory condition. As used herein, the term "immune disorder" refers to any condition in which an organism produces antibodies or immune cells which recognize the organism's own molecules, cells or tissues. Non-limiting examples of immune disorders include autoimmune disorders, immune hemolytic anemia, immune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, tuberculosis, and the like.

As used herein, the term "chronic inflammatory condition" refers to a condition wherein the organism's immune cells are activated. Such a condition is characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Immune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer to the removal of undesired components from a sample. As used herein, the term "substantially purified" refers to molecules that are at least 60% free, preferably 75% free, and most preferably 90%, or more, free from other components with which they usually associated.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

As used herein, the term "competes for binding" is used in reference to a first molecule (e.g., a first compound of the present invention) with an activity that binds to the same target (e.g., the oligomycin sensitivity conferring protein in mitochondrial ATP synthase) as does a second molecule (e.g., a second compound of the present invention or other molecule that binds to the oligomycin sensitivity conferring protein in mitochondrial ATP synthase, etc.). The efficiency (e.g., kinetics or thermodynamics) of binding by the first molecule may be the same as, or greater than, or less than, the efficiency of the target binding to the second molecule. For example, the equilibrium binding constant ($K_D$) for binding to the substrate may be different for the two molecules.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

The present invention relates to inhibitors of $F_1F_0$-ATPases (e.g., mitochondrial $F_1F_0$-ATPases), methods for their discovery, and their therapeutic use. In particular, the present invention provides a family of guanidine compounds useful as $F_1F_0$-ATPase inhibitors, and methods of using such compounds as therapeutic agents to treat a number of different conditions.

Exemplary compositions and methods of the present invention are described in more detail in the following sections: I. Modulators of $F_1F_0$-ATPase Activity; II. Guanidine Compounds; III. Therapeutic Applications of Guanidine-based Compounds, IV. Pharmaceutical Compositions, Formulations, and Exemplary Administration Routes and Dosing Considerations; and V. Drug Screens.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as "Comprehensive Organic Synthesis" (B. M. Trost & I. Fleming, eds., 1991-1992); "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of $F_1F_0$-ATPase Activity

In some embodiments, the present invention regulates $F_1F_0$-ATPase activity (e.g., mitochondrial $F_1F_0$-ATPase activity) through the exposure of cells to compounds of the present invention. In some embodiments, the compounds inhibit ATP synthesis and ATP hydrolysis. The effect of the compounds can be measured by detecting any number of cellular changes. For example, mitochondrial $F_1F_0$-ATPase activity and/or cell death may be assayed as described herein and in the art. In some embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemocytometry, or a MTT dye conversion assay. Alternatively, the cell may be analyzed for the expression of genes or gene products associated with aberrations in apoptosis or necrosis.

In some embodiments, exposing the compounds of the present invention to a cell induces apoptosis. In some embodiments, the present invention induces apoptosis or arrest of cell proliferation through interacting with the mitochondrial $F_1F_0$-ATPase. In some embodiments, the compounds of the present invention inhibit mitochondrial $F_1F_0$-ATPase activity through binding the OSCP. In some embodiments, the compounds of the present invention bind the junction between the OSCP and the $F_1$ subunit of the mitochondrial $F_1F_0$-ATPase. In some embodiments, the compounds of the present invention bind the $F_1$ subunit. In certain embodiments, screening assays of the present invention permit detection of binding partners of the OSCP, $F_1$, or OSCP/$F_1$ junction.

In some embodiments, exposing the present invention to a cell induces apoptosis. In some embodiments, the present invention causes an initial increase in cellular ROS levels (e.g., $O_2^-$). In further embodiments, exposure of the compounds of the present invention to a cell causes an increase in cellular $O_2^-$ levels. In still further embodiments, the increase in cellular $O_2^-$ levels resulting from the compounds of the present invention is detectable with a redox-sensitive agent that reacts specifically with $O_2^-$ (e.g., dihydroethidium (DHE)).

In other embodiments, increased cellular $O_2^-$ levels resulting from compounds of the present invention diminish after a period of time (e.g., 10 minutes). In other embodiments, increased cellular $O_2^-$ levels resulting from the compounds of the present invention diminish after a period of time and increase again at a later time (e.g., 10 hours). In further embodiments, increased cellular $O_2^-$ levels resulting from the compounds of the present invention diminish at 1 hour and increase again after 4 hours. In some embodiments, an early increase in cellular $O_2^-$ levels, followed by a diminishing in cellular $O_2^-$ levels, followed by another increase in cellular $O_2^-$ levels resulting from the compounds of the present invention is due to different cellular processes (e.g., bimodal cellular mechanisms).

In some embodiments, the present invention causes a collapse of a cell's mitochondrial transmembrane potential ($\Delta\Psi_m$). In some embodiments, a collapse of a cell's mitochondrial $\Delta\Psi_m$ resulting from the present invention is detectable with a mitochondria-selective potentiometric probe (e.g., 3,3'-Dihexyloxacarbocyanine iodide, $DiOC_6$). In further embodiments, a collapse of a cell's mitochondrial $\Delta\Psi_m$ resulting from the present invention occurs after an initial increase in cellular $O_2^-$ levels.

In some embodiments, the present invention enables caspase activation. In other embodiments, the present invention causes the release of cytochrome c from mitochondria. In further embodiments, the present invention alters cystolic cytochrome c levels. In still other embodiments, altered cystolic cytochrome c levels resulting from the present invention are detectable by immunoblotting cytosolic fractions. In some embodiments, diminished cystolic cytochrome c levels resulting from the present invention are detectable after a period of time (e.g., 10 hours). In further preferred embodiments, diminished cystolic cytochrome c levels resulting from the present invention are detectable after 5 hours.

In other embodiments, the present invention causes the opening of the mitochondrial permeability transition pore. In some embodiments, the cellular release of cytochrome c resulting from the present invention is consistent with a collapse of mitochondrial $\Delta\Psi_m$. In still further preferred embodiments, the present invention causes an increase in cellular $O_2^-$ levels after a mitochondrial $\Delta\Psi_m$ collapse and a release of cytochrome c. In further preferred embodiments, a rise in cellular $O_2^-$ levels is caused by a mitochondrial $\Delta\Psi_m$ collapse and release of cytochrome c resulting from the present invention.

In other embodiments, the present invention causes cellular caspase activation. In some embodiments, caspase activation resulting from the present invention is measurable with a pan-caspase sensitive fluorescent substrate (e.g., FAM-VAD-fmk). In still further embodiments, caspase activation resulting from the present invention tracks with a collapse of mitochondrial $\Delta\Psi_m$. In other embodiments, the present invention causes an appearance of hypodiploid DNA. In some embodiments, an appearance of hypodiploid DNA resulting from the present invention is slightly delayed with respect to caspase activation.

In some embodiments, the molecular target for the present invention is found within mitochondria. In further embodiments, the molecular target of the present invention involves the mitochondrial ATPase. The primary sources of cellular ROS include redox enzymes and the mitochondrial respiratory chain (hereinafter MRC). In some embodiments, cytochrome c oxidase (complex IV of the MRC) inhibitors (e.g., $NaN_3$) preclude a present invention dependent increase in cellular ROS levels. In other preferred embodiments, the ubiquinol-cytochrome c reductase component of MRC complex III inhibitors (e.g., FK506) preclude a present invention dependent increase in ROS levels.

In some embodiments, an increase in cellular ROS levels result from the binding of the compounds of the present invention to a target within mitochondria. In some embodiments, the compounds of the present invention oxidize 2',7'-dichlorodihydrofluorescin (hereinafter DCF) diacetate to DCF. DCF is a redox-active species capable of detecting ROS. In further embodiments, the rate of DCF production resulting from the present invention increases after a lag period.

Antimycin A generates $O_2^-$ by inhibiting ubiquinol-cytochrome c reductase. In some embodiments, the present invention provides compounds that increase cellular ROS and this ROS is believed to arise from ubiquinol-cytochrome c. In further embodiments, the present invention increases cellular ROS production under aerobic conditions supporting state 3 respiration. In further embodiments, the compounds of the present invention do not directly target the MPT pore. In additional embodiments, the compounds of the present invention do not generate substantial ROS in the subcellular S15 fraction (e.g., cytosol; microsomes). In even further embodiments, the compounds of the present invention do not stimulate ROS if mitochondria are in state 4 respiration.

MRC complexes I-III are the primary sources of ROS within mitochondria. In some embodiments, the primary source of an increase in cellular ROS levels resulting from the compounds of the present invention emanates from these complexes as a result of inhibiting the $F_1F_0$-ATPase. Indeed, in still further embodiments, the present invention inhibits ATPase activity of bovine sub-mitochondrial particles (hereinafter SMPs). In particularly preferred embodiments, the compounds of the present invention bind to the OSCP component of the $F_1F_0$-ATPase.

Oligomycin is a macrolide natural product that binds to the $F_1F_0$-ATPase, induces a state 3 to 4 transition, and as a result, generates ROS (e.g., $O_2^-$). In some embodiments, the compounds of the present invention bind the OSCP component of the $F_1F_0$-ATPase. In some embodiments, the compounds of the present invention bind the junction between the OSCP and the $F_1$ subunit of the $F_1F_0$-ATPase. In some embodiments, the compounds of the present invention bind the $F_1$ subunit. In certain embodiments, screening assays of the present invention permit detection of binding partners of the OSCP, $F_1$, or OSCP/$F_1$ junction. OSCP is an intrinsically fluorescent protein. In certain embodiments, titrating a solution of test compounds of the present invention into an *E. Coli* sample overexpressing OSCP and/or an OSCP analog attached with a fluorescent label results in quenching of the intrinsic OSCP fluorescence. In other embodiments, fluorescent or radioactive test compounds can be used in direct binding assays. In other embodiments, competition binding experiments can be conducted. In this type of assay, test compounds are assessed for their ability to compete with a known binding compound for binding to, for example, the OSCP. In some embodiments, the compounds of the present invention cause an increase in cellular ROS levels and apoptosis in cells through regulation of the OSCP gene (e.g., altering expression of the OSCP gene). In further embodiments, the present invention functions by altering the molecular motions of the ATPase motor.

II. Guanidine Compounds

In one aspect, the invention provides a family of compounds represented by Formula

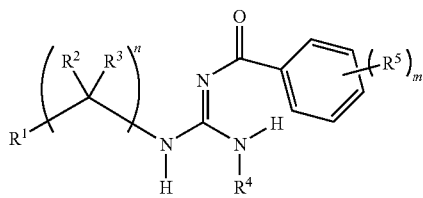

I including salts, esters, and prodrugs thereof, wherein, $R^1$ is imidazolidonyl or a heteroaryl containing at least 1 ring nitrogen atom;

$R^2$ and $R^3$ represent independently for each occurrence hydrogen or $(C_1-C_4)$alkyl;

$R^4$ is

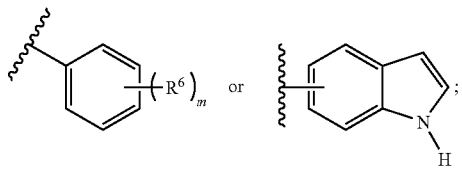

$R^5$ represents independently for each occurrence hydrogen, halogen, alkyl, haloalkyl, aryl, heteroaryl, —$NO_2$, —CN, —C(O)aryl, —C(O)heteroaryl, —C(O)N($R^2$)aryl, or —C(O)N($R^2$)heteroaryl;

$R^6$ represents independently for each occurrence hydrogen, halogen, alkyl, haloalkyl, alkoxy, aryl, heteroaryl, —$NO_2$, —CN, —$SO_2$alkyl, or —$SO_2$N(alkyl)$_2$;

n is 0, 1, 2, 3, or 4;

m represents independently for each occurrence 1 or 2; and the stereochemical configuration at a stereocenter in a compound represented by Formula I is R, S, or a mixture thereof.

In certain embodiments, $R^1$ is

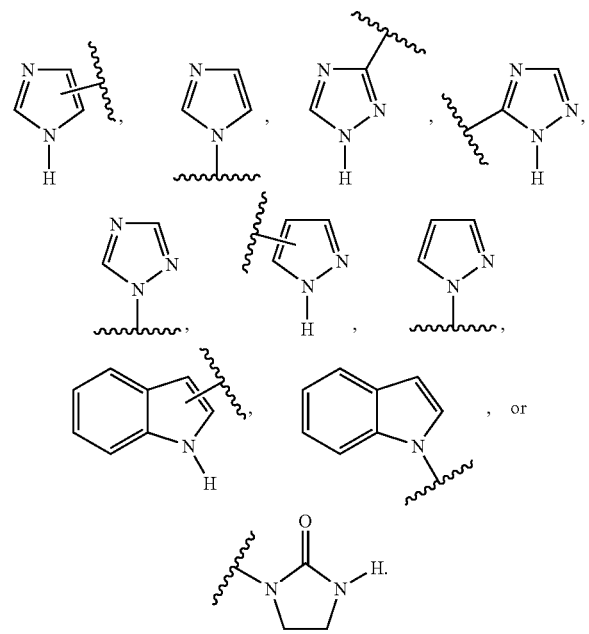

In certain other embodiments, $R^1$ is

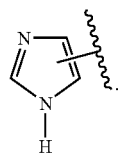

In certain other embodiments, n is 2, and $R^2$ and $R^3$ are hydrogen.

In certain other embodiments, $R^4$ is

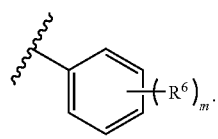

In certain other embodiments, $R^6$ is

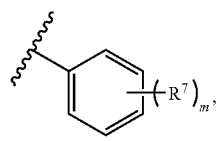

and $R^7$ represents independently for each occurrence hydrogen, halogen, alkyl, alkoxy, or —CN.

In certain other embodiments, $R^5$ represents independently for each occurrence halogen, alkyl, haloalkyl, —NO$_2$, or —CN.

In certain other embodiments, m is 1.

In certain other embodiments, $R^1$ is

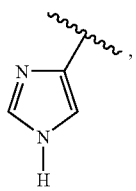

n is 2, $R^2$ and $R^3$ are hydrogen, and $R^4$ is

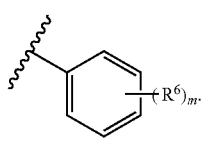

In certain other embodiments, $R^1$ is

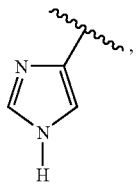

n is 2, $R^2$ and $R^3$ are hydrogen, $R^4$ is

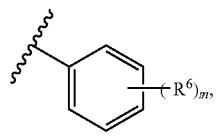

$R^5$ is halogen, alkyl, haloalkyl, —NO$_2$, or —CN, and m is 1

In certain other embodiments, the compound is one of the compounds listed in Tables 1-6 herein below. It is understood that the foregoing compounds can be combined with a pharmaceutically acceptable carrier to produce a pharmaceutical composition.

In certain embodiments, the compounds are as described in the following tables, which also provide the ClogP value for each of the compounds.

TABLE 1

| No. | X | ClogP |
|---|---|---|
| I-1 | 2-Cl | 4.7 |
| I-2 | 4-Cl | 4.7 |
| I-3 | 2-CH$_3$ | 4.5 |
| I-4 | 3-CH$_3$ | 4.5 |
| I-5 | 4-CH$_3$ | 4.5 |
| I-6 | 3-NO$_2$ | 3.7 |
| I-7 | H | 4.03 |
| I-8 | 3-Cl | 4.7 |

TABLE 2

| No. | X | Y | ClogP |
|---|---|---|---|
| II-1 | 4-Cl | H | 4.7 |
| II-2 | 3-CH$_3$ | H | 4.5 |
| II-3 | 4-CH$_3$ | H | 4.5 |
| II-4 | 3-CF$_3$ | H | 4.9 |
| II-5 | 4-CF$_3$ | H | 4.9 |
| II-6 | 3-CN | H | 3.4 |
| II-7 | 4-CN | H | 3.4 |
| II-8 | 3-F | H | 4.2 |
| II-9 | 4-F | H | 4.2 |
| II-10 | 3-Br | H | 4.8 |
| II-11 | 4-Br | H | 4.8 |
| II-12 | 3-NO$_2$ | H | 3.8 |
| II-13 | 4-NO$_2$ | H | 3.8 |
| II-14 | 1-naphthoyl | H | 5.2 |
| II-15 | 2-naphthoyl | H | 5.2 |
| II-16 | 3-Cl | 4-Cl | 5.3 |

TABLE 3

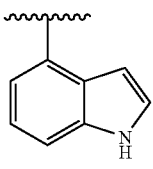

| No. | X | Y | ClogP |
|---|---|---|---|
| III-1 | H | H | 2.8 |
| III-2 | 2-Br | H | 3.7 |
| III-3 | 3-Br | H | 3.7 |
| III-4 | 2-NO$_2$ | H | 2.6 |
| III-5 | 3-NO$_2$ | H | 2.6 |
| III-6 | 3-Ph | H | 4.7 |
| III-7 | 4-Ph | H | 4.7 |
| III-8 | 2-CH$_3$ | H | 3.35 |
| III-9 | 3-CH$_3$ | H | 3.35 |
| III-10 | 4-CH$_3$ | H | 3.35 |
| III-11 | 2-OCH$_3$ | H | 2.77 |
| III-12 | 3-OCH$_3$ | H | 2.77 |
| III-13 | 4-OCH$_3$ | H | 2.77 |
| III-14 | 2-F | H | 3 |
| III-15 | 3-F | H | 3 |
| III-16 | 4-F | H | 3 |
| III-17 | 2-Cl | H | 3.56 |
| III-18 | 3-Cl | H | 3.56 |
| III-19 | 4-Cl | H | 3.56 |
| III-20 | 4-Br | H | 3.7 |
| III-21 | 4-Ph-4'-CN | H | 4.17 |
| III-22 | 4-NO$_2$ | H | 2.59 |
| III-23 | 2-CF$_3$ | H | 3.73 |
| III-24 | 3-CF$_3$ | H | 3.73 |
| III-25 | 4-CF$_3$ | H | 3.73 |
| III-26 | 2-naphthyl | H | 4.025 |
| III-27 | 1-naphthyl | H | 4.025 |
| III-28 | 4-Ph-3'-Cl | H | 5.45 |
| III-29 | 4-Ph-4'Cl | H | 5.45 |
| III-30 | 4-Ph-2'-CH$_3$ | H | 5.2 |
| III-31 | 4-Ph-3'-CH$_3$ | H | 5.2 |
| III-32 | 4-Ph-4'-CH$_3$ | H | 5.2 |
| III-33 | 4-Ph-2'-OCH$_3$ | H | 4.66 |
| III-34 | 4-Ph-3'-OCH$_3$ | H | 4.66 |
| III-35 | 4-Ph-4'-OCH$_3$ | H | 4.66 |
| III-36 | 4-SO$_2$—CH$_3$ | H | 1.21 |
| III-37 | 3-SO$_2$—CH$_3$ | H | 1.21 |
| III-38 | 2-SO$_2$—CH$_3$ | H | 1.21 |
| III-39 | 4-SO$_2$—N(CH$_3$)$_2$ | H | 2.05 |
| III-40 | 3-SO$_2$—N(CH$_3$)$_2$ | H | 2.05 |
| III-41 | 2-Et | H | 3.88 |
| III-42 | 3-Et | H | 3.88 |
| III-43 | 4-Et | H | 3.88 |
| III-44 | 2-Et | 6-Et | 4.91 |
| III-45 | 4-Ph-3'-CN | H | 4.17 |

TABLE 4

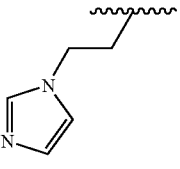

| No. | R | ClogP |
|---|---|---|
| IV-1 | 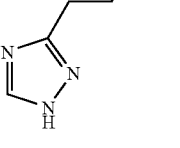 | 6.47 |
| IV-2 | 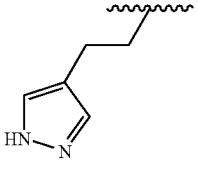 | 5.05 |
| IV-3 | 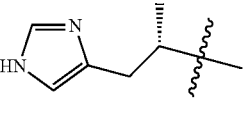 | 4.48 |
| IV-4 | 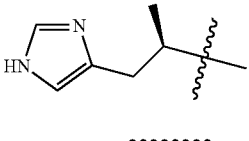 | 5.01 |
| IV-5 | | 5.05 |
| IV-6 | | 5.05 |
| IV-7 | 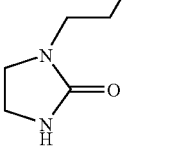 | 4.56 |

TABLE 4-continued
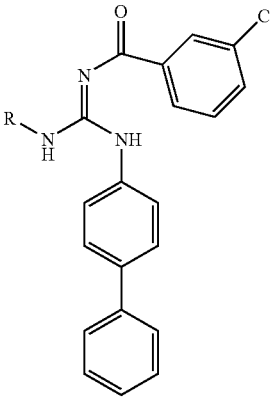
| No. | R | ClogP |
|---|---|---|
| IV-8 | 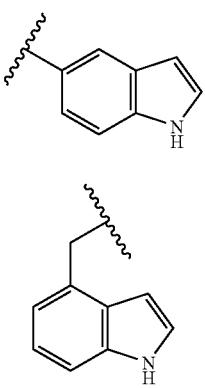 | 6.47 |
| IV-9 | 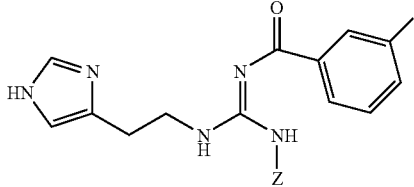 | 6.80 |
TABLE 5
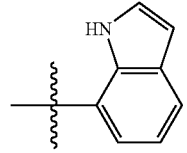
| No. | Z | ClogP |
|---|---|---|
| V-1 | 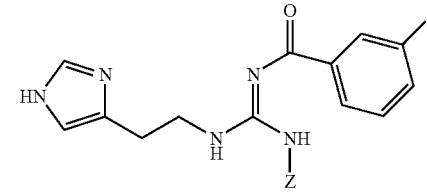 | 2.84 |
| V-2 | 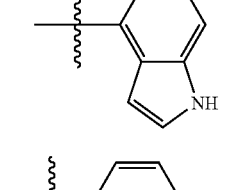 | 2.84 |
| V-3 | 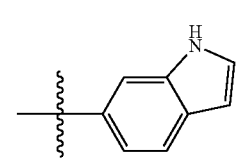 | 2.84 |
TABLE 5-continued
| No. | Z | ClogP |
|---|---|---|
| V-4 | | 2.84 |
| V-5 | | 3.45 |
| V-6 | | 3.24 |
TABLE 6
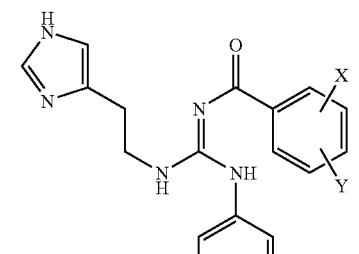
| No. | X | Y | ClogP |
|---|---|---|---|
| VI-1 | 4-CH$_3$ | H | 4.53 |
| VI-2 | 3-CH$_3$ | H | 4.53 |
| VI-3 | 3-CF$_3$ | H | 4.91 |
| VI-4 | 4-CF$_3$ | H | 4.91 |
| VI-5 | 3-CN | H | 3.46 |
| VI-6 | 4-CN | H | 3.46 |
| VI-7 | 3-F | H | 4.17 |
| VI-8 | 4-F | H | 4.17 |
| VI-9 | 3-Cl | 4-Cl | 5.33 |
| VI-10 | 3-Br | H | 4.89 |
| VI-11 | 4-Br | H | 4.89 |
| VI-12 | 3-NO$_2$ | H | 3.77 |
| VI-13 | 4-NO$_2$ | H | 3.77 |
| VI-14 | 4-Cl | H | 4.74 |

In certain embodiments, the compound is one of the following:
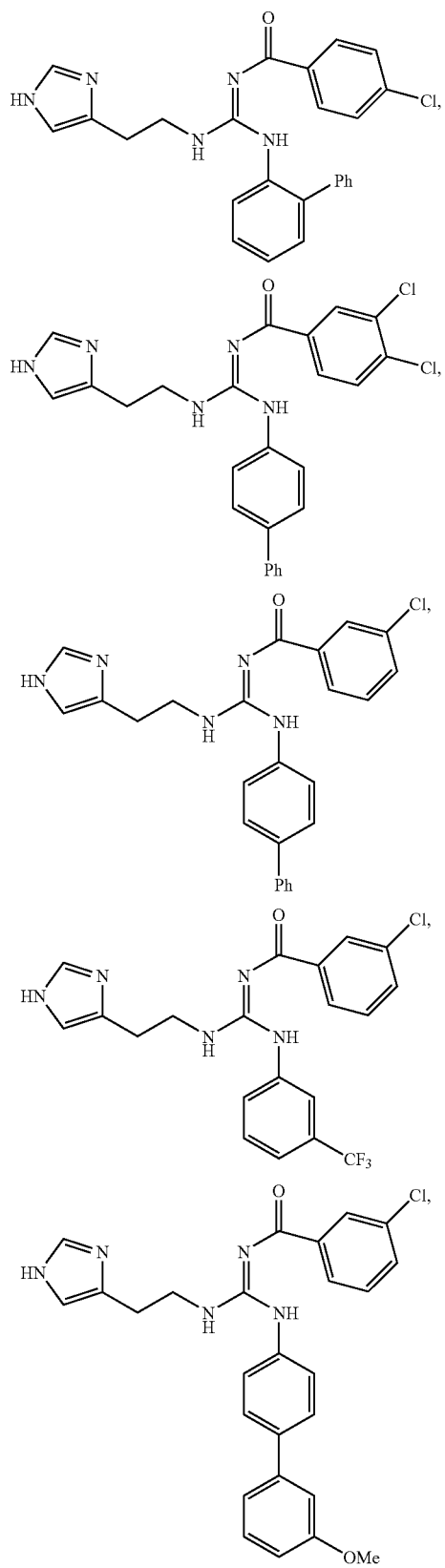
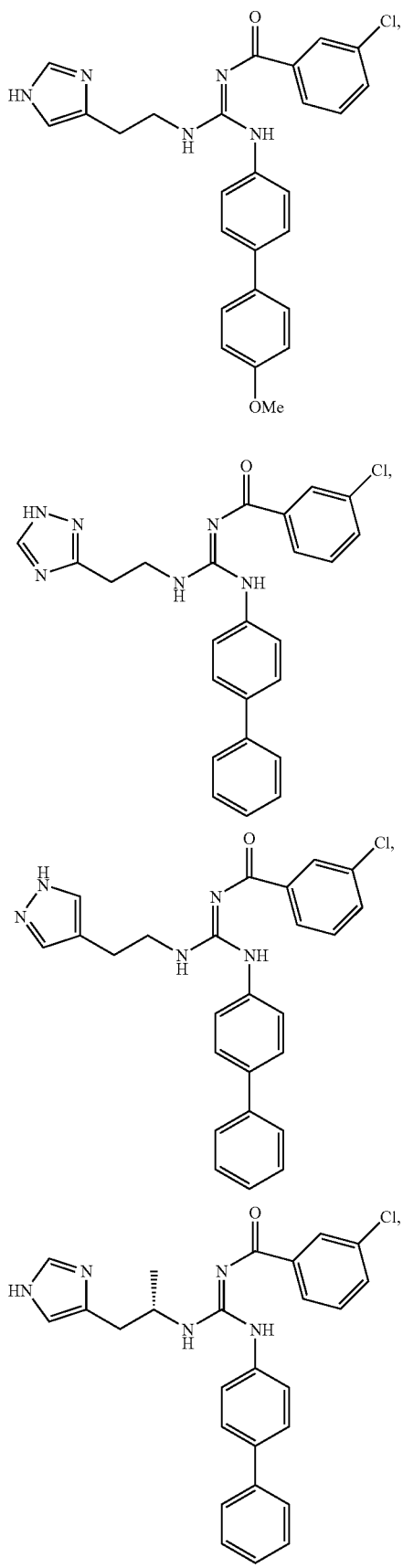

-continued

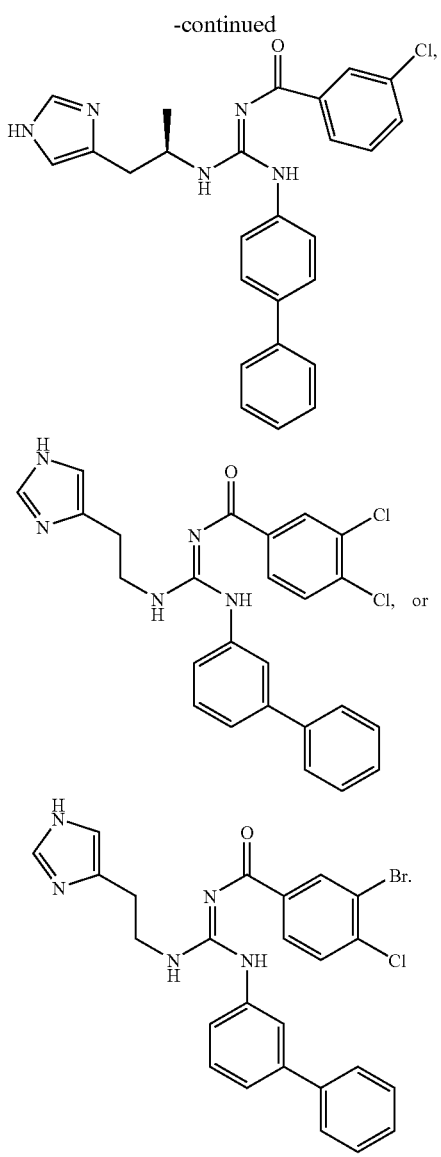

III. Therapeutic Applications of Guanidine-Based Compounds

It is contemplated that the guanidine compounds of Formula I and related guanidine-based compounds, for example, those embraced by Formula II, provide therapeutic benefits to patients suffering from any one or more of a number of conditions, e.g., diseases characterized by dysregulation of $F_1F_0$-ATPase activity, diseases characterized by dysregulation of necrosis and/or apoptosis processes in a cell or tissue, disease characterized by aberrant cell growth and/or hyperproliferation. The compounds described herein can also be used to treat a variety of dysregulatory disorders related to cellular death as described elsewhere herein. Additionally, the compounds described herein can be used to inhibit both ATP synthesis and hydrolysis.

A large number of diseases can be treated using the guanidine compounds described herein. For example, the compounds described herein can be used to treat diseases characterized by dysregulation of necrosis and/or apoptosis processes in a cell or tissue, diseases characterized by aberrant cell growth and/or hyperproliferation, etc., or lupus, rheumatoid arthritis, psoriasis, graft-versus-host disease, cardiovascular disease, myeloma, lymphoma, cancer, and bacterial infection. Although not wishing to be bound to a particular theory, it is believed that the compounds impart therapeutic benefit by modulating (e.g., inhibiting or promoting) the activity of the $F_1F_0$-ATPase complexes (e.g., mitochondrial $F_1F_0$-ATPase complexes) in affected cells or tissues. In some embodiments, the compositions of the present invention are used to treat immune/chronic inflammatory conditions (e.g., psoriasis, autoimmune disorders, organ-transplant rejection, epidermal hyperplasia). In further embodiments, the compositions of the present invention are used in conjunction with stenosis therapy to treat compromised (e.g., occluded) vessels.

In certain embodiments, a composition comprising a guanidine-based compound is administered under conditions (e.g., timing, dose, co-administration with other agent, mode of administration, selection of subject, use of targeting agents, etc.) that maximize desired effects directed at the $F_1F_0$-ATPase.

In certain embodiments, the invention provides a method of treating a disorder selected from the group consisting of lupus, rheumatoid arthritis, psoriasis, graft-versus-host disease, myeloma, and lymphoma, comprising administering a therapeutically effective amount of a compound of Formula II to a patient in need thereof to ameliorate a symptom of the disorder, wherein Formula II is represented by:

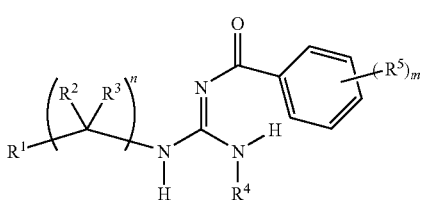

II including salts, esters and prodrugs thereof, wherein
$R^1$ is a heterocyclic group;
$R^2$ and $R^3$ represent independently for each occurrence hydrogen, alkyl, aryl, heteroaryl, aralkyl, or heteroaralkyl;
$R^4$ is aryl, heteroaryl, aralkyl, or heteroaralkyl;
$R^5$ represents independently for each occurrence hydrogen, halogen, alkyl, haloalkyl, aryl, aralkyl, heteroaryl, —$NO_2$, —CN, —C(O)aryl, —C(O)heteroaryl, —C(O)N($R^2$)aryl, or —C(O)N($R^2$)heteroaryl;
n is 0, 1, 2, 3, or 4;
m is 1 or 2; and
the stereochemical configuration at a stereocenter in a compound represented by Formula II is R, S, or a mixture thereof.

In certain embodiments, $R^1$ is heteroaryl or imidazolidonyl. In certain embodiments, $R^2$ and $R^3$ represent independently for each occurrence hydrogen, alkyl, or aryl. In certain embodiments, $R^4$ is aryl. In certain embodiments, n is 2, and m is 1. In certain embodiments, $R^2$ and $R^3$ represent independently for each occurrence hydrogen, alkyl, or aryl; $R^4$ is aryl; n is 2; and m is 1. In certain embodiments, said compound is a compound of formula I described above. In certain embodiments, said compound is one of the compounds listed in Tables 1-6.

In certain embodiments, the invention relates to a method of treating a disorder selected from the group consisting of cardiovascular disease and cancer, comprising administering a therapeutically effective amount of a compound of Formula I to a patient in need thereof to ameliorate a symptom of the disorder, wherein Formula I is represented by:

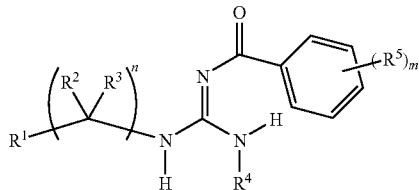

including salts, esters, and prodrugs thereof, wherein, $R^1$ is imidazolidonyl or a heteroaryl containing at least 1 ring nitrogen atom;

$R^2$ and $R^3$ represent independently for each occurrence hydrogen or $(C_1-C_4)$alkyl;

$R^4$ is

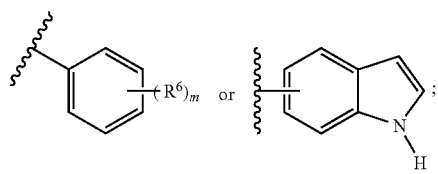

$R^5$ represents independently for each occurrence hydrogen, halogen, alkyl, haloalkyl, aryl, heteroaryl, —$NO_2$, —CN, —C(O)aryl, —C(O)heteroaryl, —C(O)N($R^2$)aryl, or —C(O)N($R^2$)heteroaryl;

$R^6$ represents independently for each occurrence hydrogen, halogen, alkyl, haloalkyl, alkoxy, aryl, heteroaryl, —$NO_2$, —CN, —$SO_2$alkyl, or —$SO_2$N(alkyl)$_2$;

n is 0, 1, 2, 3, or 4;

m represents independently for each occurrence 1 or 2; and the stereochemical configuration at a stereocenter in a compound represented by Formula I is R, S, or a mixture thereof.

In certain embodiments, $R^1$ is

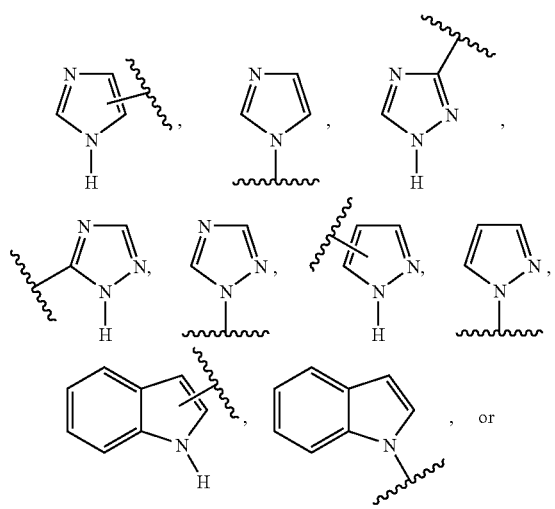

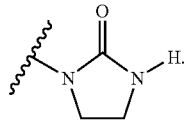

In certain other embodiments, $R^1$ is

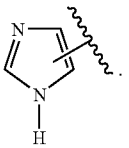

In certain other embodiments, n is 2, and $R^2$ and $R^3$ are hydrogen. In certain other embodiments, $R^4$ is

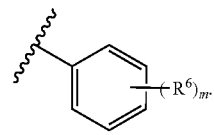

In certain other embodiments, $R^6$ is

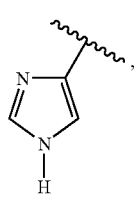

and $R^7$ represents independently for each occurrence hydrogen, halogen, alkyl, alkoxy, or —CN. In certain other embodiments, $R^5$ represents independently for each occurrence halogen, alkyl, haloalkyl, —$NO_2$, or —CN. In certain other embodiments, m is 1. In certain other embodiments, $R^1$ is

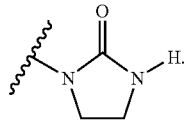

n is 2, $R^2$ and $R^3$ are hydrogen, and $R^4$ is

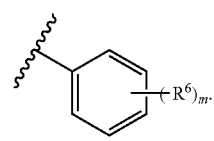

In certain other embodiments, $R^1$ is

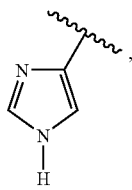

n is 2, $R^2$ and $R^3$ are hydrogen, $R^4$ is

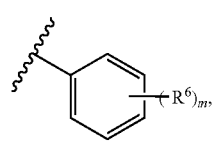

$R^5$ is halogen, alkyl, haloalkyl, —$NO_2$, or —CN, and m is 1.
In certain other embodiments, the compound is one of the compounds listed in Tables 1-6.

In certain embodiments, the invention relates to a method of treating a bacterial infection, comprising administering a therapeutically effective amount of a compound of Formula I to a patient in need thereof to ameliorate a symptom of the bacterial infection, wherein Formula I is represented by:

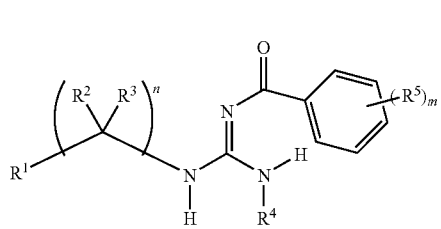

I including salts, esters, and prodrugs thereof, wherein, $R^1$ is imidazolidonyl or a heteroaryl containing at least 1 ring nitrogen atom;

$R^2$ and $R^3$ represent independently for each occurrence hydrogen or ($C_1$-$C_4$)alkyl;

$R^4$ is

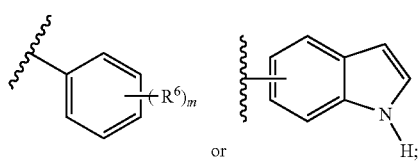

$R^5$ represents independently for each occurrence hydrogen, halogen, alkyl, haloalkyl, aryl, heteroaryl, —$NO_2$, —CN, —C(O)aryl, —C(O)heteroaryl, —C(O)N($R^2$)aryl, or —C(O)N($R^2$)heteroaryl;

$R^6$ represents independently for each occurrence hydrogen, halogen, alkyl, haloalkyl, alkoxy, aryl, heteroaryl, —$NO_2$, —CN, —$SO_2$alkyl, or —$SO_2$N(alkyl)$_2$;

n is 0, 1, 2, 3, or 4;

m represents independently for each occurrence 1 or 2; and the stereochemical configuration at a stereocenter in a compound represented by Formula I is R, S, or a mixture thereof.

In certain embodiments, $R^1$ is

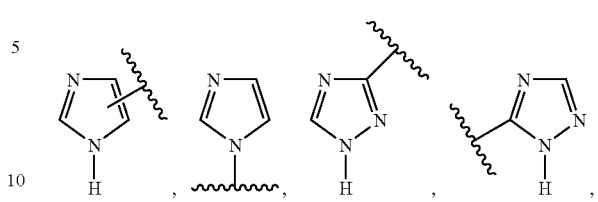

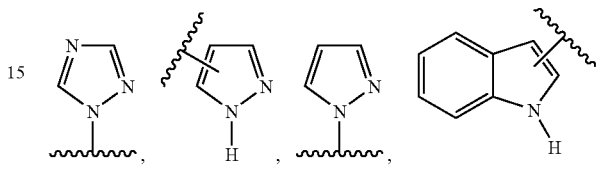

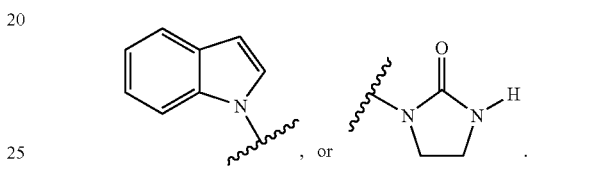

In certain other embodiments, $R^1$ is

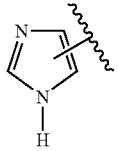

In certain other embodiments, n is 2, and $R^2$ and $R^3$ are hydrogen. In certain other embodiments, $R^4$ is

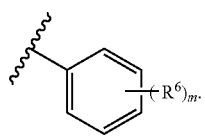

In certain other embodiments, $R^6$ is

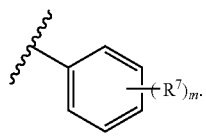

and $R^7$ represents independently for each occurrence hydrogen, halogen, alkyl, alkoxy, or —CN. In certain other embodiments, $R^5$ represents independently for each occurrence halogen, alkyl, haloalkyl, —$NO_2$, or —CN. In certain other embodiments, m is 1. In certain other embodiments, $R^1$ is

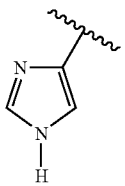

n is 2, $R^2$ and $R^3$ are hydrogen, and $R^4$ is

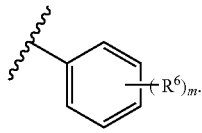

In certain other embodiments, $R^1$ is

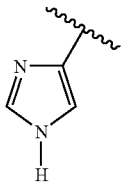

n is 2, $R^2$ and $R^3$ are hydrogen, $R^4$ is

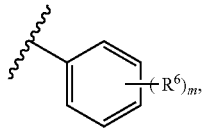

$R^5$ is halogen, alkyl, haloalkyl, —$NO_2$, or —CN, and m is 1. In certain other embodiments, the compound is one of the compounds listed in Tables 1-6.

The patient in the methods described herein is preferably a mammal (e.g., murine, simian, equine, bovine, porcine, canine, feline, and the like), and most preferably a human.

Additionally, the guanidine compounds described herein can be used in combination with at least one other therapeutic agent, such as Bz-423 (a benzodiazepine compound as described in U.S. Pat. Nos. 7,144,880 and 7,125,866, U.S. patent application Ser. Nos. 11/586,097, 11/585,492, 11/445, 010, 11/324,419, 11/176,719, 11/110,228, 10/935,333, 10/886,450, 10/795,535, 10/634,114, 10/427, 211, 10/217, 878, and 09/767,283, and U.S. Provisional Patent Nos. 60/878,519, 60/812,270, 60/802,394, 60/732,045, 60/730, 711, 60/704,102, 60/686,348, 60/641,040, 60/607,599, 60/565,788), potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin) in along with a pharmaceutically-acceptable carrier or diluent in a pharmaceutical composition.

Additionally, any one or more of these compounds can be used to treat a $F_1F_0$-ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a patient.

As indicated above, the guanidine compounds described herein can be used in the treatment of a bacterial infection. A variety of bacteria are contemplated to be susceptible to the guanidine compounds. Representative bacteria include Staphylococci species, e.g., *S. aureus*; Enterococci species, e.g., *E. faecalis* and *E. faecium*; Streptococci species, e.g., *S. pyogenes* and *S. pneumoniae*; *Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include Mycobacteria species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum*; Corynebacteria species, e.g., *C. diphtheriae*; *Vibrio* species, e.g., *V. cholerae*; *Campylobacter* species, e.g., *C. jejuni*; *Helicobacter* species, e.g., *H. pylori*; *Pseudomonas* species, e.g., *P. aeruginosa*; *Legionella* species, e.g., *L. pneumophila*; *Treponema* species, e.g., *T. pallidum*; *Borrelia* species, e.g., *B. burgdorferi*; *Listeria* species, e.g., *L monocytogenes*; *Bacillus* species, e.g., *B. cereus*; *Bordatella* species, e.g., *B. pertussis*; *Clostridium* species, e.g., *C. perfringens, C. tetani, C. difficile* and *C. botulinum*; *Neisseria* species, e.g., *N. meningitidis* and *N. gonorrhoeae*; *Chlamydia* species, e.g., *C. psittaci, C. pneumoniae* and *C. trachomatis*; *Rickettsia* species, e.g., *R. rickettsii* and *R. prowazekii*; *Shigella* species, e.g., *S. sonnei*; *Salmonella* species, e.g., *S. typhimurium*; *Yersinia* species, e.g., *Y. enterocolitica* and *Y. pseudotuberculosis*; *Klebsiella* species, e.g., *K. pneumoniae*; *Mycoplasma* species, e.g., *M. pneumoniae*; and *Trypanosoma brucei*. In certain embodiments, the guanidine compounds described herein are used to treat a patient suffering from a bacterial infection selected from the group consisting of S. aureus, E. faecalis, E. faecium, S. pyogenes, S. pneumonia, and P. aeruginosa. In certain embodiments, the guanidine compounds described herein are used to treat a patient suffering from a Trypanosoma brucei infection.

The antibacterial activity of the compounds described herein may be evaluated using standard assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately $5 \times 10^5$ colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 µg drug/mL and 0.25 to 0.00025 µg drug/mL. For the high concentration series, 200 µL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 µL of the appropriate solvent/diluent. Row 12 contains solvent/diluent only and serves as the control. For the first well of the low concentration series, 200 µL of an 8 µg/mL stock are added to duplicate rows of a 96-well plate. Serial two-fold dilutions are made as described above.

Daughter 96-well plates may be spotted (3.2 µL/well) from the stock plates listed above using the BioMek FX robot and used immediately or frozen at −70° C. until use. Aerobic organisms are inoculated (100 µL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat or study a variety of conditions associated with dysregulation of cell death, aberrant cell growth and hyperproliferation.

In addition, the compounds are also useful for preparing medicaments for treating or studying other disorders wherein the effectiveness of the compounds are known or predicted. Such disorders include, but are not limited to, neurological (e.g., epilepsy) or neuromuscular disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as discussed above, together with a solid support or alternatively, together with one or more pharmaceutically acceptable carriers and optionally other therapeutic agents (e.g., those described in section III hereinabove). Each carrier should be "acceptable" in the sense that it is compatible with the other ingredients of the formulation and not injurious to the subject.

Contemplated formulations include those suitable for oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, and include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described above) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bar Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or by oral administration, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depend on the type of condition being treated. For example, when the condition being treated is cancer, the additional agent can be a chemotherapeutic agent or radiation. When the condition being treated is an immune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. When the claimed compounds are co-administered with the known agent, they reduce the dosage required which, in turn, reduces the deleterious effects.

IV. Drug Screens

In some aspects, the compounds of the present invention, and other potentially useful compounds, are screened for their binding affinity to the oligomycin sensitivity conferring protein (OSCP) portion (or other portion) of the $F_1F_0$-ATPase and/or the ability to alter $F_1F_0$-ATPase activity or related biological processes. In particularly preferred embodiments, compounds are selected for use in the methods of the present invention by measuring their binding affinity to recombinant OSCP protein. A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems. While in some embodiments quantifying the intracellular level of ATP following administration of the compounds of the present invention provides an indication of the efficacy of the methods, preferred embodiments of the present invention do not require intracellular ATP or pH level quantification.

Additional embodiments are directed to measuring levels (e.g., intracellular) of superoxide in cells and/or tissues to measure the effectiveness of particular contemplated methods and compounds of the present invention. In this regard, those skilled in the art will appreciate and be able to provide a number of assays and methods useful for measuring superoxide levels in cells and/or tissues.

In some embodiments, structure-based virtual screening methodologies are contemplated for predicting the binding affinity of compounds of the present invention with OSCP.

Any suitable assay that allows for a measurement of the rate of binding or the affinity of a guanidine-based compound described herein to the OSCP can be utilized. Examples include, but are not limited to, competition binding using guanidine compounds, surface plasma resonace (SPR) and radio-immunopreciptiation assays (Lowman et al., J. Biol. Chem. 266:10982 [1991]). Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (see e.g., WO 90/05305). There are also several commercially available SPR biosensors (e.g., BiaCore, Uppsala, Sweden).

In some embodiments, compounds are screened in cell culture or in vivo (e.g., non-human or human mammals) for their ability to modulate ATP synthase activity. Any suitable assay may be utilized, including, but not limited to, cell proliferation assays (Commercially available from, e.g., Promega, Madison, Wis. and Stratagene, La Jolla, Calif.) and cell based dimerization assays. (See e.g., Fuh et al., Science, 256:1677 [1992]; Colosi et al., J. Biol. Chem., 268:12617 [1993]). Additional assay formats that find use with the present invention include, but are not limited to, assays for measuring cellular ATP levels, and cellular superoxide levels.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In other embodiments, rational design methods are used to predict and model in silico ligand-receptor interactions prior to confirming results by routine experimentation.

The invention provides a method for identifying an $F_1F_0$-ATPase inhibiting agent. The method comprises: (a) providing (i) a sample comprising mitochondrial $F_1F_0$-ATPases, (ii) a first composition comprising a guanidine compound of Formula I, and (iii) a second composition comprising a candidate $F_1F_0$-ATPase inhibiting agent; (b) contacting the sample with the first composition and the second composition; (c) measuring the mitochondrial $F_1F_0$-ATPase binding affinity of the guanidine compound and the candidate $F_1F_0$-ATPase inhibiting agent; (d) comparing the mitochondrial $F_1F_0$-ATPase binding affinity for the guanidine compound and the candidate $F_1F_0$-ATPase inhibiting agent; and (e) identifying the candidate $F_1F_0$-ATPase inhibiting agent as an $F_1F_0$-ATPase inhibiting agent by assessing the binding affinity for the candidate $F_1F_0$-ATPase inhibiting agent and cell viability of said sample.

It is understood that in certain embodiments, the step of measuring the mitochondrial $F_1F_0$-ATPase binding affinity comprises measuring the binding of the OSCP of the mitochondrial $F_1F_0$-ATPases.

In addition, the invention provides a method for identifying mitochondrial $F_1F_0$-ATPase inhibiting agents. The method comprises: (a) providing (i) first and second samples comprising mitochondrial $F_1F_0$-ATPases, (ii) a first composition comprising a guanidine compound of Formula I, and (iii) a second composition comprising a candidate mitochondrial $F_1F_0$-ATPase inhibiting agent; (b) contacting the first sample with the first composition; (c) contacting the second sample with the second composition; (d) measuring the mitochondrial $F_1F_0$-ATPase activity for the first and second samples; (e) comparing the mitochondrial $F_1F_0$-ATPase activity for the first and second samples; and (f) identifying the candidate mitochondrial $F_1F_0$-ATPase inhibiting agent as a mitochondrial $F_1F_0$-ATPase inhibiting agent by assessing mitochondrial $F_1F_0$-ATPase activity.

In certain embodiments, the step of measuring mitochondrial $F_1F_0$-ATPase activity comprises measuring the OSCP binding affinities for the guanidine compound and the candidate mitochondrial $F_1F_0$-ATPase inhibiting agent. In certain embodiments, the step of measuring mitochondrial $F_1F_0$-ATPase activity comprises measuring superoxide levels in the first and second samples.

In addition, the invention provides a method of identifying mitochondrial $F_1F_0$-ATPase inhibiting agents. The method comprises (a) providing one or more compounds represented by the Formula I, (b) modifying the chemical structure of the one or more compounds of Formula I to generate a library of candidate mitochondrial $F_1F_0$-ATPase inhibiting agents; (c) exposing said library to samples comprising mitochondrial $F_1F_0$-ATPases; and (d) identifying as mitochondrial $F_1F_0$-ATPase inhibiting agents the candidate mitochondrial $F_1F_0$-ATPase inhibiting agents that inhibit said mitochondrial $F_1F_0$-ATPase activity in the respective sample.

In certain embodiments, the step of inhibiting the mitochondrial $F_1F_0$-ATPase activity comprises generating superoxide free radicals in the respective sample. In certain embodiments, the step of inhibiting the mitochondrial $F_1F_0$-ATPase activity comprises initiating cell death in the respective sample.

In each of the foregoing methods, the guanidine-based composition of Formula I includes:

I including salts, esters, and prodrugs thereof, wherein, $R^1$ is imidazolidonyl or a heteroaryl containing at least 1 ring nitrogen atom;

$R^2$ and $R^3$ represent independently for each occurrence hydrogen or $(C_1-C_4)$alkyl;

$R^4$ is

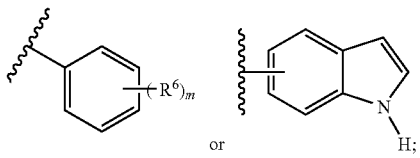

$R^5$ represents independently for each occurrence hydrogen, halogen, alkyl, haloalkyl, aryl, heteroaryl, —$NO_2$, —CN, —C(O)aryl, —C(O)heteroaryl, —C(O)N($R^2$)aryl, or —C(O)N($R^2$)heteroaryl;

$R^6$ represents independently for each occurrence hydrogen, halogen, alkyl, haloalkyl, alkoxy, aryl, heteroaryl, —$NO_2$, —CN, —$SO_2$alkyl, or —$SO_2$N(alkyl)$_2$;

n is 0, 1, 2, 3, or 4;

m represents independently for each occurrence 1 or 2; and the stereochemical configuration at a stereocenter in a compound represented by Formula I is R, S, or a mixture thereof.

In certain embodiments, is

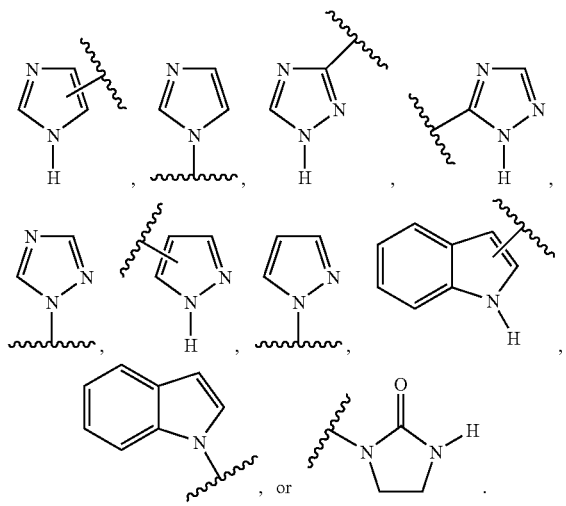

In certain other embodiments, $R^1$ is

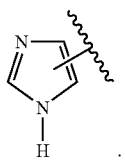

In certain other embodiments, n is 2, and $R^2$ and $R^3$ are hydrogen. In certain other embodiments, $R^4$ is

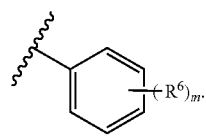

EXAMPLES

The invention now being generally described, will be more readily understood by reference to the following examples, which are included merely for purposes of illustration of certain aspects and embodiments of the present invention, and are not intended to limit the invention.

Example 1

General Procedures for the Preparation of Guanidines

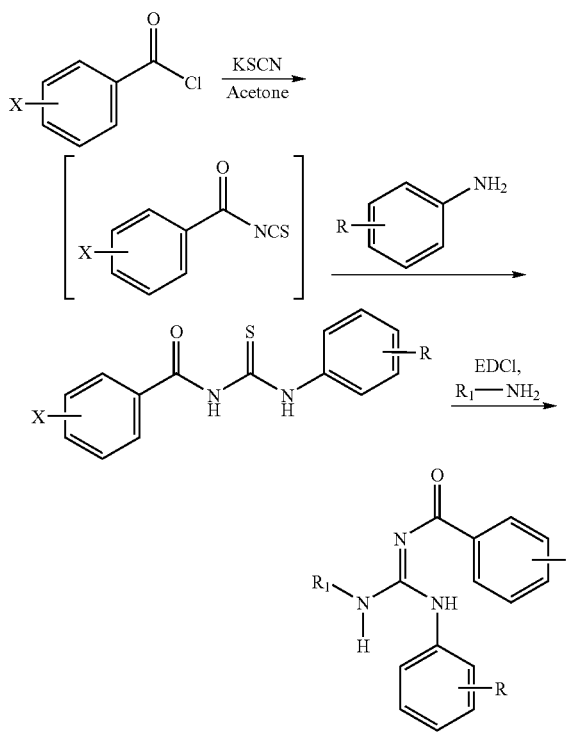

Guanidines were prepared from an acid chloride, aniline, and amine using a three-step procedure. First, the requisite acid chloride was added dropwise (neat or as a solution in an appropriate solvent) to a suspension of potassium thiocyanate in an organic solvent, and this mixture was stirred at ambient temperature for 1-4 hours. The resulting mixture was concentrated in vacuo and used immediately.

In a second step, an appropriate aniline was dissolved in an organic solvent, such as methylene chloride, at ambient temperature and the acyl isothiocyanate from the first step was added. The resulting mixture was stirred at ambient temperature for 8-16 hours. The solvents were evaporated in vacuo and the resulting residue was treated with a warm non-polar organic solvent, then allowed to cool and collected by filtration. The collected residue was rinsed with a non-polar organic solvent and dried. The resulting residue was used without further purification. Alternatively, an appropriate aniline hydrochloride salt was dissolved in an organic solvent and treated with an organic base such as triethylamine then stirred at ambient temperature for 1-4 hours. The acyl isothiocyanate from step 1 was added and the reaction mixture was stirred at ambient temperature for 8-16 hours. The solvents were removed in vacuo and the resulting residue was purified by chromatography.

In the third step, the acyl thiourea from step 2 was dissolved in a polar organic solvent such as dimethylformamide at ambient temperature and 1-ethyl-2',2'-dimethylaminopropylcarbodiimide was added. The resulting reaction mixture was stirred for 20-60 minutes, then an appropriate amine was added. The reaction mixture was stirred at ambient temperature for an additional 8-16 hours, diluted with a mixture of organic solvents, and stirred for a further 30-120 minutes. The organic solution was washed with water and the aqueous layer was re-extracted with a polar organic solvent. The combined organic layers were dried over an appropriate drying agent, filtered, and the solvents removed under reduced pressure. The desired product was purified by chromatography.

Representative Procedure for Preparation of Substituted Benzoyl Isothiocyanates.

KSCN (194 mg, 2 mmol, 1 equiv) was added to a flask, followed by anhydrous acetone (1 mL) under $N_2$ to form a suspension. 3-cyanobenzoyl chloride (332 mg, 2 mmol, 1 equiv) was added dropwise (as either liquid or 1 M solution in acetone). The reaction mixture was then stirred at room temperature for 2 h. The reaction was filtered, concentrated, and used immediately in the following reaction. Compounds that were prepared based on this representative procedure are listed in Table 7.

TABLE 7

Substrates for Preparation of Benzoyl Isothiocyanates.

| Product | KSCN | Benzoyl Chloride Compound |
|---|---|---|
| A | 2 mmol | 3-trifluoromethylbenzoyl chloride (2 mmol) |
| B | 2 mmol | 3-fluorobenzoyl chloride (2 mmol) |
| C | 2 mmol | 3-bromobenzoyl chloride (2 mmol) |
| D | 2 mmol | 3-cyanobenzoyl chloride (2 mmol) |
| E | 2 mmol | 2-naphthoyl chloride (2 mmol) |
| F | 2 mmol | 1-naphthoyl chloride (2 mmol) |
| G | 2 mmol | 2-chloropyridine-4-carbonyl (2 mmol) |
| H | 4 mmol | 4-trifluoromethylbenzoyl chloride (4 mmol) |
| I | 4 mmol | 4-fluorobenzoyl chloride (4 mmol) |
| J | 4 mmol | 4-bromobenzoyl chloride (4 mmol) |
| K | 4 mmol | 4-cyanobenzoyl chloride (4 mmol) |
| L | 2 mmol | 3,4-dichlorobenzoyl chloride (2 mmol) |

Representative Procedure for the Preparation of Thioureas.

2-aminobiphenyl (493 mg, 2.5 mmol, 1 equiv) was dissolved in methylene chloride at room temperature (0.2 M, 12.5 mL). To this, 2-chlorobenzoyl isothiocyanate was added (493 mg, 2.5 mmol, 1 equiv) and the reaction mixture was stirred overnight at room temperature. The solvent was evaporated, and the resulting residue was washed with warm hexane (50 mL×1) or benzene (for pyridine-containing products). The mixture was cooled and filtered. The residue in the filter was washed with hexane (30 mL×3) and dried. This solid was used without further purification in the coupling of thioureas with alkyl amines. Compounds that were prepared based on this representative procedure are listed in Table 8.

Representative Procedure for Preparation of Thioureas Using Aniline Hydrochloride Salts.

4-amino-3'-chlorobiphenyl hydrochloride (480 mg, 2 mmol, 1 equiv) was dissolved in methylene chloride with stirring (0.2 M, 10 mL). To this was added $NEt_3$ (d=0.726 g/mL; 202 mg, 0.28 mL, 2 mmol, 1 equiv). The mixture was then stirred for 2 h. To this was added 3-chlorobenzoyl isothiocyanate (d=1.4 g/mL; 296 mg, 210 μL, 1.5 mmol, 1 equiv) and the reaction mixture was stirred overnight. The solvent was evaporated, and the residue was purified by silica gel chromatography on the Flashmaster II purification system (ethyl acetate/hexanes). Compounds that were prepared based on this representative procedure are listed in Table 8.

TABLE 8

Substrates for Preparation of Thioureas (*indicates an Aniline Salt).

| Product | Isothiocyanate Substrate | Aniline Substrate |
|---|---|---|
| M | Benzoyl isothiocyanate (5 mmol) | 2-aminobiphenyl (5 mmol) |
| N | Benzoyl isothiocyanate (5 mmol) | 2-bromoaniline (5 mmol) |
| O | 3-chlorobenzoyl isothiocyanate (1.4 mmol) | 2-aminobiphenyl (5 mmol) |
| P | 3-chlorobenzoyl isothiocyanate (1.4 mmol) | 2-bromoaniline (5 mmol) |
| Q | 4-chlorobenzoyl isothiocyanate (5 mmol) | 2-bromoaniline (5 mmol) |
| R | 4-chlorobenzoyl isothiocyanate (2.5 mmol) | 2-aminobiphenyl (2.5 mmol) |
| S | 2-chlorobenzoyl isothiocyanate (2.5 mmol) | 2-aminobiphenyl (2.5 mmol) |
| T | 4-methylbenzoyl isothiocyanate (2 mmol) | 2-aminobiphenyl (2 mmol) |
| U | 3-methylbenzoyl isothiocyanate (2 mmol) | 2-aminobiphenyl (2 mmol) |
| V | 2-methylbenzoyl isothiocyanate (2 mmol) | 2-aminobiphenyl (2 mmol) |
| W | 3-chlorobenzoyl isothiocyanate (2 mmol) | Aniline (2 mmol) |
| X | 3-chlorobenzoyl isothiocyanate (2 mmol) | 2-methylaniline (2 mmol) |
| Y | 3-chlorobenzoyl isothiocyanate (2 mmol) | 3-methylaniline (2 mmol) |
| Z | 3-chlorobenzoyl isothiocyanate (2 mmol) | 4-methylaniline (2 mmol) |
| AA | 3-chlorobenzoyl isothiocyanate (1.5 mmol) | 2,6-diethylaniline (1.5 mmol) |
| BB | 3-chlorobenzoyl isothiocyanate (1.5 mmol) | 2-ethylaniline (1.5 mmol) |
| CC | 3-chlorobenzoyl isothiocyanate (1.5 mmol) | 3-ethylaniline (1.5 mmol) |
| DD | 3-chlorobenzoyl isothiocyanate (1.5 mmol) | 4-ethylaniline (1.5 mmol) |
| EE | 3-chlorobenzoyl isothiocyanate (2 mmol) | 3-bromoaniline (2 mmol) |
| FF | 3-chlorobenzoyl isothiocyanate (2 mmol) | 4-bromoaniline (2 mmol) |
| GG | 3-chlorobenzoyl isothiocyanate (2 mmol) | 3-aminobiphenyl (2 mmol) |
| HH | 3-chlorobenzoyl isothiocyanate (2 mmol) | 4-aminobiphenyl (2 mmol) |
| II | 3-chlorobenzoyl isothiocyanate (2 mmol) | 4-amino-4'-cyanobiphenyl (2 mmol) |
| JJ | 3-chlorobenzoyl isothiocyanate (2 mmol) | 4-amino-3'-cyanobiphenyl (2 mmol) |
| KK | 3-chlorobenzoyl isothiocyanate (2 mmol) | 4-amino-4'-chlorobiphenyl (2 mmol) |
| LL | 3-chlorobenzoyl isothiocyanate (2 mmol) | 4-amino-3'-chlorobiphenyl* (2 mmol); NEt$_3$ (2 mmol) |
| MM | 3-chlorobenzoyl isothiocyanate (2 mmol) | 4-amino-4'-methylbiphenyl* (2 mmol); NEt$_3$ (2 mmol) |
| NN | 3-chlorobenzoyl isothiocyanate (2 mmol) | 4-amino-4'methoxybiphenyl (2 mmol) |
| OO | 3-chlorobenzoyl isothiocyanate (2 mmol) | 4-amino-3'-methoxybiphenyl (2 mmol) |
| PP | 3-chlorobenzoyl isothiocyanate (2 mmol) | o-anisidine (2 mmol) |
| QQ | 3-chlorobenzoyl isothiocyanate (2 mmol) | m-anisidine (2 mmol) |
| RR | 3-chlorobenzoyl isothiocyanate (2 mmol) | p-anisidine (2 mmol) |
| SS | 3-chlorobenzoyl isothiocyanate (1.5 mmol) | 2-chloroaniline (1.5 mmol) |
| TT | 3-chlorobenzoyl isothiocyanate (1.5 mmol) | 3-chloroaniline (1.5 mmol) |
| UU | 3-chlorobenzoyl isothiocyanate (1.5 mmol) | 4-chloroaniline (1.5 mmol) |
| VV | 3-chlorobenzoyl isothiocyanate (2 mmol) | 2-fluoroaniline (2 mmol) |
| WW | 3-chlorobenzoyl isothiocyanate (1.5 mmol) | 3-fluoroaniline (1.5 mmol) |
| XX | 3-chlorobenzoyl isothiocyanate (1.5 mmol) | 4-fluoroaniline (1.5 mmol) |
| YY | 3-chlorobenzoyl isothiocyanate (1.5 mmol) | 2-trifluoromethylaniline (1.5 mmol) |
| ZZ | 3-chlorobenzoyl isothiocyanate (1.5 mmol) | 3-trifluoromethylaniline (1.5 mmol) |
| AAA | 3-chlorobenzoyl isothiocyanate (1.5 mmol) | 4-trifluoromethylaniline (1.5 mmol) |
| BBB | 3-chlorobenzoyl isothiocyanate (1.5 mmol) | 2-naphthylamine (1.5 mmol) |
| CCC | 3-chlorobenzoyl isothiocyanate (1.5 mmol) | 1-naphthylamine (1.5 mmol) |
| DDD | 3-chlorobenzoyl isothiocyanate (1.5 mmol) | 7-aminoindole (1.5 mmol) |
| EEE | 3-chlorobenzoyl isothiocyanate (1.5 mmol) | 6-aminoindole (1.5 mmol) |
| FFF | 3-chlorobenzoyl isothiocyanate (1.5 mmol) | 5-aminoindole (1.5 mmol) |
| GGG | 3-chlorobenzoyl isothiocyanate (1.5 mmol) | 4-aminoindole (1.5 mmol) |
| HHH | L (1 mmol) | 4-aminobiphenyl (1 mmol) |
| III | 4-chlorobenzoyl isothiocyanate (2 mmol) | 4-aminobiphenyl (2 mmol) |
| JJJ | B (2 mmol) | 4-aminobiphenyl (2 mmol) |
| KKK | I (2 mmol) | 4-aminobiphenyl (2 mmol) |
| LLL | 3-methylbenzoyl isothiocyanate (2 mmol) | 4-aminobiphenyl (2 mmol) |
| MMM | 4-methylbenzoyl isothiocyanate (2 mmol) | 4-aminobiphenyl (2 mmol) |
| NNN | E (2 mmol) | 4-aminobiphenyl (2 mmol) |
| OOO | F (2 mmol) | 4-aminobiphenyl (2 mmol) |
| PPP | C (2 mmol) | 4-aminobiphenyl (2 mmol) |
| QQQ | J (2 mmol) | 4-aminobiphenyl (2 mmol) |
| RRR | A (2 mmol) | 4-aminobiphenyl (2 mmol) |
| SSS | H (2 mmol) | 4-aminobiphenyl (2 mmol) |
| TTT | D (2 mmol) | 4-aminobiphenyl (2 mmol) |
| UUU | K (2 mmol) | 4-aminobiphenyl (2 mmol) |
| VVV | 3-nitrobenzoyl isothiocyanate (2 mmol) | 4-aminobiphenyl (2 mmol) |
| WWW | 4-nitrobenzoyl isothiocyanate (2 mmol) | 4-aminobiphenyl (2 mmol) |
| XXX | L (1 mmol) | 3-aminobiphenyl (1 mmol) |
| YYY | 4-chlorobenzoyl isothiocyanate (2 mmol) | 3-aminobiphenyl (2 mmol) |
| ZZZ | 4-methylbenzoyl isothiocyanate (2 mmol) | 3-aminobiphenyl (2 mmol) |
| AAAA | 4-methylbenzoyl isothiocyanate (2 mmol) | 3-aminobiphenyl (2 mmol) |
| BBBB | 3-nitrobenzoyl isothiocyanate (2 mmol) | 3-aminobiphenyl (2 mmol) |
| CCCC | 4-nitrobenzoyl isothiocyanate (2 mmol) | 3-aminobiphenyl (2 mmol) |
| DDDD | B (2 mmol) | 3-aminobiphenyl (2 mmol) |
| EEEE | I (2 mmol) | 3-aminobiphenyl (2 mmol) |
| FFFF | D (2 mmol) | 3-aminobiphenyl (2 mmol) |
| GGGG | K (2 mmol) | 3-aminobiphenyl (2 mmol) |
| HHHH | C (2 mmol) | 3-aminobiphenyl (2 mmol) |

TABLE 8-continued

Substrates for Preparation of Thioureas (*indicates an Aniline Salt).

| Product | Isothiocyanate Substrate | Aniline Substrate |
|---|---|---|
| IIII | J (2 mmol) | 3-aminobiphenyl (2 mmol) |
| JJJJ | A (2 mmol) | 4-aminobiphenyl (2 mmol) |
| KKKK | H (2 mmol) | 4-aminobiphenyl (2 mmol) |

N-(biphenyl-2-ylcarbamothioyl)benzamide (M): $^1$H NMR (500 MHz, d6-acetone): δ 7.36 (m, 1H), 7.4-7.5 (m, 8H), 7.52 (m, 2H), 7.65 (m, 1H), 7.85 (m, 1H), 7.98 (m, 2H), 10.2 (s, 1H), 12.3 (s, 1H); $^{13}$C NMR (125 MHz, (CD$_3$)$_2$CO): δ 128.2, 128.4, 128.45, 128.9, 129.0, 129.2, 129.5, 129.8, 131.1, 132.8, 134.1, 136.5, 138.9, 139.3, 168.3, 181.6; MS (nominal) for C$_{20}$H$_{16}$N$_2$OS predicted 332.1. found 332.3. 80% yield (R$_f$=0.8 in 50% ethyl acetate/50% hexanes).

N-(2-bromophenylcarbamothioyl)benzamide (N): $^1$H NMR (500 MHz, (CD$_3$)$_2$CO): δ 7.26 (m, 1H), 7.45 (t, J=7.5 Hz, 1H), 7.6 (t, J=8 Hz, 2H), 7.72 (m, 2H), 8.1 (d, J=7.5 Hz, 2H), 8.15 (d, J=8.5 Hz, 1H), 10.5 (s, 1H), 12.75 (s, 1H); $^{13}$C NMR (125 MHz, d6-acetone): δ 119.5, 128.4, 128.9, 129.1, 129.16, 129.6, 132.9, 133.6, 134.2, 137.9, 168.8, 181.0; 80% yield (R$_f$=0.5-0.8 in 50% ethyl acetate/50% hexanes).

N-(2-bromophenylcarbamothioyl)-3-chlorobenzamide (O): $^1$H NMR (500 MHz, d6-acetone): δ 7.27 (td, J=1.5 Hz, J=8 Hz, 1H), 7.46 (td, J=1 Hz, J=4 Hz, 1H), 7.62 (t, J=8 Hz, 1H), 7.74 (m, 2H), 8.05 (ddd, J=1 Hz, J=2 Hz, J=8 Hz, 1H), 8.11 (m, 1H), 8.14 (dd, J=1.5 Hz, J=8 Hz, 1H), 10.6 (s, 1H), 12.6 (s, 1H); $^1$H NMR (400 MHz, d6-DMSO): δ 7.28 (td, J=1.2 Hz, J=7.6 Hz, 1H), 7.46 (td, J=1.2 Hz, J=8 Hz, 1H), 7.58 (t, J=8 Hz, 1H), 7.75 (m, 2H), 7.88 (dd, J=1.6 Hz, J=8 Hz, 1H), 7.94 (dt, J=1.2 Hz, J=7.6 Hz, 1H), 8.06 (t, J=1.6 Hz, 1H), 11.9 (s, 1H), 12.4 (s, 1H); 68% yield.

N-(2-bromophenylcarbamothioyl)-4-chlorobenzamide (O): $^1$H NMR (400 MHz, d6-DMSO): δ 7.27 (t, J=7.6 Hz, 1H), 7.46 (t, J=7.6 Hz, 1H), 7.61 (d, J=8.4 Hz, 2H), 7.74 (d, J=8 Hz, 1H), 7.88 (d, J=8 Hz, 1H), 8.0 (d, J=8.4 Hz, 2H), 11.9, (s, 1H), 12.5 (s, 1H); $^{13}$C NMR (100.6 MHz, d6-DMSO): δ 119.5, 127.9, 128.6, 128.7, 128.8, 130.7, 130.8, 132.7, 136.9, 138.2, 167.5, 180.2; 81% yield.

N-(biphenyl-2-ylcarbamothioyl)-3-chlorobenzamide (O): $^1$H NMR (500 MHz, d6-acetone): δ 7.37 (m, 1H), 7.45 (m, 7H), 7.56 (t, J=7 Hz, 1H), 7.68 (m, 1H), 7.85 (d, J=8 Hz, 1H), 7.9 (ddd, J=1 Hz, 1.5 Hz, 8 Hz, 1H), 7.97 (t, J=7 Hz, 1H), 10.4 (s, 1H), 12.2 (s, 1H); 81% yield.

N-(biphenyl-2-ylcarbamothioyl)-4-chlorobenzamide (R): $^1$H NMR (500 MHz, d6-acetone): δ 7.35 (m, 1H), 7.4-7.5 (m, 7H), 7.57 (dt, J=2.5 Hz, 9 Hz, 2H), 7.83 (m, 1H), 7.99 (dt, J=2.5 Hz, 9 Hz, 2H), 10.3 (s, 1H), 12.2 (s, 1H); 81% yield.

N-(biphenyl-2-ylcarbamothioyl)-2-chlorobenzamide (S): $^1$H NMR (500 MHz, d6-acetone): δ 7.38 (m, 1H), 7.42-7.52 (m, 11H), 7.57 (m, 1H), 7.88 (m, 1H), 10.65 (s, 1H), 12.0 (s, 1H); 80% yield.

N-(biphenyl-2-ylcarbamothioyl)-4-methylbenzamide (T): $^1$H NMR (400 MHz, d6-acetone): δ 2.41 (s, 3H), 7.35 (m, 3H), 7.4-7.5 (m, 7H), 7.84 (m, 1H), 7.88 (d, J=8 Hz, 2H), 10.1 (s, 1H), 12.3 (s, 1H); 76% yield, N-(biphenyl-2-ylcarbamothioyl)-3-methylbenzamide (U): $^1$H NMR (400 MHz, d6-acetone): δ 2.4 (s, 3H), 7.34-7.5 (m, 10H), 7.75 (m, 1H), 7.79 (m, 1H), 7.85 (m, 1H), 10.1 (s, 1H), 12.3 (s, 1H); 81% yield.

N-(biphenyl-2-ylcarbamothioyl)-2-methylbenzamide (V): $^1$H NMR (400 MHz, d6-acetone): δ 2.33 (s, 3H), 7.24 (m, 2H), 7.3-7.5 (m, 10H), 7.85 (m, 1H), 10.3 (s, 1H), 12.2 (s, 1H); $^{13}$C NMR (100.6 MHz, d6-acetone): δ 19.76, 126.4, 128.1, 128.2, 128.3, 128.4, 128.9, 129.2, 129.8, 130.9, 131.7, 131.9, 134.7, 136.5, 137.3, 138.8, 139.3, 171.0, 181.5; 48% yield.

3-chloro-N-(phenylcarbamothioyl)benzamide (W): $^1$H NMR (500 MHz, d6-acetone): δ 7.29 (m, 1H), 7.44 (m, 2H), 7.62 (m, 1H), 7.72 (ddd, J=1 Hz, 2 Hz, 8 Hz, 1H), 7.8 (m, 2H), 8.02 (m, 1H), 8.08 (t, J=2 Hz, 1H), 10.4 (broad s, 1H), 12.7 (broad s, 1H); 59% yield.

3-chloro-N-(o-tolylcarbamothioyl)benzamide (X): $^1$H NMR (400 MHz, d6-acetone): δ 2.33 (s, 3H), 7.24 (m, 2H), 7.31 (m, 1H), 7.61 (t, J=8 Hz, 1H), 7.73 (m, 2H), 8.03 (ddd, J=1.2 Hz, 1.6 Hz, 8 Hz, 1H), 8.09 (t, J=1.6 Hz, 1H), 10.5 (s, 1H), 12.3 (s, 1H); $^{13}$C NMR (100.6 MHz, (CD$_3$)$_2$CO): δ 18.1, 126.9, 127.1, 127.6, 127.9, 129.1, 131.2, 131.3, 133.8, 134.2, 135.0, 135.2, 137.8, 167.6, 180.6; 47% yield.

3-chloro-N-(m-tolylcarbamothioyl)benzamide (Y): $^1$H NMR (400 MHz, d6-acetone): δ 2.37 (s, 3H), 7.1 (dt, J=0.8 Hz, 7.6 Hz, 1H), 7.32 (t, J=8 Hz, 1H), 7.62 (m, 3H), 7.72 (ddd, J=1.2 Hz, 2 Hz, 8 Hz, 1H), 8.03 (1H, dq, J=1.2 Hz, 8 Hz, 1H), 8.08 (m, 1H), 10.4 (s, 1H), 12.6 (s, 1H); 53% yield.

3-chloro-N-(p-tolylcarbamothioyl)benzamide (Z): $^1$H NMR (400 MHz, d6-acetone): δ 2.34 (s, 3H), 7.25 (d, J=8 Hz, 2H), 7.64 (m, 3H), 7.72 (m, 1H), 8.01 (m, 1H), 8.07 (t, J=1.6 Hz, 1H), 10.4 (s, 1H), 12.6 (s, 1H); $^{13}$C NMR (100.6 MHz, (CD$_3$)$_2$CO): δ 20.9, 124.5, 124.6, 127.6, 129.0, 129.9, 131.2, 133.8, 135.0, 136.5, 136.9, 167.7, 179.5; 55% yield.

3-chloro-N-(2,6-diethylphenylcarbamothioyl)benzamide (AA): $^1$H NMR (500 MHz, d6-acetone): δ 1.2 (m, 6H), 2.65 (m, 4H), 7.17 (d, J=7.5 Hz, 2H), 7.27 (t, J=8 Hz, 1H), 7.61 (t, J=8 Hz, 1H), 7.72 (m, 1H), 8.05 (m, 1H), 8.1 (t, J=2 Hz, 1H), 10.5 (broad s, 1H), 12.0 (broad s, 1H); 66% yield.

3-chloro-N-(2-ethylphenylcarbamothioyl)benzamide (BB): $^1$H NMR (500 MHz, d6-acetone): δ 1.23 (t, J=7.5 Hz, 3H), 2.7 (q, J=7.5 Hz, 2H), 7.27 (m, 2H), 7.35 (m, 1H), 7.43 (t, J=8 Hz, 1H), 7.7 (m, 2H), 8.05 (m, 1H), 8.11 (t, J=2 Hz, 1H), 10.5 (broad s, 1H), 12.3 (broad s, 1H); 55% yield.

3-chloro-N-(3-ethylphenylcarbamothioyl)benzamide (CC): $^1$H NMR (500 MHz, d6-acetone): δ 1.24 (td, J=2 Hz, 8 Hz, 3H), 2.68 (q, J=8 Hz, 2H), 7.13 (d, J=7.5 Hz, 1H), 7.34 (t, J=8 Hz, 1H), 7.6-7.7 (m, 3H), 7.72 (m, 1H), 8.02 (m, 1H), 8.08 (t, J=2 Hz, 1H), 10.4 (broad s, 1H), 12.7 (broad s, 1H); 67% yield.

3-chloro-N-(4-ethylphenylcarbamothioyl)benzamide (DD): $^1$H NMR (500 MHz, d6-acetone): δ 1.23 (t, J=7.5 Hz, 3H), 2.66 (q, J=7.5 Hz, 2H), 7.28 (d, J=8.5 Hz, 2H), 7.62 (t, J=8 Hz, 1H), 7.68-7.74 (m, 3H), 8.02 (dt, J=1.5 Hz, 1H), 8.08 (t, J=2 Hz, 1H), 10.4 (s, 1H), 12.6 (s, 1H); 56% yield.

N-(3-bromophenylcarbamothioyl)-3-chlorobenzamide (EE): $^1$H NMR (400 MHz, d6-acetone): δ 7.4 (t, J=8 Hz, 1H), 7.48 (m, 1H), 7.62 (t, J=8 Hz, 1H), 7.7 (m, 2H), 8.03 (m, 1H), 8.08 (t, J=2 Hz, 1H), 8.2 (t, J=2 Hz, 1H), 10.5 (s, 1H) 12.7 (s, 1H); 68% yield.

N-(4-bromophenylcarbamothioyl)-3-chlorobenzamide (FF): $^1$H NMR (400 MHz, d6-acetone): δ 7.62 (m, 3H), 7.73 (ddd, J=1.2 Hz, 2 Hz, 8 Hz, 1H), 7.78 (m, 2H), 8.02 (m, 1H), 8.08 (t, J=2 Hz, 1H), 10.5 (s, 1H), 12.7 (s, 1H); 75% yield.

N-(biphenyl-3-ylcarbamothioyl)-3-chlorobenzamide (GG): $^1$H NMR (400 MHz, d6-acetone): δ 7.4 (m, 1H), 7.5-7.78 (m, 10H), 8.05 (m, 1H), 8.1 (m, 1H), 8.19 (t, J=2 Hz, 1H), 10.5 (s, 1H), 12.8 (s, 1H); 72% yield.

N-(biphenyl-4-ylcarbamothioyl)-3-chlorobenzamide (HH): $^1$H NMR (500 MHz, d6-DMSO): δ 7.37 (t, J=7 Hz, 1H), 7.46 (t, J=8 Hz, 2H), 7.55 (t, J=8 Hz, 1H), 7.7 (m, 5H), 7.82 (d, J=9 Hz, 2H), 7.93 (d, J=8 Hz, 1H), 8.04 (t, J=2 Hz, 1H), 11.7 (s, 1H), 12.6 (s, 1H); $^{13}$C NMR (125 MHz, d6-DMSO): δ 124.5, 126.5, 126.8, 127.4, 127.5, 128.5, 128.9, 130.3, 132.7, 133.1, 134.2, 137.3, 137.9, 139.3, 166.8, 178.7; 80% yield.

3-chloro-N-(4'-cyanobiphenyl-4-ylcarbamothioyl)benzamide (II): $^1$H NMR (400 MHz, d6-DMSO): δ 7.57 (t, J=8 Hz, 1H), 7.72 (m, 1H), 7.86 (m, 4H), 7.91 (m, 5H), 8.04 (t, J=2 Hz, 1H), 11.8 (s, 1H), 12.6 (s, 1H); 73% yield.

3-chloro-N-(3'-cyanobiphenyl-4-ylcarbamothioyl)benzamide (JJ): $^1$H NMR (400 MHz, d6-DMSO): δ 7.57 (t, J=8 Hz, 1H), 7.67 (t, J=8 Hz, 1H), 7.73 (dd, J=0.8 Hz, 8 Hz, 1H), 7.84 (m, 5H), 7.91 (d, J=8 Hz, 1H), 8.05 (m, 2H), 8.2 (s, 1H), 11.8 (s, 1H), 12.5 (s, 1H); 57% yield.

3-chloro-N-(4'-chlorobiphenyl-4-ylcarbamothioyl)benzamide (KK): $^1$H NMR (400 MHz, d6-DMSO): δ 7.51 (d, J=8 Hz, 2H), 7.56 (t, J=8 Hz, 1H), 7.72 (d, J=8.8 Hz, 5H), 7.81 (d, J=8.8 Hz, 2H), 7.91 (d, J=8 Hz, 1H), 8.03 (t, J=1.6 Hz, 1H), 11.8 (s, 1H), 12.5 (s, 1H); 55% yield.

3-chloro-N-(3'-chlorobiphenyl-4-ylcarbamothioyl)benzamide (LL): $^1$H NMR (500 MHz, d6-acetone): δ 7.41 (ddd, J=1 Hz, 1.5 Hz, 8 Hz, 1H), 7.5 (t, J=8 Hz, 1H), 7.65 (t, J=8 Hz, 1H), 7.67 (ddd, J=1 Hz, 2 Hz, 8 Hz, 1H), 7.74 (m, 2H), 7.78 (m. 2H), 7.96 (m, 2H), 8.05 (ddd, J=1 Hz, 2 Hz, 8 Hz, 1H), 8.1 (t, J=2 Hz, 1H), 10.5 (s, 1H), 12.8 (s, 1H) ($R_f$=0.9 in 9:1 CH$_2$Cl$_2$/CH$_3$OH).

3-chloro-N-(4'-methylbiphenyl-4-ylcarbamothioyl)benzamide (MM): $^1$H NMR (500 MHz, d6-acetone): δ 7.27 (m, 2H), 7.6 (m, 3H), 7.7 (m, 3H), 7.9 (m, 2H), 8.02 (m, 1H), 8.09 (t, J=11.2 Hz, 1H), 10.5 (s, 1H), 12.8 (s, 1H); 63% yield ($R_f$=0.85 in 9:1 CH$_2$Cl$_2$/CH$_3$OH).

3-chloro-N-(4'-methoxybiphenyl-4-ylcarbamothioyl)benzamide (NN): $^1$H NMR (400 MHz, d6-DMSO): δ 3.79 (s, 3H), 7.02 (d, J=8.8 Hz, 2H), 7.56 (t, J=8 Hz, 1H), 7.65 (m, 4H), 7.75 (m, 3H), 7.91 (d, J=8 Hz, 1H), 8.03 (t, J=1.6 Hz, 1H), 11.7 (s, 1H), 12.5 (s, 1H); 48% yield.

3-chloro-N-(3'-methoxybiphenyl-4-ylcarbamothioyl)benzamide (OO): $^1$H NMR (500 MHz, d6-DMSO): δ 3.83 (s, 3H), 6.95 (dd, J=2 Hz, 8 Hz, 1H), 7.22 (t, J=2 Hz, 1H), 7.25 (d, J=7.5 Hz, 1H), 7.37 (t, J=8 Hz, 1H), 7.56 (t, J=8 Hz, 1H), 7.71 (m, 3H), 7.8 (d, J=8.5 Hz, 2H), 7.93 (d, J=8 Hz, 1H), 8.05 (s, 1H); $^{13}$C NMR (125 MHz, d6-DMSO): δ 55.6, 112.5, 113.6, 119.3, 124.9, 127.4, 127.9, 128.9, 130.5, 130.8, 133.2, 133.6, 134.7, 137.9, 138.3, 141.3, 160.2, 167.3, 179.1; 95% yield.

3-chloro-N-(2'-methoxybiphenyl-4-ylcarbamothioyl)benzamide: $^1$H NMR (500 MHz, d6-acetone): δ 3.78 (s, 3H), 7.04 (m, 2H), 7.22 (m, 2H), 7.58 (t, J=8 Hz, 1H), 7.6 (m, 3H), 7.84 (m, 2H), 7.95 (m, 1H), 8.04 (t, J=2 Hz, 1H), 10.3 (s, 1H), 12.8 (s, 1H); $^{13}$C NMR (125 MHz, d6-acetone): δ 55.6, 112.0, 121.4, 123.7, 127.2 128.8, 129.4, 130.1, 130.2, 130.9, 131.0, 133.6, 134.6, 134.9, 139.3, 157.1, 167.1, 178.7; 61% yield ($R_f$=0.85 in 9:1 CH$_2$Cl$_2$/CH$_3$OH).

3-chloro-N-(2-methoxyphenylcarbamothioyl)benzamide (PP): $^1$H NMR (400 MHz, d6-acetone): δ 3.97 (s, 3H), 7.0 (m, 1H), 7.13 (dd, J=1.6 Hz, 8 Hz, 1H), 7.24 (m, 1H), 7.61 (t, J=8 Hz, 1H), 7.72 (ddd, J=1.2 Hz, 2 Hz, 8 Hz, 1H), 8.02 (ddd, J=1.2 Hz, 1.6 Hz, 8 Hz, 1H), 8.08 (m, 1H), 8.83 (dd, J=1.6 Hz, 8 Hz, 1H), 10.3 (s, 1H), 13.0 (s, 1H); 66% yield.

3-chloro-N-(3-methoxyphenylcarbamothioyl)benzamide (QQ): $^1$H NMR (400 MHz, d6-acetone): δ 3.83 (s, 3H), 6.84 (ddd, J=1.2 Hz, 2.4 Hz, 8 Hz, 1H), 7.27 (m, 1H), 7.34 (t, J=8 Hz, 1H), 7.62 (m, 2H), 7.73 (ddd, J=1.2 Hz, 2.4 Hz, 8 Hz, 1H), 8.02 (m, 1H), 8.07 (t, J=1.6 Hz, 1H), 10.4 (s, 1H) 12.7 (s, 1H); 48% yield.

3-chloro-N-(4-methoxyphenylcarbamothioyl)benzamide (RR): $^1$H NMR (400 MHz, d6-acetone): δ 3.8 (s, 3H), 6.98 (m, 2H), 7.64 (m, 3H), 7.71 (m, 1H), 8.02 (m, 1H), 8.07 (t, J=1.6 Hz, 1H), 10.4 (s, 1H), 12.5 (s, 1H); 60% yield.

3-chloro-N-(2-chlorophenylcarbamothioyl)benzamide (SS): $^1$H NMR (500 MHz, d6-acetone): δ 7.34 (J=1.5 Hz, 8 Hz, 1H), 7.42 (m, 1H), 7.57 (dd, J=1.5 Hz, 8 Hz, 1H), 7.63 (t, J=8 Hz, 1H), 7.73 (m, 1H), 8.05 (ddd, J=1 Hz, 2 Hz, 8 Hz, 1H), 8.1 (t, J=1.5 Hz, 1H), 8.32 (dd, J=1.5 Hz, 8 Hz, 1H), 10.6 (broad s, 1H), 12.7 (broad s, 1H); 66% yield.

3-chloro-N-(3-chlorophenylcarbamothioyl)benzamide (TT): $^1$H NMR (500 MHz, d6-acetone): δ 7.33 (m, 1H), 7.46 (t, J=8 Hz, 1H), 7.65 (m, 2H), 7.73 (m, 1H), 8.04 (m, 1H), 8.08 (m, 2H), 10.58 (broad s, 1H), 12.78 (broad s, 1H); 87% yield.

3-chloro-N-(4-chlorophenylcarbamothioyl)benzamide (UU): $^1$H NMR (500 MHz, d6-acetone): δ 7.47 (m, 2H), 7.62 (t, J=8 Hz, 1H), 7.73 (ddd, J=1 Hz, 2 Hz, 8 Hz, 1H), 7.83 (m, 2H), 8.03 (m, 1H), 8.08 (t, J=2 Hz, 1H), 10.55 (broad s, 1H), 12.7 (broad s, 1H); 86% yield.

3-chloro-N-(2-fluorophenylcarbamothioyl)benzamide (VV): $^1$H NMR (500 MHz, d6-acetone): δ 7.24-7.36 (m, 3H), 7.62 (t, J=8 Hz, 1H), 7.72 (ddd, J=1 Hz, 2 Hz, 8 Hz, 1H), 8.04 (ddd, J=1 Hz, 2 Hz, 8 Hz, 1H), 8.1 (m, 1H), 8.37 (m, 1H), 10.6 (broad s, 1H), 12.7 (broad s, 1H); 58% yield.

3-chloro-N-(3-fluorophenylcarbamothioyl)benzamide (WW): $^1$H NMR (500 MHz, d6-acetone): δ 7.07 (m, 1H), 7.47 (m, 2H), 7.62 (t, J=8 Hz, 1H), 7.72 (m, 1H), 7.94 (m, 1H), 8.02 (m, 1H), 8.08 (t, J=2 Hz, 1H), 10.55 (broad s, 1H), 12.8 (broad s, 1H); 69% yield.

3-chloro-N-(4-fluorophenylcarbamothioyl)benzamide (XX): $^1$H NMR (500 MHz, d6-acetone): δ 7.21 (m, 2H), 7.62 (t, J=8 Hz, 1H), 7.73 (m, 1H), 7.78 (dd, J=5 Hz, 8.75 Hz, 2H), 8.03 (m, 1H), 8.08 (m, 1H), 10.45 (broad s, 1H), 12.6 (broad s, 1H); 50% yield.

3-chloro-N-(2-(trifluoromethyl)phenylcarbamothioyl)benzamide (YY): $^1$H NMR (500 MHz, d6-acetone): δ 7.56 (t, J=7.5 Hz, 1H), 7.63 (t, J=8 Hz, 1H), 7.74 (m, 2H), 7.82 (d, J=7.5 Hz, 1H), 7.95 (d, J=8 Hz, 1H), 8.06 (m, 1H), 8.12 (t, J=2 Hz, 1H), 10.75 (broad s, 1H), 12.6 (broad s, 1H); 48% yield.

3-chloro-N-(3-(trifluoromethyl)phenylcarbamothioyl)benzamide (ZZ): $^1$H NMR (500 MHz, d6-acetone): δ 7.63 (m, 2H), 7.69 (m, 1H), 7.73 (m, 1H), 7.98 (d, J=8 Hz, 1H), 8.04 (m, 1H), 8.09 (t, J=2 Hz, 1H), 8.32 (s, 1H), 10.6 (broad s, 1H), 12.8 (broad s, 1H); 62% yield.

3-chloro-N-(4-(trifluoromethyl)phenylcarbamothioyl)benzamide (AAA): $^1$H NMR (500 MHz, d6-acetone): δ 7.62 (m, 1H), 7.7-7.8 (m, 3H), 8.05 (m, 4H), 10.6 (broad s, 1H), 12.9 (broad s, 1H); 38% yield.

3-chloro-N-(4-(N,N-dimethylsulfamoyl)phenylcarbamothioyl)benzamide: $^1$H NMR (300 MHz, d6-acetone): δ 2.70 (s, 6H), 7.62 (t, J=8.0 Hz, 1H), 7.73 (dq, J=8.2, 1.2 Hz, 1H), 7.85 (dt, J=9.3, 2.1 Hz, 2H), 8.03 (dm, J=7.8 Hz, 1H), 8.08 (t, J=1.7 Hz, 1H), 8.15 (dt, J=9.3, 2.1 Hz, 2H), 10.61 (s, 1H), 13.0 (s, 1H).

3-chloro-N-(3-(N,N-dimethylsulfamoyl)phenylcarbamothioyl)benzamide: $^1$H NMR (300 MHz, d6-acetone): δ 2.72 (s, 6H), 7.61 (t, J=8.0 Hz, 1H), 7.69-7.74 (m, 3H), 7.91-7.95 (m, 1H), 8.02 (dm, J=8.0 Hz, 1H), 8.08 (t, J=1.7 Hz, 1H), 8.41 (m, 1H), 10.62 (s, 1H), 12.81 (s, 1H).

3-chloro-N-(4-(methylsulfonyl)phenylcarbamothioyl)benzamide: $^1$H NMR (300 MHz, d6-acetone): δ 3.15 (s, 3H), 7.62 (t, J=8.0 Hz, 1H), 7.73 (dm, J=8.0 Hz, 1H), 7.92-8.05 (m, 3H), 8.09 (t, J=1.8 Hz, 1H), 8.14 (dt, J=9.2, 2.1 Hz, 2H), 10.63 (s, 1H), 12.99 (s, 1H).

3-chloro-N-(3-(methylsulfonyl)phenylcarbamothioyl)benzamide: $^1$H NMR (300 MHz, d6-acetone$_6$) δ 3.16 (s, 3H), 7.62 (t, J=8.0 Hz, 1H), 7.69-7.75 (m, 2H), 7.85 (dm, J=8.0 Hz, 1H), 8.03 (dm, J=7.7 Hz, 1H), 8.07-8.11 (m, 2H), 8.46 (t, J=2.0 Hz, 1H), 10.62 (s, 1H), 12.86 (s, 1H).

3-chloro-N-(2-(methylsulfonyl)phenylcarbamothioyl)benzamide: $^1$H NMR (300 MHz, d6-acetone): δ 3.14 (s, 3H), 7.58-7.64 (m, 2H), 7.71-7.82 (m, 2H), 7.98-8.06 (m, 3H), 8.10-8.11 (m, 1H), 10.75 (s, 1H), 12.66 (s, 1H).

3-chloro-N-(naphthalen-2-ylcarbamothioyl)benzamide (BBB): $^1$H NMR (500 MHz, d6-acetone): δ 7.55 (m, 2H), 7.63 (t, J=8 Hz, 1H), 7.74 (m, 1H), 7.8 (m, 1H), 7.95 (m, 3H), 8.05 (ddd, J=1 Hz, 1.5 Hz, 8 Hz, 1H), 8.11 (m, 1H), 8.48 (m, 1H), 10.5 (broad s, 1H), 12.9 (broad s, 1H); 56% yield.

3-chloro-N-(naphthalen-1-ylcarbamothioyl)benzamide (CCC): $^1$H NMR (500 MHz, d6-acetone): δ 7.56-7.67 (m, 5H), 7.76 (ddd, J=1 Hz, 2 Hz, 8 Hz, 1H), 7.92 (d, J=8 Hz, 1H), 8.0 (m, 2H), 8.1 (m, 2H), 8.17 (t, J=2 Hz, 1H), 10.64 (broad s, 1H), 12.8 (broad s, 1H); 67% yield.

N-(1H-indol-7-ylcarbamothioyl)-3-chlorobenzamide (DDD): $^1$H NMR (500 MHz, d6-acetone): δ 6.55 (dd, J=2 Hz, 3 Hz, 1H), 7.08 (t, J=7.5 Hz, 1H), 7.26 (d, J=7.5 Hz, 1H), 7.36 (m, 1H), 7.58 (d, J=8 Hz, 1H), 7.64 (t, J=8 Hz, 1H), 7.74 (ddd, J=1 Hz, 2.5 Hz, 8 Hz, 1H), 8.05 (ddd, J=1 Hz, 1.5 Hz, 8 Hz, 1H), 8.11 (m, 1H), 10.3 (broad s, 1H), 10.6 (broad s, 1H), 12.4 (broad s, 1H); 41% yield.

N-(1H-indol-6-ylcarbamothioyl)-3-chlorobenzamide (EEE): $^1$H NMR (500 MHz, d6-acetone): δ 6.5 (m, 1H), 7.18 (m, 1H), 7.4 (m, 1H), 7.61 (t, J=8 Hz, 2H), 7.72 (ddd, J=1 Hz, 2 Hz, 8 Hz, 1H), 8.03 (m, 1H), 8.09 (t, J=2 Hz, 1H), 8.24 (s, 1H), 10.34 (broad s, 1H), 10.4 (broad s, 1H), 12.8 (broad s, 1H); 32% yield.

N-(1H-indol-5-ylcarbamothioyl)-3-chlorobenzamide (FFF): $^1$H NMR (500 MHz, d6-acetone): δ 6.53 (m, 1H), 7.35 (m, 1H), 7.39 (m, 1H), 7.47 (d, J=8.5 Hz, 1H), 7.58 (m, 1H), 7.7 (ddd, J=1 Hz, 2.5 Hz, 8 Hz, 1H), 8.0 (ddd, J=1 Hz, 2 Hz, 8 Hz, 1H), 8.07 (m, 2H), 10.35 (broad d, 2H), 12.64 (broad s, 1H); 30% yield.

N-(1H-indol-4-ylcarbamothioyl)-3-chlorobenzamide (GGG): $^1$H NMR (500 MHz, d6-acetone): δ 6.69 (m, 1H), 7.18 (t, J=8 Hz, 1H), 7.38 (d, J=8 Hz, 1H), 7.44 (m, 1H), 7.6 (d, J=8 Hz, 1H), 7.7 (ddd, J=1 Hz, 2 Hz, 8 Hz, 1H), 8.04 (m, 1H), 8.12 (t, J=2 Hz, 1H), 8.38 (m, 1H), 10.4 (broad s, 1H), 10.5 (broad s, 1H), 13.2 (broad s, 1H); 49% yield.

N-(biphenyl-4-ylcarbamothioyl)-3,4-dichlorobenzamide (HHH): $^1$H NMR (500 MHz, d6-DMSO): δ 7.39 (m, 1H), 7.48 (m, 2H), 7.72 (m, 4H), 7.82 (m, 3H), 7.93 (dd, J=2 Hz, 8 Hz, 1H), 8.25 (d, J=2 Hz, 1H), 11.8 (s, 1H), 12.5 (s, 1H); 44% yield.

N-(biphenyl-4-ylcarbamothioyl)-4-chlorobenzamide (III): $^1$H NMR (500 MHz, d6-acetone): δ 7.38 (m, 1H), 7.48 (m, 2H), 7.65 (m, 2H), 7.74 (m, 4H), 7.94 (m, 2H), 8.12 (m, 2H), 10.4 (s, 1H), 12.8 (s, 1H); 71% yield.

N-(biphenyl-4-ylcarbamothioyl)-3-fluorobenzamide (JJJ): $^1$H NMR (500 MHz, d6-DMSO): δ 7.36 (m, 1H), 7.49 (m, 2H), 7.52 (m, 1H), 7.6 (m, 1H), 7.74 (m, 4H), 7.83 (m, 4H), 11.7 (s, 1H), 12.6 (s, 1H); 50% yield.

N-(biphenyl-4-ylcarbamothioyl)-4-fluorobenzamide (KKK): $^1$H NMR (500 MHz, d6-DMSO): δ 7.39 (m, 3H), 7.48 (t, J=8 Hz, 2H), 7.71 (m, 4H), 7.82 (d, J=8.5 Hz, 2H), 8.08 (m, 2), 11.7 (1H, s), 12.65 (1H, s); 76% yield.

N-(biphenyl-4-ylcarbamothioyl)-3-methylbenzamide (LLL): $^1$H NMR (500 MHz, d6-acetone): δ 2.44 (s, 3H), 7.38 (m, 1H), 7.48 (td, J=2 Hz, 10 Hz, 3H), 7.52 (d, J=8 Hz, 1H), 7.72 (m, 4H), 7.88 (d, J=8 Hz, 1H), 7.94 (m, 3H), 10.2 (s, 1H), 12.95 (s, 1H); 53% yield.

N-(biphenyl-4-ylcarbamothioyl)-4-methylbenzamide (MMM): $^1$H NMR (400 MHz, d6-DMSO): δ 2.39 (s, 3H), 7.35 (m, 3H), 7.47 (t, J=8 Hz, 2H), 7.7 (m, 4H), 7.8 (d, J=8 Hz, 2H), 7.9 (m, 2H), 11.5 (s, 1H), 12.7 (s, 1H); 29% yield.

N-(biphenyl-4-ylcarbamothioyl)-2-naphthamide (NNN): $^1$H NMR (500 MHz, d6-acetone): δ 7.39 (m, 1H), 7.49 (m, 2H), 7.65-7.78 (m, 6H), 7.97 (m, 2H), 8.05 (dd, J=1 Hz, 8 Hz, 1H), 8.11 (d, J=1.5 Hz, 2H), 8.15 (d, J=8 Hz, 1H), 8.8 (s, 1H), 10.48 (s, 1H), 13.0 (s, 1H); 68% yield.

N-(biphenyl-4-ylcarbamothioyl)-1-naphthamide (OOO): $^1$H NMR (500 MHz, d6-acetone): δ 7.38 (m, 1H), 7.49 (t, J=6 Hz, 2H), 7.66 (m, 3H), 7.73 (m, 2H), 7.77 (d, J=8.5 Hz, 2H), 8.02 (m, 4H), 8.15 (d, J=8 Hz, 1H), 8.4 (d, J=8 Hz, 1H), 10.7 (s, 1H), 12.97 (s, 1H); 67% yield.

N-(biphenyl-4-ylcarbamothioyl)-3-bromobenzamide (PPP): $^1$H NMR (500 MHz, d6-DMSO): δ 7.38 (m, 1H), 7.48 (m, 3H), 7.72 (m, 4H), 7.82 (m, 2H), 7.86 (m, 1H), 7.97 (d, 6.8 Hz, 1H), 8.18 (t, J=1.2 Hz, 1H), 11.8 (1H, s), 12.5 (1H, s); 80% yield.

N-(biphenyl-4-ylcarbamothioyl)-4-bromobenzamide (QQQ): $^1$H NMR (500 MHz, d6-DMSO): δ 7.38 (t, J=7.5 Hz, 1H), 7.48 (t, J=8 Hz, 2H), 7.7 (d, J=7 Hz, 2H), 7.72 (d, J=8.5 Hz, 2H), 7.75 (m, 2H), 7.81 (d, J=7.5 Hz, 2H), 7.92 (d, J=9 Hz, 2H), 11.7 (s, 1H), 12.6 (s, 1H); 72% yield.

N-(biphenyl-4-ylcarbamothioyl)-3-(trifluoromethyl)benzamide (RRR): $^1$H NMR (500 MHz, d6-DMSO): δ 7.39 (t, J=7.5 Hz, 1H), 7.48 (m, 2H), 7.7 (d, J=8 Hz, 2H), 7.75 (d, J=9 Hz, 2H), 7.82 (m, 3H), 8.03 (d, J=8 Hz, 1H), 8.25 (d, J=8 Hz, 1H), 8.35 (s, 1H), 11.96 (s, 1H), 12.5 (s, 1H); 67% yield.

N-(biphenyl-4-ylcarbamothioyl)-4-(trifluoromethyl)benzamide (SSS): $^1$H NMR (500 MHz, d6-DMSO): δ 7.38 (m, 1H), 7.47 (t, J=8 Hz, 2H), 7.7 (d, J=7.5 Hz, 2H), 7.73 (d, J=8.5 Hz, 2H), 7.82 (d, J=8.5 Hz, 2H), 7.92 (d, J=8 Hz, 2H), 8.15 (d, J=8.5 Hz, 2H), 11.9 (s, 1H), 12.5 (s, 1H); 75% yield.

N-(biphenyl-4-ylcarbamothioyl)-3-cyanobenzamide (TTT): $^1$H NMR (500 MHz, d6-DMSO): δ 7.37 (m, 2H), 7.48 (t, J=8 Hz, 2H), 7.74 (m, 4H), 7.81 (d, J=8.5 Hz, 2H), 8.12 (dt, J=1.5 Hz, 7.5 Hz, 1H), 8.24 (d, J=8 Hz, 1H), 8.45 (s, 1H), 11.85 (s, 1H), 12.5 (s, 1H); 51% yield.

N-(biphenyl-4-ylcarbamothioyl)-4-cyanobenzamide (UUU): $^1$H NMR (500 MHz, d6-DMSO): δ 7.37 (t, J=7.5 Hz, 1H), 7.47 (t, J=8 Hz, 2H), 7.7 (d, J=7.5 Hz, 2H), 7.73 (d, J=8.5 Hz, 2H), 7.81 (d, J=8.5 Hz, 2H), 8.03 (m, 2H), 8.1 (d, J=8 Hz, 2H), 11.9 (s, 1H), 12.5 (s, 1H); 77% yield.

N-(biphenyl-4-ylcarbamothioyl)-3-nitrobenzamide (VVV): $^1$H NMR (500 MHz, d6-DMSO): δ 7.36 (t, J=7.5 Hz, 1H), 7.48 (t, J=7.5 Hz, 2H), 7.7 (m, 4H), 7.82 (m, 3H), 8.37 (d, J=8 Hz, 1H), 8.47 (dd, J=2 Hz, 8 Hz, 1H), 8.8 (s, 1H), 12.0 (s, 1H), 12.5 (s, 1H); quantitative yield.

N-(biphenyl-4-ylcarbamothioyl)-4-nitrobenzamide (WWW): $^1$H NMR (500 MHz, d6-DMSO): δ 7.39 (t, J=7.5 Hz, 1H), 7.49 (t, J=7.5 Hz, 2H), 7.7 (m, 2H), 7.73 (d, J=9 Hz, 2H), 7.82 (d, J=8.5 Hz, 2H), 8.18 (d, J=8.5 Hz, 2H), 8.35 (dd, J=2 Hz, 6.5 Hz, 2H), 12.0 (s, 1H), 12.5 (s, 1H); quantitative yield.

N-(biphenyl-3-ylcarbamothioyl)-3,4-dichlorobenzamide (XXX): $^1$H NMR (500 MHz, d6-DMSO): δ 7.4 (m, 1H), 7.52 (m, 3H), 7.59 (d, J=7.5 Hz, 1H), 7.65 (dd, J=1 Hz, 8 Hz, 1H), 7.68 (d, J=7 Hz, 2H), 7.84 (m, 1H), 7.93 (dd, J=2.5 Hz, 8.5 Hz, 1H), 8.05 (s, 1H), 8.26 (m, 1H), 11.85 (s, 1H), 12.5 (s, 1H); 20% yield.

N-(biphenyl-3-ylcarbamothioyl)-4-chlorobenzamide (YYY): $^1$H NMR (500 MHz, d6-acetone): δ 7.4 (m, 1H), 7.5 (m, 2H), 7.54 (d, J=8 Hz, 1H), 7.59 (dt, J=1.5 Hz, 7.5 Hz, 1H), 7.65 (m, 2H), 7.71 (m, 2H), 7.75 (m, 1H), 8.13 (m, 2H), 8.2 (dt, J=2 Hz, 7.5 Hz, 1H), 10.4 (s, 1H), 12.8 (s, 1H); 78% yield.

N-(biphenyl-3-ylcarbamothioyl)-3-methylbenzamide (ZZZ): $^1$H NMR (500 MHz, d6-acetone): δ 2.45 (s, 3H), 7.4 (m, 1H), 7.52 (m, 5H), 7.59 (dt, J=1.5 Hz, 8 Hz, 1H), 7.72 (m, 2H), 7.76 (m, 1H), 7.89 (d, J=8 Hz, 1H), 7.93 (s, 1H), 8.21 (dt, J=2 Hz, 7 Hz, 1H), 10.2 (s, 1H), 12.95 (s, 1H); 41% yield.

N-(biphenyl-3-ylcarbamothioyl)-4-methylbenzamide (AAAA): $^1$H NMR (500 MHz, d6-acetone): δ 2.45 (s, 3H), 7.4 (m, 3H), 7.5 (m, 2H), 7.54 (d, J=8 Hz, 1H), 7.58 (dt, J=1.5 Hz, 8 Hz, 1H), 7.71 (m, 2H), 7.75 (m, 1H), 8.01 (d, J=8 Hz, 2H), 8.21 (m, 1H), 10.2 (s, 1H), 13.0 (s, 1H); 30% yield.

N-(biphenyl-3-ylcarbamothioyl)-3-nitrobenzamide (BBBB): $^1$H NMR (500 MHz, d6-DMSO): δ 7.4 (m, 1H), 7.5 (m, 4H), 7.68 (m, 3H), 7.84 (t, J=8 Hz, 1H), 8.06 (s, 1H), 8.38 (d, J=8 Hz, 1H), 8.48 (m, 1H), 8.8 (t, J=2 Hz, 1H), 12.1 (s, 1H), 12.5 (s, 1H); 82% yield.

N-(biphenyl-3-ylcarbamothioyl)-4-nitrobenzamide (CCCC): $^1$H NMR (500 MHz, d6-DMSO): δ 7.4 (t, J=7.5 Hz, 1H), 7.52 (m, 3H), 7.58 (d, J=7.5 Hz, 1H), 7.67 (t, J=7.5 Hz, 3H), 8.06 (s, 1H), 8.19 (d, J=8.5 Hz, 2H), 8.35 (dd, J=2 Hz, 7 Hz, 1H), 12.02 (s, 1H), 12.5 (s, 1H); 80% yield.

N-(biphenyl-3-ylcarbamothioyl)-3-fluorobenzamide (DDDD): $^1$H NMR (500 MHz, d6-DMSO): δ 7.4 (m, 1H), 7.52 (m, 4H), 7.6 (m, 2H), 7.68 (m, 3H), 7.85 (m, 2H), 8.05 (s, 1H), 11.7 (s, 1H), 12.6 (s, 1H); HRMS m/z for $C_{20}H_{15}FN_2OS$ predicted 350.0889. found 350.0890; 77% yield.

N-(biphenyl-3-ylcarbamothioyl)-4-fluorobenzamide (EEEE): $^1$H NMR (500 MHz, d6-DMSO): δ 7.4 (m, 3H), 7.5 (m, 4H), 7.58 (d, J=7.5 Hz, 1H), 7.68 (m, 2H), 8.08 (m, 3H), 11.7 (s, 1H), 12.6 (s, 1H); HRMS m/z for $C_{20}H_{15}FN_2OS$ predicted 350.0889. found 350.0886; 68% yield.

N-(biphenyl-3-ylcarbamothioyl)-3-cyanobenzamide (FFFF): $^1$H NMR (500 MHz, d6-DMSO): δ 7.4 (m, 1H), 7.52 (m, 3H), 7.58 (d, J=7.5 Hz, 1H), 7.68 (m, 3H), 7.76 (t, J=8 Hz, 1H), 8.05 (s, 1H), 8.13 (dt, J=1.5 Hz, 8 Hz, 1H), 8.24 (d, J=8 Hz, 1H), 8.45 (s, 1H), 11.9 (s, 1H), 12.5 (s, 1H); 65% yield.

N-(biphenyl-3-ylcarbamothioyl)-4-cyanobenzamide (GGGG): $^1$H NMR (500 MHz, d6-DMSO): δ 7.4 (m, 1H), 7.52 (m, 3H), 7.58 (d, J=7.5 Hz, 1H), 7.68 (m, 3H), 8.02 (d, J=8.5 Hz, 2H), 8.05 (s, 1H), 8.1 (d, J=8 Hz, 2H), 11.9 (s, 1H), 12.5 (s, 1H); 68% yield.

N-(biphenyl-3-ylcarbamothioyl)-3-bromobenzamide (HHHH): $^1$H NMR (500 MHz, d6-DMSO): δ 7.4 (m, 1H), 7.52 (m, 4H), 7.58 (d, J=7.5 Hz, 1H), 7.68 (m, 3H), 7.85 (m, 1H), 7.96 (d, J=8 Hz, 1H), 8.06 (s, 1H), 8.18 (s, 1H), 11.8 (s, 1H), 12.6 (s, 1H); 85% yield.

N-(biphenyl-3-ylcarbamothioyl)-4-bromobenzamide (IIII): $^1$H NMR (500 MHz, d6-DMSO): δ 7.4 (m, 1H), 7.5 (m, 3H), 7.57 (d, J=7.5 Hz, 1H), 7.68 (m, 3H), 7.76 (m, 2H), 7.93 (d, J=8.5 Hz, 2H), 8.05 (s, 1H), 11.7 (s, 1H), 12.6 (s, 1H); 69% yield.

N-(biphenyl-3-ylcarbamothioyl)-3-(trifluoromethyl)benzamide (JJJJ): $^1$H NMR (500 MHz, d6-DMSO): δ 7.4 (t, J=7.5 Hz, 1H), 7.52 (m, 3H), 7.58 (d, J=7.5 Hz, 1H), 7.68 (m, 3H), 7.8 (t, J=7.5 Hz, 1H), 8.03 (d, J=8 Hz, 1H), 8.07 (s, 1H), 8.25 (d, J=8 Hz, 1H), 8.35 (s, 1H), 12.0 (s, 1H), 12.6 (s, 1H); 74% yield.

N-(biphenyl-3-ylcarbamothioyl)-4-(trifluoromethyl)benzamide (KKKK): $^1$H NMR (500 MHz, d6-DMSO): δ 7.4 (t, J=7.5 Hz, 1H), 7.52 (m, 3H), 7.59 (d, J=7.5 Hz, 1H), 7.68 (m, 3H), 7.92 (d, J=8.5 Hz, 2H), 8.06 (s, 1H), 8.15 (d, J=8 Hz, 2H), 11.9 (s, 1H), 12.5 (s, 1H); 65% yield.

Representative Procedure for the Coupling of Thioureas to Alkylamines.

N-(2-bromophenylcarbamothioyl)-3-chlorobenzamide (200 mg, 0.54 mmol, 1 equiv) was dissolved in 1 mL of DMF at room temperature. To this, EDCI (123 mg, 0.65 mmol, 1.2 equiv) was added, and the reaction mixture was stirred. After 30 min, histamine (72 mg, 0.65 mmol, 1.2 equiv) was added, and the reaction was stirred overnight at room temperature. A solution of 1:1 ethyl acetate/water (10 mL) was added to the reaction and stirred for 1 h. The organic layer was washed with water (30 mL×2). The aqueous layer was extracted ethyl acetate (50 mL×2), and the combined organic layers were dried over sodium sulfate. The reaction was purified using silica gel chromatography on the Flashmaster II purification system and isolated in 20% yield ($CH_2Cl_2$ to 20% $CH_3OH/CH_2Cl_2$).

The following compounds were prepared by making the appropriate substitutions in the above representative procedure.

(Z/E)-N-(amino(2-bromophenylamino)methylene)benzamide: $^1$H NMR (400 MHz, d6-acetone): δ 2.92 (broad s, 1H), 7.15 (m, 1H), 7.4-7.5 (m, 4H), 7.65 (dd, J=1.6 Hz, 8 Hz, 1H), 7.75 (d, J=8 Hz, 1H), 8.15 (dd, J=1.2 Hz, 8 Hz, 2H), 9.28 (broad s, 2H); MS (nominal) for $C_{14}H_{12}BrN_3O$ predicted 317.1. found 317.1 ($R_f$=0.2 in 9:1 $CH_2Cl_2/CH_3OH$).

(Z/E)-N-((2-(1H-imidazol-4-yl)ethylamino)(biphenyl-2-ylamino)methylene)benzamide (I-7): $^1$H NMR (400 MHz, d6-DMSO, 80° C.): δ 2.71 (t, J=6.8 Hz, 2H), 3.54 (q, J=6.8 Hz, 2H), 6.77 (s, 1H), 7.4 (m, 13H), 8.0 (m, 2H), 11.6 (s, 1H); MS (nominal) for $C_{25}H_{23}N_5O$ predicted 409.2. found 409.0.

(Z/E)-N-((2-(1H-imidazol-4-yl)ethylamino)(2-bromophenylamino)methylene)-3-chlorobenzamide (III-2): $^1$H NMR (400 MHz, d6-DMSO, 80° C.): δ 2.88 (t, J=7.2 Hz, 2H), 3.7 (q, J=6.4 Hz, 2H), 6.85 (s, 1H), 7.24 (m, 1H), 7.5 (m, 5H), 7.72 (d, J=8 Hz, 1H), 7.96 (m, 2H), 11.8 (broad s, 1H); $^{13}$C NMR (125 MHz, $(CD_3)_2CO$): δ 27.4, 42.5, 115.4, 120.9, 128.2, 128.6, 129.0, 129.6, 129.7, 130.3, 131.5, 134.1, 134.3, 135.6, 136.2, 141.9, 159.3, 175.7; MS (nominal) for $C_{19}H_{17}BrClN_5O$ predicted 445.1. found 445.3. $λ_{max}$ (nm): 240, 265 (0.01 N NaOH/$CH_3CH_2OH$ abs.) ($R_f$=0.2-0.4 in 9:1 $CH_2Cl_2/CH_3OH$).

(Z/E)-N-((2-(1H-imidazol-4-yl)ethylamino)(biphenyl-2-ylamino)methylene)-3-chlorobenzamide (I-2): $^1$H NMR (400 MHz, d6-DMSO, 80° C.): δ 2.7 (t, J=6.8 Hz, 2H), 3.53 (q, J=6.8 Hz, 2H), 6.78 (s, 1H), 7.3-7.5 (m, 12H), 7.92 (m, 2H), 11.6 (s, 1H); HRMS m/z for $C_{25}H_{22}ClN_5O$ predicted 444.1587. found 444.1591 ($R_f$=0.2 in 9:1 $CH_2Cl_2/CH_3OH$).

(Z/E)-N-((2-(1H-imidazol-4-yl)ethylamino)(biphenyl-2-ylamino)methylene)-2-chlorobenzamide (I-1): $^1$H NMR (400 MHz, d6-DMSO, 80° C.): δ 2.65 (t, J=6.8 Hz, 2H), 3.44 (q, J=6.8 Hz, 2H), 6.73 (s, 1H), 7.2-7.6 (m, 14H), 11.6 (s, 1H); HRMS M+ for $C_{25}H_{22}ClN_5O$ predicted 443.1513. found 443.1496 ($R_f$=0.3 in 9:1 $CH_2Cl_2/CH_3OH$).

(Z/E)-N-((2-(1H-imidazol-4-yl)ethylamino)(biphenyl-2-ylamino)methylene)-4-chlorobenzamide (III-5): $^1$H NMR (400 MHz, d8-toluene, 65° C.): δ 2.45 (t, J=6 Hz, 2H), 3.5 (s, 2H), 6.14 (s, 1H), 6.78 (s, 1H), 7.0-7.2 (m, 9H), 7.28 (m, 2H), 8.28 (d, J=6 Hz, 2H); HRMS M+ for $C_{25}H_{22}ClN_5O$ predicted 444.1591. found 444.1589 ($R_f$=0.3 in 9:1 $CH_2Cl_2/CH_3OH$).

(E/Z)—N-((2-(1H-imidazol-4-yl)ethylamino)(biphenyl-2-ylamino)methylene)-2-methylbenzamide (I-3): $^1$H NMR (400 MHz, d6-DMSO, 80° C.): δ 2.39 (s, 3H), 2.66 (t, J=6.8 Hz, 2H), 3.45 (q, J=6.8 Hz, 2H), 6.74 (s, 1H), 7.13 (m, 2H), 7.2-7.46 (m, 11H), 7.69 (broad s, 1H), 11.6 (s, 1H); HRMS m/z for $C_{26}H_{25}N_5O$ predicted 424.2137. found 424.2128 ($R_f$=0.3 in 9:1 $CH_2Cl_2/CH_3OH$).

(E/Z)—N-((2-(1H-imidazol-4-yl)ethylamino)(biphenyl-2-ylamino)methylene)-3-methylbenzamide (I-4): $^1$H NMR (400 MHz, d6-DMSO, 80° C.): δ 2.32 (s, 3H), 2.7 (t, J=6.8 Hz, 2H), 3.53 (q, J=6.4 Hz, 2H), 6.77 (s, 1H), 7.22 (m, 2H), 7.3-7.48 (m, 10H), 7.82 (m, 2H), 11.6 (s, 1H); HRMS m/z for $C_{26}H_{25}N_5O$ predicted 424.2137. found 424.2132 ($R_f$=0.3 in 9:1 $CH_2Cl_2/CH_3OH$).

(E/Z)—N-((2-(1H-imidazol-4-yl)ethylamino)(biphenyl-2-ylamino)methylene)-4-methylbenzamide (I-5): $^1$H NMR (400 MHz, d6-DMSO, 80° C.): δ 2.33 (s, 3H), 2.70 (t, J=6.8 Hz, 2H), 3.53 (d, J=4.8 Hz, 2H), 6.78 (s, 1H), 7.15 (d, J=7.6 Hz, 2H), 7.3-7.44 (m, 9H), 7.47 (s, 1H), 7.88 (d, J=6.8 Hz, 2H), 11.5 (broad s, 1H); HRMS M+ for $C_{26}H_{25}N_5O$ predicted 424.2137. found 424.2130 ($R_f$=0.3 in 9:1 $CH_2Cl_2/CH_3OH$).

(IV-33): $^1$H NMR (400 MHz, d8-toluene, 65° C.): δ 2.5 (t, J=5.6 Hz, 2H), 3.6 (m, 2H), 6.1 (s, 1H), 6.74 (s, 1H), 6.9 (m, 1H), 7.05 (m, 5H), 7.2 (d, J=8 Hz, 1H), 8.36 (d, J=8 Hz, 1H), 8.65 (s, 1H); HRMS M+ for $C_{19}H_{18}ClN_5O$ predicted 368.1278. found 368.1267 ($R_f$=0.4 in 9:1 $CH_2Cl_2/CH_3OH$).

(Z/E)-N-((2-(1H-imidazol-4-yl)ethylamino)(4-bromophenylamino)methylene)-3-chlorobenzamide (III-1): $^1$H NMR (400 MHz, d8-toluene, 65° C.): δ 2.48 (t, J=6 Hz, 2H), 3.57 (s, 2H), 6.07 (s, 1H), 6.8 (m, 2H), 7.05 (m, 2H), 7.19 (m, 3H), 8.32 (d, J=6.4 Hz, 1H), 8.6 (s, 1H); HRMS M+ for $C_{19}H_{17}BrClN_5O$ predicted 446.0383. found 446.0386 ($R_f$=0.3 in 9:1 $CH_2Cl_2/CH_3OH$).

(Z/E)-N-((2-(1H-imidazol-4-yl)ethylamino)(3-bromophenylamino)methylene)-3-chlorobenzamide (III-3): $^1$H NMR (400 MHz, d8-toluene, 80° C.): δ 2.46 (m, 2H), 3.56 (m, 2H), 6.04 (s, 1H), 6.75 (m, 1H), 6.88 (s, 1H), 6.95 (m, 3H), 7.02 (t, J=6.8 Hz, 1H), 7.2 (d, J=8 Hz, 1H), 8.32 (m, 1H), 8.59 (s, 1H); HRMS M+ for $C_{19}H_{17}BrClN_5O$ predicted 446.0383. found 446.0381 ($R_f$=0.3 in 9:1 $CH_2Cl_2/CH_3OH$).

(Z/E)-N-((2-(1H-imidazol-4-yl)ethylamino)(o-toluidino)methylene)-3-chlorobenzamide (III-8): $^1$H NMR (400 MHz, d8-toluene, 50° C.): δ 2.1 (s, 3H), 2.5 (t, J=6 Hz, 2H), 3.64 (s, 2H), 6.1 (s, 1H), 6.74 (s, 1H), 7.0 (m, 5H), 7.2 (d, J=7.6 Hz, 1H), 8.4 (d, J=7.2 Hz, 1H), 8.7 (s, 1H); MS (nominal) M+ for $C_{20}H_{20}ClN_5O$ predicted 382.1. found 382.2 ($R_f$=0.3 in 9:1 $CH_2Cl_2/CH_3OH$).

(Z/E)-N-((2-(1H-imidazol-4-yl)ethylamino)(m-toluidino)methylene)-3-chlorobenzamide (III-9): $^1$H NMR (400 MHz, d8-toluene, 50° C.): δ 2.02 (s, 3H), 2.45 (t, J=6 Hz, 2H), 3.55 (s, 2H), 6.02 (s, 1H), 6.7 (m, 2H), 7.0 (m, 4H), 7.13 (d, J=8 Hz, 1H), 8.35 (d, J=8 Hz, 1H), 8.63 (s, 1H); MS (nominal) M+ for $C_{20}H_{20}ClN_5O$ predicted 382.1. found 382.2 ($R_f$=0.3 in 9:1 $CH_2Cl_2/CH_3OH$).

(Z/E)-N-((2-(1H-imidazol-4-yl)ethylamino)(p-toluidino)methylene)-3-chlorobenzamide (III-10): $^1$H NMR (400 MHz, d8-toluene, 65° C.): δ 2.02 (s, 3H), 2.47 (t, J=6 Hz, 2H), 3.56 (s, 2H), 6.05 (s, 1H), 6.72 (s, 1H), 6.8 (d, J=8 Hz, 2H), 6.95 (m, 3H), 7.13 (m, 1H), 8.32 (d, J=7.2 Hz, 1H), 8.6 (s, 1H); HRMS M+ for $C_{20}H_{20}ClN_5O$ predicted 382.1435. found 382.1423 ($R_f$=0.3 in 9:1 $CH_2Cl_2/CH_3OH$).

(Z/E)-N-((2-(1H-imidazol-4-yl)ethylamino)(2-methoxyphenylamino)methylene)-3-chlorobenzamide (III-11): $^1$H NMR (400 MHz, d8-toluene, 80° C.): δ 2.56 (t, J=6 Hz, 2H), 3.32 (s, 3H), 3.61 (m, 2H), 6.2 (s, 1H), 6.55 (d, J=8 Hz, 1H), 6.77 (t, J=7.2 Hz, 1H), 6.83 (s, 1H), 6.9 (t, J=8 Hz, 1H), 7.01 (t, J=8 Hz, 1H), 7.17 (d, J=7.2 Hz, 1H), 7.35 (m, 1H), 8.34 (d, J=8 Hz, 1H), 8.6 (s, 1H); HRMS M+ for $C_{20}H_{20}ClN_5O_2$ predicted 398.1384. found 398.1382 ($R_f$=0.3 in 9:1 $CH_2Cl_2/CH_3OH$).

(Z/E)-N-((2-(1H-imidazol-4-yl)ethylamino)(3-methoxyphenylamino)methylene)-3-chlorobenzamide (III-12): $^1$H NMR (400 MHz, d8-toluene, 65° C.): δ 2.5 (t, J=6 Hz, 2H), 3.36 (s,3H), 3.62 (s, 2H), 6.09 (s, 1H), 6.59 (dd, J=2 Hz, 8 Hz, 1H), 6.68 (s, 1H), 6.8 (s, 1H), 7.0 (m, 3H), 7.2 (d, J=7.6 Hz, 1H), 8.36 (d, J=7.2 Hz, 1H), 8.65 (s, 1H); HRMS M+ for $C_{20}H_{20}ClN_5O_2$ predicted 398.1384. found 398.1392 ($R_f$=0.3 in 9:1 $CH_2Cl_2/CH_3OH$).

(Z/E)-N-((2-(1H-imidazol-4-yl)ethylamino)(4-methoxyphenylamino)methylene)-3-chlorobenzamide (III-13): $^1$H NMR (400 MHz, d8-toluene, 65° C.): δ 2.55 (m, 2H), 3.34 (s, 3H), 3.64 (s, 2H), 6.12 (s, 1H), 6.64 (d, J=8 Hz, 2H), 6.78 (s, 1H), 6.9 (s, 1H), 7.0 (m, 2H), 7.2 (d, J=8 Hz, 1H), 8.4 (d, J=7.2 Hz, 1H), 8.68 (s, 1H); HRMS M+ for $C_{20}H_{20}ClN_5O_2$ predicted 398.1384. found 398.1382 ($R_f$=0.3 in 9:1 $CH_2Cl_2/CH_3OH$).

(Z/E)-N-((2-(1H-imidazol-4-yl)ethylamino)(2-fluorophenylamino)methylene)-3-chlorobenzamide (III-14): $^1$H NMR (400 MHz, d8-toluene, 65° C.): δ 2.5 (m, 2H), 3.56 (s, 2H), 6.09 (s, 1H), 6.8 (m, 4H), 7.0 (m, 2H), 7.18 (d, J=8 Hz, 1H), 8.29 (s, 1H), 8.57 (s, 1H); HRMS M+ for $C_{19}H_{17}ClFN_5O$ predicted 386.1184. found 386.1187 ($R_f$=0.3 in 9:1 $CH_2Cl_2/CH_3OH$).

(Z/E)-N-((2-(1H-imidazol-4-yl)ethylamino)(3-fluorophenylamino)methylene)-3-chlorobenzamide (III-15): $^1$H NMR (400 MHz, d6-DMSO, 80° C.): δ 2.88 (t, J=6.8 Hz, 2H), 3.72 (d, J=3.6 Hz, 2H), 6.89 (s, 1H), 6.98 (t, J=4.4 Hz, 1H), 7.25 (d, J=7.6 Hz, 1H), 7.34-7.46 (m, 3H), 7.5 (m, 1H), 7.54 (s, 1H), 7.95 (d, J=7.6 Hz, 1H), 8.01 (s, 1H), 11.7 (s, 1H); HRMS M+ for $C_{19}H_{17}ClFN_5O$ predicted 386.1184. found 386.1177 ($R_f$=0.3 in 9:1 $CH_2Cl_2/CH_3OH$).

(Z/E)-N-((2-(1H-imidazol-4-yl)ethylamino)(4-fluorophenylamino)methylene)-3-chlorobenzamide (III-16): $^1$H NMR (400 MHz, DMSO, 80° C.): δ 2.86 (t, J=6.8 Hz, 2H), 3.7 (q, J=6.8 Hz, 2H), 6.87 (s, 1H), 7.2 (m, 2H), 7.42 (t, J=8 Hz, 3H), 7.5 (m, 1H), 7.52 (s, 1H), 7.95 (d, J=7.2 Hz, 1H), 7.99 (s, 1H), 11.67 (s, 1H); HRMS M+ for $C_{19}H_{17}ClFN_5O$ predicted 386.1184. found 386.1189 ($R_f$=0.3 in 9:1 $CH_2Cl_2/CH_3OH$).

(Z/E)-N-((2-(1H-imidazol-4-yl)ethylamino)(2-chlorophenylamino)methylene)-3-chlorobenzamide (III-17): $^1$H NMR (400 MHz, d6-DMSO, 80° C.): δ 2.87 (t, J=6.8 Hz, 2H), 3.69 (m, 2H), 6.85 (s, 1H), 7.28-7.52 (m, 6H), 7.56 (d, J=7.6 Hz, 1H), 7.96 (broad s, 2H), 11.7 (s, 1H); HRMS m/z for $C_{19}H_{17}Cl_2N_5O$ predicted 402.0888. found 402.0891 ($R_f$=0.3 in 9:1 $CH_2Cl_2/CH_3OH$).

(Z/E)-N-((2-(1H-imidazol-4-yl)ethylamino)(3-chlorophenylamino)methylene)-3-chlorobenzamide (III-18): $^1$H NMR (400 MHz, d6-DMSO, 80° C.): δ 2.89 (t, J=6.8 Hz, 2H), 3.72 (q, J=6.4 Hz, 2H), 6.89 (s, 1H), 7.2 (m, 1H), 7.4 (m, 3H), 7.5 (m, 1H), 7.54 (s, 1H), 7.66 (s, 1H), 7.95 (d, J=7.6 Hz, 1H), 8.0 (s, 1H), 11.7 (s, 1H); HRMS M+ for predicted 402.0888. found 402.0880 ($R_f$=0.3 in 9:1 $CH_2Cl_2/CH_3OH$).

(Z/E)-N-((2-(1H-imidazol-4-yl)ethylamino)(4-chlorophenylamino)methylene)-3-chlorobenzamide (III-19): $^1$H NMR (400 MHz, d6-DMSO, 80° C.): δ 2.88 (t, J=6.8 Hz, 2H), 3.7 (m, 2H), 6.88 (s, 1H), 7.4-7.52 (m, 6H), 7.54 (s, 1H), 7.95 (d, J=7.6 Hz, 1H), 7.99 (s, 1H), 11.7 (s, 1H); MS (nominal) for $C_{19}H_{17}Cl_2N_5O$ predicted 402.1. found 402.1 ($R_f$=0.3 in 9:1 $CH_2Cl_2/CH_3OH$).

(Z/E)-N-((2-(1H-imidazol-5-yl)ethylamino)(4-(methylsulfonyl)phenylamino)methylene)-3-chlorobenzamide (III-36): $^1$H-NMR (400 MHz, $d_6$-DMSO, 80° C.) δ 2.89 (t, J=6.8 Hz, 2H), 3.17 (s, 3H), 3.74 (m, 2H), 6.89 (s, 1H), 7.43 (t, J=7.8 Hz, 1H), 7.51 (dq, J=7.8, 1.2 Hz, 1H), 7.56 (s, 1H), 7.73 (br m, 2H), 7.89 (d, J=8.4 Hz, 2H), 7.94-7.98 (m, 2H).

(Z/E)-N-((2-(1H-imidazol-5-yl)ethylamino)(3-(methylsulfonyl)phenylamino)methylene)-3-chlorobenzamide (III-37): $^1$H-NMR (400 MHz, $d_6$-DMSO, 80° C.) δ 2.89 (t, J=6.8 Hz, 2H), 3.18 (s, 1H), 3.73 (m, 2H), 6.90 (s, 1H), 7.39 (t, J=7.8 Hz, 1H), 7.49 (dq, J=7.8, 1.2 Hz, 1H), 7.55 (s, 1H), 7.62 (t, J=7.8 Hz, 1H), 7.68 (d, J=7.6 Hz, 1H), 7.79 (m, 1H), 7.97 (m, 2H), 8.16 (br s, 1H).

(Z/E)-N-((2-(1H-imidazol-5-yl)ethylamino)(2-(methylsulfonyl)phenylamino)methylene)-3-chlorobenzamide (III-38): $^1$H-NMR (400 MHz, $d_6$-DMSO, 80° C.) δ 2.88 (t, J=7.0, 2H), 3.21 (s, 3H), 3.68 (m, 2H), 6.85 (s, 1H), 7.41-7.53 (m, 5H), 7.67 (m, 2H), 7.93-7.95 (m, 2H).

(Z/E)-N-((2-(1H-imidazol-5-yl)ethylamino)(4-(N,N-dimethylsulfamoyl)phenylamino)methylene)-3-chlorobenzamide (III-39): $^1$H-NMR (400 MHz, d$_6$-DMSO, 80° C.): δ 2.67 (s, 6H), 2.91 (t, J=6.6 Hz, 2H), 3.76 (t, J=6.6 Hz, 2H), 6.91 (s, 1H), 7.43 (t J=7.8 Hz, 1H), 7.50 (dq, J=7.8, 1.2 Hz, 1H), 7.58 (s, 1H), 7.31-7.75 (br m, 4H), 7.95-7.99 (m, 2H).

(Z/E)-N-((2-(1H-imidazol-5-yl)ethylamino)(3-(N,N-dimethylsulfamoyl)phenylamino) methylene)-3-chlorobenzamide (III-40): $^1$H-NMR (400 MHz, d$_6$-DMSO, 80° C.): δ 2.67 (s, 6H), 2.90 (t, J=6.8 Hz, 2H), 3.74 (m, 2H), 6.91 (s, 1H), 7.40 (t, J=7.8, 1H), 7.49 (m, 1H), 7.51 (s, 1H), 7.55 (s, 1H), 7.62 (t, J=7.8 Hz, 1H), 7.80-7.82 (m, 1H), 7.95-7.98 (m, 3H), 11.6-11.8 (br s, 1H).

(Z/E)-N-((2-(1H-imidazol-4-yl)ethylamino)(2-(trifluoromethyl)phenylamino)methylene)-3-chlorobenzamide (III-23): $^1$H NMR (500 MHz, ethanol, 50° C.): δ 3.18 (t, J=6.5 Hz, 2H), 4.0 (t, J=6.5 Hz, 2H), 7.1 (s, 1H), 7.5-7.7 (m, 4H), 7.73 (s, 1H), 7.85 (t, J=7.5 Hz, 1H), 7.95 (d, J=7.5 Hz, 1H), 8.4 (m, 2H); HRMS M+ for $C_{20}H_{17}ClF_3N_5O$ predicted 436.1152. found 436.1141 ($R_f$=0.4 in 20% CH$_3$OH/80% CH$_2$Cl$_2$).

(Z/E)-N-((2-(1H-imidazol-4-yl)ethylamino)(3-(trifluoromethyl)phenylamino)methylene)-3-chlorobenzamide (III-24): $^1$H NMR (400 MHz, DMSO, 80° C.): δ 2.9 (t, J=6.8 Hz, 2H), 3.75 (q, J=6.4 Hz, 2H), 6.9 (s, 1H), 7.4 (t, J=8 Hz, 1H), 7.5 (m, 2H), 7.55 (s, 1H), 7.6 (t, J=8 Hz, 1H), 7.72 (d, J=7.6 Hz, 1H), 8.0 (m, 3H), 11.7 (s, 1H); HRMS M+ for $C_{20}H_{17}ClF_3N_5O$ predicted 436.1152. found 436.1153 ($R_f$=0.4 in 20% CH$_3$OH/80% CH$_2$Cl$_2$).

(Z/E)-N-((2-(1H-imidazol-4-yl)ethylamino)(4-(trifluoromethyl)phenylamino)methylene)-3-chlorobenzamide (III-25): $^1$H NMR (400 MHz, DMSO, 80° C.): δ 2.9 (t, J=6.8 Hz, 2H), 3.74 (d, J=5.2 Hz, 2H), 6.9 (s, 1H), 7.43 (t, J=8 Hz, 1H), 7.5 (m, 1H), 7.56 (s, 1H), 7.7 (s, 4H), 7.98 (m, 2H), 11.7 (s, 1H); HRMS m/z for $C_{20}H_{17}ClF_3N_5O$ predicted 435.1074. found 435.1087 ($R_f$=0.4 in 20% CH$_3$OH/80% CH$_2$Cl$_2$).

(Z/E)-N-β2-(1H-imidazol-4-yl)ethylamino)(2-ethylphenylamino)methylene)-3-chlorobenzamide (III-41): δ 2.9 (q, J=7 Hz, 2H), 3.2 (t, J=7 Hz, 2H), 4.05 (t, J=7 Hz, 2H), 7.1 (s, 1H), 7.42 (d, J=7.5 Hz, 1H), 7.54 (m, 2H), 7.6-7.7 (m, 3H), 7.77 (s, 1H), 8.4 (m, 2H), 17.45 (t, J=6 Hz, 3H); HRMS M+ for $C_{21}H_{22}ClN_5O$ predicted 396.1591. found 396.1593 ($R_f$=0.6 in 20% CH$_3$OH/80% CH$_2$Cl$_2$).

(Z/E)-N-β2-(1H-imidazol-4-yl)ethylamino)(3-ethylphenylamino)methylene)-3-chlorobenzamide (III-42): $^1$H NMR (400 MHz, d8-toluene, 50° C.): δ 1.08 (t, J=7.2 Hz, 3H), 2.43 (d, J=7.2 Hz, 2H), 2.5 (t, J=6.4 Hz, 2H), 3.6 (m, 2H), 3.82 (m, 2H), 6.13 (s, 1H), 6.81 (m, 2H), 7.05 (m, 4H), 7.2 (d, J=8 Hz, 1H), 8.1 (d, J=7.2 Hz, 1H), 8.69 (s, 1H); HRMS M+ for $C_{21}H_{22}ClN_5O$ predicted 396.1591. found 396.1589 ($R_f$=0.6 in 20% CH$_3$OH/80% CH$_2$Cl$_2$).

(Z/E)-N-((2-(1H-imidazol-4-yl)ethylamino)(4-ethylphenylamino)methylene)-3-chlorobenzamide (III-43): $^1$H NMR (400 MHz, d8-toluene, 50° C.): δ 1.05 (t, J=7.6 Hz, 3H), 2.4 (q, J=7.6 Hz, 2H), 2.6 (t, J=6.4 Hz, 2H), 3.6 (m, 2H), 6.43 (s, 1H), 6.95 (m, 5H), 7.1 (s, 1H), 7.18 (dd, J=1.2 Hz, 8 Hz, 1H), 8.31 (d, J=8 Hz, 1H), 8.58 (s, 1H); HRMS M+ for $C_{21}H_{22}ClN_5O$ predicted 396.1591. found 396.1591 ($R_f$=0.6 in 20% CH$_3$OH/80% CH$_2$Cl$_2$).

(Z/E)-N-((2-(1H-imidazol-4-yl)ethylamino)(biphenyl-4-ylamino)methylene)-3-chlorobenzamide (III-7): $^1$H NMR (400 MHz, d8-toluene, 80° C.): δ 2.52 (t, J=6 Hz, 2H), 3.65 (s, 2H), 6.04 (s, 1H), 6.6 (s, 1H), 7.1 (m, 4H), 7.2 (m, 4H), 7.45 (m, 3H), 8.37 (d, J=7.6 Hz, 1H), 8.65 (s, 1H); HRMS M+ for $C_{25}H_{22}ClN_5O$ predicted 444.1591. found 444.1594 ($R_f$=0.3 in 9:1 CH$_2$Cl$_2$/CH$_3$OH).

(Z/E)-N-((2-(1H-imidazol-4-yl)ethylamino)(biphenyl-3-ylamino)methylene)-3-chlorobenzamide (III-6): $^1$H NMR (400 MHz, d8-toluene, 80° C.): δ 2.55 (t, J=6 Hz, 2H), 3.65 (m, 2H), 6.1 (s, 1H), 6.76 (s, 1H), 7.05 (m, 2H), 7.13 (d, J=7.2 Hz, 2H), 7.2 (t, J=8 Hz, 3H), 7.35 (d, J=8 Hz, 2H), 7.4 (d, J=8 Hz, 2H), 8.37 (d, J=8 Hz, 1H), 8.65 (s, 1H); HRMS M+ for $C_{25}H_{22}ClN_5O$ predicted 444.1591. found 444.1593.

(Z/E)-N-((2-(1H-imidazol-4-yl)ethylamino)(2,6-diethylphenylamino)methylene)-3-chlorobenzamide (III-44): $^1$H NMR (500 MHz, (CD$_3$)$_2$CO): δ 1.15 (t, J=7.5 Hz, 6H), 2.6 (m, 4H), 2.82 (t, J=6.5 Hz, 2H), 3.78 (q, J=7 Hz, 2H), 6.5 (broad s, 1H), 6.85 (s, 1H), 7.21 (d, J=7.5 Hz, 2H), 7.29 (m, 1H), 7.38 (s, 1H), 7.46 (m, 1H), 7.5 (m, 1H), 8.25 (m, 1H), 8.31 (t, J=1.5 Hz, 1H), 11.8 (broad s, 1H); HRMS M+ for $C_{23}H_{26}ClN_5O$ predicted 424.1904. found 424.1895 ($R_f$=0.65 in 20% CH$_3$OH/80% CH$_2$Cl$_2$); syn (0.7×Bz-423), hydro (0.8×Bz-423), Ramos cell death (2.5×Bz-423).

(Z/E)-N-((2-(1H-imidazol-4-yl)ethylamino)(naphthalen-2-ylamino)methylene)-3-chlorobenzamide (III-26): $^1$H NMR (400 MHz, d8-toluene, 80° C.): δ 2.55 (t, J=6 Hz, 2H), 3.63 (s, 2H), 6.2 (s, 1H), 6.77 (s, 1H), 7.03 (t, J=8 Hz, 1H), 7.1-7.28 (m, 4H), 7.55 (m, 4H), 8.35 (t, J=7.2 Hz, 1H), 8.63 (s, 1H); HRMS M+ for $C_{23}H_{20}ClN_5O$ predicted 418.1432. found 418.1423.

(Z/E)-N-((2-(1H-imidazol-4-yl)ethylamino)(naphthalen-1-ylamino)methylene)-3-chlorobenzamide (III-27): $^1$H NMR (400 MHz, d6-DMSO, 80° C.): δ 2.86 (m, 2H), 3.71 (d, J=5.6 Hz, 2H), 6.8 (s, 1H), 7.44 (m, 2H), 7.5 (d, J=7.2 Hz, 2H), 7.55 (m, 3H), 7.9 (d, J=8 Hz, 2H), 8.0 (m, 3H), 11.6 (s, 1H); HRMS M+ for $C_{23}H_{20}ClN_5O$ predicted 418.1435. found 418.1429.

(Z/E)-N-((2-(1H-imidazol-4-yl)ethylamino)(1H-indol-7-ylamino)methylene)-3-chlorobenzamide (V-4): $^1$H NMR (500 MHz, (CD$_3$)$_2$CO): δ 2.85 (m, 2H), 3.83 (t, J=5.5 Hz, 2H), 6.45 (s, 1H), 6.54 (m, 1H), 7.05 (m, 3H), 7.45 (m, 2H), 7.55 (m, 2H), 8.05 (m, 2H), 12.2 (s, 1H); HRMS M+ for $C_{21}H_{19}ClN_6O$ predicted 407.1387. found 407.1382 ($R_f$=0.4 in 9:1 CH$_2$Cl$_2$/CH$_3$OH).

(Z/E)-N-((2-(1H-imidazol-4-yl)ethylamino)(1H-indol-6-ylamino)methylene)-3-chlorobenzamide (V-3): $^1$H NMR (500 MHz, ethanol, 50° C.): δ 3.2 (t, J=7 Hz, 2H), 7.03 (t, J=7 Hz, 2H), 6.73 (d, J=2.5 Hz, 1H), 7.1 (m, 2H), 7.54 (d, J=3 Hz, 1H), 7.57 (s, 1H), 7.63 (t, J=7.5 Hz, 1H), 7.7 (d, J=7.5 Hz, 1H), 7.75 (s, 1H), 7.84 (d, J=8 Hz, 1H), 8.4 (d, J=7 Hz, 1H), 8.48 (s, 1H); HRMS M+ for $C_{19}H_{18}ClN_5O$ predicted 407.1387. found 407.1386 ($R_f$=0.3 in 9:1 CH$_2$Cl$_2$/CH$_3$OH).

(Z/E)-N-((2-(1H-imidazol-4-yl)ethylamino)(1H-indol-5-ylamino)methylene)-3-chlorobenzamide (V-2): $^1$H NMR (500 MHz, ethanol, 50° C.): δ 3.11 (t, J=7 Hz, 2H), 3.95 (t, J=7 Hz, 2H), 6.65 (d, J=3 Hz, 1H), 7.03 (s, 1H), 7.13 (d, J=6.5 Hz, 1H), 7.47 (d, J=3 Hz, 1H), 7.65 (m, 5H), 8.33 (d, J=6 Hz, 1H), 8.43 (s, 1H); HRMS M+ for $C_{19}H_{18}ClN_5O$ predicted 407.1387. found 407.1392 ($R_f$=0.3 in 9:1 CH$_2$Cl$_2$/CH$_3$OH).

(Z/E)-N-((2-(1H-imidazol-4-yl)ethylamino)(1H-indol-4-ylamino)methylene)-3-chlorobenzamide (V-1): $^1$H NMR (500 MHz, ethanol, 50° C.): δ 3.1 (t, J=7 Hz, 2H), 3.98 (t, J=7 Hz, 2H), 6.6 (d, J=3.5 Hz, 1H), 6.95 (s, 1H), 7.05 (d, J=7.5 Hz, 1H), 7.29 (t, J=8 Hz, 1H), 7.42 (d, J=3.5 Hz, 1H), 7.55 (m, 2H), 7.6 (d, J=8 Hz, 1H), 7.65 (s, 1H), 8.34 (m, 1H), 8.43 (s, 1H); HRMS M+ for predicted 407.1387. found 407.1386 ($R_f$=0.2 in 9:1 CH$_2$Cl$_2$/CH$_3$OH).

(Z/E)-N-((2-(1H-imidazol-4-yl)ethylamino)(2'-methoxybiphenyl-4-ylamino)methylene)-3-chlorobenzamide (III-33): $^1$H NMR (400 MHz, d6-DMSO, 80° C.): δ 2.9 (t, J=6.8 Hz, 2H), 3.75 (q, J=6.8 Hz, 2H), 3.8 (s, 3H), 6.89 (s, 1H), 7.05 (m, 1H), 7.12 (d, J=8 Hz, 1H), 7.24 (m, 2H), 7.43 (t, J=8 Hz, 3H), 7.52 (m, 4H), 8.01 (d, J=7.6 Hz, 1H), 8.06 (s, 1H), 11.7 (s, 1H); HRMS m/z for $C_{26}H_{24}ClN_5O_2$ predicted 473.1618. found 473.1610.

(Z/E)-N-((2-(1H-imidazol-4-yl)ethylamino)(3'-methoxybiphenyl-4-ylamino)methylene)-3-chlorobenzamide (III-34): $^1$H NMR (400 MHz, d6-DMSO, 80° C.): δ 2.9 (t, J=6.8 Hz, 2H), 3.74 (q, J=6.8 Hz, 2H), 3.85 (s, 3H), 6.89 (s, 1H), 6.94 (dd, J=2 Hz, 8 Hz, 1H), 7.2 (t, J=2 Hz, 1H), 7.25 (m, 1H), 7.4 (m, 2H), 7.5 (m, 3H), 7.54 (s, 1H), 7.68 (m, 2H), 8.01 (d, J=7.6 Hz, 1H), 8.05 (s, 1H), 11.7 (s, 1H); HRMS m/z for $C_{26}H_{24}ClN_5O_2$ predicted 473.1618. found 473.1622.

(Z/E)-N-((2-(1H-imidazol-4-yl)ethylamino)(4'-methoxybiphenyl-4-ylamino)methylene)-3-chlorobenzamide (III-35): $^1$H NMR (400 MHz, d6-DMSO, 80° C.): δ 2.9 (t, J=6.8 Hz, 2H), 3.73 (q, J=6.8 Hz, 2H), 3.82 (s, 3H), 6.88 (s, 1H), 7.05 (m, 2H), 7.5 (m, 5H), 7.62 (td, J=2.4 Hz, 6.4 Hz, 4H), 8.01 (d, J=8 Hz, 1H), 8.05 (s, 1H), 11.68 (s, 1H); HRMS M+ for $C_{26}H_{24}ClN_5O_2$ predicted 474.1697. found 474.1696 ($R_f$=0.1-0.4 in 9:1 $CH_2Cl_2/CH_3OH$).

(Z/E)-N-((2-(1H-imidazol-4-yl)ethylamino)(3'-chlorobiphenyl-4-ylamino)methylene)-3-chlorobenzamide (III-28): $^1$H NMR (400 MHz, d6-DMSO, 80° C.): δ 2.89 (t, J=6.4 Hz, 2H), 3.74 (q, J=6.4 Hz, 2H), 6.89 (s, 1H), 7.4-7.56 (m, 7H), 7.65 (m, 1H), 7.71 (m, 3H), 8.01 (d, J=7.6 Hz, 1H), 8.04 (s, 1H), 11.68 (s, 1H); HRMS m/z for $C_{25}H_{21}Cl_2N_5O$ predicted 477.1123. found 477.1124 ($R_f$=0.45 in 9:1 $CH_2Cl_2/CH_3OH$).

(Z/E)-N-((2-(1H-imidazol-4-yl)ethylamino)(4'-chlorobiphenyl-4-ylamino)methylene)-3-chlorobenzamide (III-29): $^1$H NMR (400 MHz, d6-DMSO, 80° C.): δ 2.9 (t, J=6.8 Hz, 2H), 3.74 (q, J=6.8 Hz, 2H), 6.89 (s, 1H), 7.42 (t, J=8 Hz, 1H), 7.52 (m, 6H), 7.7 (m, 4H), 8.0 (m, 2H), 11.7 (s, 1H); HRMS M+ for $C_{25}H_{21}Cl_2N_5O$ predicted 478.1201. found 478.1189 ($R_f$=0.35 in 9:1 $CH_2Cl_2/CH_3OH$).

(Z/E)-N-((2-(1H-imidazol-4-yl)ethylamino)(3'-cyanobiphenyl-4-ylamino)methylene)-3-chlorobenzamide (III-45): $^1$H NMR (400 MHz, d6-DMSO, 80° C.): δ 2.9 (t, J=6.8 Hz, 2H), 3.75 (q, J=6 Hz, 2H), 6.9 (s, 1H), 7.45 (t, J=8 Hz, 1H), 7.5-7.6 (m, 4H), 7.67 (t, J=8 Hz, 2H), 7.78 (m, 3H), 8.01 (m, 3H), 8.12 (s, 1H), 11.7 (s, 1H); HRMS M+ for $C_{26}H_{21}ClN_6O$ predicted 469.1544. found 469.1534 ($R_f$=0.2-0.3 in 9:1 $CH_2Cl_2/CH_3OH$).

(Z/E)-N-((2-(1H-imidazol-4-yl)ethylamino)(4'-cyanobiphenyl-4-ylamino)methylene)-3-chlorobenzamide (III-21): $^1$H NMR (400 MHz, d6-DMSO, 80° C.): δ 2.9 (t, J=6.8 Hz, 2H), 3.75 (s, 2H), 6.9 (s, 1H), 7.42 (t, J=7.6 Hz, 1H), 7.5 (dt, J=1.2 Hz, 8 Hz, 1H), 7.58 (m, 3H), 7.76 (d, J=8.4 Hz, 2H), 7.88 (m, 4H), 8.01 (d, J=7.6 Hz, 1H), 8.05 (s, 1H), 11.7 (s, 1H); HRMS M+ for $C_{26}H_{21}ClN_6O$ predicted 469.1544. found 469.1537 ($R_f$=0.2-0.3 in 9:1 $CH_2Cl_2/CH_3OH$).

(Z/E)-N-((2-(1H-imidazol-4-yl)ethylamino)(3'-methylbiphenyl-4-ylamino)methylene)-3-chlorobenzamide (III-31): $^1$H-NMR (400 MHz, DMSO-$d_6$, 80° C.) δ 2.39 (s, 3H), 2.88 (t, J=6.6 Hz, 2H), 3.73 (m, 2H), 6.88 (br s, 1H), 7.17 (d, J=7.2 Hz, 1H), 7.34 (t, J=7.6 Hz, 1H), 7.40-7.53 (m, 7H), 7.64-7.67 (m, 2H), 8.00 (d, J=7.6, 1H), 8.04 (s, 1H).

(Z/E)-N-((2-(1H-imidazol-4-yl)ethylamino)(4'-methylbiphenyl-4-ylamino)methylene)-3-chlorobenzamide (III-32): $^1$H NMR (400 MHz, d6-DMSO, 80° C.): δ 2.36 (s, 3H), 2.89 (t, J=6.4 Hz, 2H), 3.75 (q, J=6.4 Hz, 2H), 6.89 (s, 1H), 7.28 (d, J=7.6 Hz, 2H), 7.4-7.53 (m, 4H), 7.55 (m, 3H), 7.66 (m, 2H), 8.01 (d, J=7.6 Hz, 1H), 8.05 (s, 1H), 11.7 (s, 1H); HRMS m/z for $C_{26}H_{24}ClN_5O$ predicted 457.1669. found 457.1671 ($R_f$=0.4 in 9:1 $CH_2Cl_2/CH_3OH$).

(Z/E)-N-((2-(1H-imidazol-4-yl)ethylamino)(biphenyl-3-ylamino)methylene)-4-chlorobenzamide (VI-14): $^1$H NMR (400 MHz, d6-DMSO, 80° C.): δ 2.89 (t, J=6.8 Hz, 2H), 3.75 (q, J=6.4 Hz, 2H), 6.87 (s, 1H), 7.36-7.5 (m, 9H), 7.67 (m, 2H), 7.74 (s, 1H), 8.05 (d, J=8 Hz, 2H), 11.66 (s, 1H); HRMS M+ for $C_{25}H_{22}ClN_5O$ predicted 444.1591. found 444.1593.

(Z/E)-N-((2-(1H-imidazol-4-yl)ethylamino)(biphenyl-3-ylamino)methylene)-4-methylbenzamide (VI-1): $^1$H NMR (400 MHz, d6-DMSO, 80° C.): δ 2.32 (s, 3H), 2.9 (t, J=6.8 Hz, 2H), 3.75 (q, J=6.8 Hz, 2H), 6.87 (s, 1H), 7.15 (d, J=8 Hz, 2H), 7.36-7.5 (m, 7H), 7.67 (m, 2H), 7.78 (s, 1H), 7.98 (d, J=7.6 Hz, 2H), 11.66 (s, 1H); HRMS M+ for $C_{26}H_{25}N_5O$ predicted 424.2137. found 424.2132.

(Z/E)-N-((2-(1H-imidazol-4-yl)ethylamino)(biphenyl-3-ylamino)methylene)-3-methylbenzamide (VI-2): $^1$H NMR (400 MHz, d6-DMSO, 80° C.): δ 2.2 (s, 3H), 2.85 (t, J=6.8 Hz, 2H), 3.68 (q, J=6.4 Hz, 2H), 6.82 (s, 1H), 7.19 (m, 2H), 7.3-7.45 (m, 7H), 7.63 (m, 2H), 7.8 (m, 3H), 11.6 (s, 1H); HRMS M+ for $C_{26}H_{25}N_5O$ predicted 424.2137. found 424.2127.

(Z/E)-N-((2-(1H-imidazol-4-yl)ethylamino)(biphenyl-3-ylamino)methylene)-3-(trifluoromethyl)benzamide (VI-3): $^1$H NMR (400 MHz, d8-toluene, 80° C.): δ 2.55 (t, J=6 Hz, 2H), 3.65 (s, 2H), 6.16 (s, 1H), 6.7 (s, 1H), 7.05-7.25 (m, 7H), 7.45 (m, 4H), 8.58 (d, J=7.6 Hz, 1H), 8.92 (s, 1H); HRMS m/z for $C_{26}H_{22}F_3N_5O$ predicted 477.1776. found 477.1779.

(Z/E)-N-((2-(1H-imidazol-4-yl)ethylamino)(biphenyl-3-ylamino)methylene)-4-(trifluoromethyl)benzamide (VI-4): $^1$H NMR (400 MHz, d6-DMSO, 80° C.): δ 2.9 (t, J=6.4 Hz, 2H), 3.75 (m, 2H), 6.89 (s, 1H), 7.36-7.52 (m, 7H), 7.7 (m, 5H), 8.23 (d, J=7.6 Hz, 2H), 11.7 (s, 1H); HRMS m/z for $C_{26}H_{22}F_3N_5O$ predicted 477.1776. found 477.1784.

(Z/E)-N-((2-(1H-imidazol-4-yl)ethylamino)(biphenyl-3-ylamino)methylene)-3-cyanobenzamide (VI-5): $^1$H NMR (400 MHz, d6-DMSO, 80° C.): δ 2.9 (t, J=6.4 Hz, 2H), 3.75 (q, J=6.4 Hz, 2H), 6.88 (s, 1H), 7.38-7.52 (m, 7H), 7.6 (t, J=8 Hz, 1H), 7.67 (m, 2H), 7.72 (s, 1H), 7.88 (d, J=8 Hz, 1H), 8.35 (m, 2H), 11.67 (s, 1H); HRMS m/z for $C_{26}H_{22}N_6O$ predicted 434.1855. found 434.1855.

(Z/E)-N-((2-(1H-imidazol-4-yl)ethylamino)(biphenyl-3-ylamino)methylene)-4-cyanobenzamide (VI-6): $^1$H NMR (400 MHz, d6-DMSO, 80° C.): δ 2.89 (t, J=6.8 Hz, 2H), 3.75 (q, J=6.8 Hz, 2H), 6.88 (s, 1H), 7.36-7.49 (m, 7H), 7.67 (m, 2H), 7.73 (s, 1H), 7.79 (d, J=8 Hz, 2H), 8.19 (d, J=8 Hz, 2H), 11.68 (s, 1H); HRMS m/z for $C_{26}H_{22}N_6O$ predicted 434.1855. found 434.1855.

(Z/E)-N-((2-(1H-imidazol-4-yl)ethylamino)(biphenyl-3-ylamino)methylene)-3-fluorobenzamide (VI-7): $^1$H NMR (400 MHz, d6-DMSO, 80° C.): δ 2.9 (t, J=6.8 Hz, 2H), 3.75 (q, J=6.8 Hz, 2H), 6.88 (s, 1H), 7.25 (td, J=2.8 Hz, 8 Hz, 1H), 7.4-7.5 (m, 8H), 7.67 (m, 2H), 7.75 (m, 2H), 7.9 (d, J=7.6 Hz, 1H), 11.67 (s, 1H); HRMS m/z for $C_{25}H_{22}FN_5O$ predicted 427.1808. found 427.1807 ($R_f$=0.45 in 9:1 $CH_2Cl_2/CH_3OH$).

(Z/E)-N-((2-(1H-imidazol-4-yl)ethylamino)(biphenyl-3-ylamino)methylene)-4-fluorobenzamide (VI-8): $^1$H NMR (400 MHz, d6-DMSO, 80° C.): δ 2.9 (t, J=6.8 Hz, 2H), 3.75 (q, J=6.8 Hz, 2H), 6.87 (s, 1H), 7.15 (t, J=8.8 Hz, 1H), 7.4 (m, 2H), 7.48 (m, 5H), 7.68 (m, 2H), 7.75 (s, 1H), 8.12 (m, 2H), 11.65 (s, 1H); HRMS m/z for $C_{25}H_{22}FN_5O$ predicted 427.1808. found 427.1820.

(Z/E)-N-((2-(1H-imidazol-4-yl)ethylamino)(biphenyl-3-ylamino)methylene)-3,4-dichlorobenzamide (VI-9): $^1$H NMR (400 MHz, d6-DMSO, 80° C.): δ 2.88 (t, J=6.8 Hz, 2H), 3.74 (q, J=6.8 Hz, 2H), 6.88 (s, 1H), 7.39 (m, 2H), 7.47 (m, 5H), 7.60 (d, J=8.4 Hz, 1H), 7.67 (m, 2H), 7.73 (s, 1H), 7.97 (d, J=7.2 Hz, 1H), 8.16 (s, 1H), 11.68 (s, 1H); HRMS m/z for $C_{25}H_{21}Cl_2N_5O$ predicted 477.1123. found 477.1130 ($R_f$=0.45 in 9:1 $CH_2Cl_2/CH_3OH$).

(Z/E)-N-((2-(1H-imidazol-4-yl)ethylamino)(biphenyl-3-ylamino)methylene)-3-bromobenzamide (VI-10): $^1$H NMR (400 MHz, d6-DMSO, 80° C.): δ 2.9 (t, J=6.8 Hz, 2H), 3.75

(q, J=6.8 Hz, 2H), 6.88 (s, 1H), 7.4 (m, 8H), 7.63 (d, J=8 Hz, 1H), 7.65 (m, 2H), 7.75 (s, 1H), 8.03 (d, J=8 Hz, 1H), 8.18 (s, 1H), 11.67 (s, 1H); HRMS m/z for $C_{25}H_{22}BrN_5O$ predicted 487.1007. found 487.0997.

(Z/E)-N-((2-(1H-imidazol-4-yl)ethylamino)(biphenyl-3-ylamino)methylene)-4-bromobenzamide (VI-11): $^1$H NMR (400 MHz, d6-DMSO, 80° C.): δ 2.9 (t, J=6.8 Hz, 2H), 3.75 (q, J=6.8 Hz, 2H), 6.88 (s, 1H), 7.4 (m, 2H), 7.48 (m, 5H), 7.55 (d, J=8.4 Hz, 2H), 7.67 (d, J=7.6 Hz, 2H), 7.74 (s, 1H), 8.0 (d, J=8.4 Hz, 2H), 11.7 (s, 1H); HRMS m/z for $C_{25}H_{22}BrN_5O$ predicted 487.1007. found 487.0995.

(Z/E)-N-((2-(1H-imidazol-4-yl)ethylamino)(biphenyl-3-ylamino)methylene)-3-nitrobenzamide (VI-12): $^1$H NMR (400 MHz, d8-toluene, 80° C.): δ 2.55 (t, J=6.4 Hz, 2H), 3.67 (s, 2H), 6.14 (s, 1H), 6.66 (s, 1H), 7.0 (t, J=8 Hz, 2H), 7.2 (m, 5H), 7.42 (m, 3H), 7.92 (dd, J=1.2 Hz, 8 Hz, 1H), 8.58 (d, J=8 Hz, 1H), 9.33 (s, 1H); HRMS m/z for $C_{25}H_{22}N_6O_3$ predicted 454.1753. found 454.1751.

(Z/E)-N-((2-(1H-imidazol-4-yl)ethylamino)-(biphenyl-3-ylamino)methylene)-4-nitrobenzamide (VI-13): $^1$H NMR (400 MHz, d6-DMSO, 80° C.): δ 2.7 (m, 2H), 3.75 (q, J=6.8 Hz, 2H), 6.89 (broad s, 1H), 7.4-7.5 (m, 7H), 7.68 (m, 2H), 7.74 (s, 1H), 8.18 (d, J=8.8 Hz, 2H), 8.25 (d, J=8.4 Hz, 2H), 11.67 (s, 1H); HRMS m/z for $C_{25}H_{22}N_6O_3$ predicted 454.1753. found 454.1758.

(Z/E)-N-((2-(1H-imidazol-4-yl)ethylamino)(biphenyl-4-ylamino)methylene)-4-chlorobenzamide (II-1): $^1$H NMR (400 MHz, d6-DMSO, 80° C.): δ 2.9 (t, J=6.8 Hz, 2H), 3.75 (q, J=6.8 Hz, 2H), 6.89 (s, 1H), 7.37 (m, 1H), 7.5 (m, 7H), 7.67 (m, 4H), 8.08 (d, J=8.4 Hz, 2H), 11.7 (s, 1H); HRMS M+ for $C_{25}H_{22}ClN_5O$ predicted 444.1591. found 444.1590 ($R_f$=0.4 in 9:1 $CH_2Cl_2/CH_3OH$).

(Z/E)-N-((2-(1H-imidazol-4-yl)ethylamino)(biphenyl-4-ylamino)methylene)-3-methylbenzamide (II-2): $^1$H NMR (400 MHz, DMSO, 80° C.): δ 2.19 (s, 3H), 2.9 (t, J=6.8 Hz, 2H), 3.75 (t, J=6.8 Hz, 2H), 6.89 (s, 1H), 7.28 (m, 2H), 7.35 (t, J=7.6 Hz, 1H), 7.46-7.56 (m, 5H), 7.69 (d, J=8.4 Hz, 4H), 7.91 (m, 2H), 11.7 (s, 1H); HRMS M+ for $C_{26}H_{25}N_5O$ predicted 424.2137. found 424.2135 ($R_f$=0.4 in 9:1 $CH_2Cl_2/CH_3OH$).

(Z/E)-N-((2-(1H-imidazol-4-yl)ethylamino)(biphenyl-4-ylamino)methylene)-4-methylbenzamide (II-3): $^1$H NMR (400 MHz, d6-DMSO, 80° C.): δ 2.35 (s, 3H), 2.88 (t, J=6.8 Hz, 2H), 3.73 (q, J=6.8 Hz, 2H), 6.88 (s, 1H), 7.2 (d, J=7.6 Hz, 2H), 7.35 (t, J=7.6 Hz, 1H), 7.5 (m, 5H), 7.67 (m, 4H), 7.99 (d, J=7.2 Hz, 2H), 11.69 (s, 1H); HRMS M+ for $C_{26}H_{25}N_5O$ predicted 424.2137. found 424.2121 ($R_f$=0.4 in 9:1 $CH_2Cl_2/CH_3OH$).

(Z/E)-N-((2-(1H-imidazol-4-yl)ethylamino)(biphenyl-4-ylamino)methylene)-3-(trifluoromethyl)benzamide (II-4): $^1$H NMR (400 MHz, d6-DMSO, 80° C.): δ 2.9 (t, J=6.8 Hz, 2H), 3.75 (q, J=6.4 Hz, 2H), 6.89 (s, 1H), 7.36 (t, J=6.8 Hz, 1H), 7.5 (m, 5H), 7.66 (m, 5H), 7.8 (d, J=7.6 Hz, 1H), 8.32 (d, J=7.6 Hz, 1H), 8.37 (s, 1H), 11.7 (s, 1H); HRMS M+ for $C_{26}H_{22}F_3N_5O$ predicted 478.1855. found 478.1852.

(Z/E)-N-((2-(1H-imidazol-4-yl)ethylamino)(biphenyl-4-ylamino)methylene)-4-(trifluoromethyl)benzamide (II-5): $^1$H NMR (400 MHz, d6-DMSO, 80° C.): δ 2.9 (t, J=6.4 Hz, 2H), 3.75 (d, J=4.8 Hz, 2H), 6.9 (s, 1H), 7.38 (m, 1H), 7.5 (m, 5H), 7.7 (m, 4H), 7.75 (d, J=8 Hz, 2H), 8.25 (d, J=8 Hz, 2H), 11.69 (s, 1H); HRMS M+ for predicted 477.1776. found 477.1786.

(Z/E)-N-((2-(1H-imidazol-4-yl)ethylamino)(biphenyl-4-ylamino)methylene)-3-cyanobenzamide (II-6): $^1$H NMR (400 MHz, d6-DMSO, 80° C.): δ 2.9 (t, J=6.8 Hz, 2H), 3.75 (q, J=6.8 Hz, 2H), 6.9 (s, 1H), 7.47 (t, J=7.2 Hz, 1H), 7.5 (m, 5H), 7.63 (d, J=8 Hz, 1H), 7.7 (m, 4H), 7.88 (d, J=7.6 Hz, 1H), 8.36 (m, 2H), 11.7 (s, 1H); HRMS M+ for $C_{26}H_{22}N_6O$ predicted 435.1933. found 435.1930.

(Z/E)-N-((2-(1H-imidazol-4-yl)ethylamino)(biphenyl-4-ylamino)methylene)-4-cyanobenzamide (II-7): $^1$H NMR (400 MHz, d6-DMSO, 80° C.): δ 2.9 (t, J=6.4 Hz, 2H), 3.75 (q, J=6.4 Hz, 2H), 6.9 (s, 1H), 7.38 (m, 1H), 7.7 (m, 5H), 7.7 (d, J=8.4 Hz, 4H), 7.85 (d, J=7.2 Hz, 2H), 8.2 (d, J=8 Hz, 2H), 11.7 (s, 1H); HRMS M+ for $C_{26}H_{22}N_6O$ predicted 434.1855. found 434.1851.

(Z/E)-N-((2-(1H-imidazol-4-yl)ethylamino)(biphenyl-4-ylamino)methylene)-3-fluorobenzamide (II-8): $^1$H NMR (400 MHz, d6-DMSO, 80° C.): δ 2.89 (t, J=6.8 Hz, 2H), 3.74 (q, J=6.4 Hz, 2H), 6.89 (s, 1H), 7.27 (td, J=2.8, 8.8 Hz, 1H), 7.36 (t, J=7.6 Hz, 1H), 7.42-7.54 (m, 6H), 7.59 (m, 4H), 7.76 (d, J=10.4 Hz, 1H), 7.91 (d, J=7.2 Hz, 1H), 11.69 (s, 1H); HRMS M+ for $C_{25}H_{22}FN_5O$ predicted 427.1808. found 427.1811.

(Z/E)-N-((2-(1H-imidazol-4-yl)ethylamino)(biphenyl-4-ylamino)methylene)-4-fluorobenzamide (II-9): $^1$H NMR (400 MHz, d6-DMSO, 80° C.): δ 2.9 (t, J=6.8 Hz, 2H), 3.73 (s, 2H), 6.89 (s, 1H), 7.2 (t, J=8.8 Hz, 2H), 7.35 (t, J=7.2 Hz, 1H), 7.5 (m, 5H), 7.68 (d, J=8.4 Hz, 4H), 8.15 (q, J=6 Hz, 2H), 11.7 (s, 1H); HRMS M+ for $C_{25}H_{22}FN_5O$ predicted 427.1808. found 427.1816.

(Z/E)-N-((2-(1H-imidazol-4-yl)ethylamino)(biphenyl-4-ylamino)methylene)-3,4-dichlorobenzamide (II-16): $^1$H NMR (400 MHz, d6-DMSO, 80° C.): δ 2.89 (t, J=6.8 Hz, 2H), 3.74 (q, J=6 Hz, 2H), 6.89 (s, 1H), 7.36 (td, J=1.2, 7.2 Hz, 1H), 7.45-7.5 (m, 4H), 7.55 (s, 1H), 7.62-7.7 (m, 5H), 8.0 (d, J=8.4 Hz, 1H), 8.19 (s, 1H), 11.7 (s, 1H); HRMS m/z for $C_{25}H_{21}Cl_2N_5O$ predicted 477.1123. found 477.1124 ($R_f$=0.45 in 9:1 $CH_2Cl_2/CH_3OH$).

(Z/E)-N-((2-(1H-imidazol-4-yl)ethylamino)(biphenyl-4-ylamino)methylene)-3-bromobenzamide (II-10): $^1$H NMR (400 MHz, d6-DMSO, 80° C.): δ 2.9 (t, J=6.4 Hz, 2H), 3.74 (q, J=6.4 Hz, 2H), 6.89 (s, 1H), 7.38 (m, 2H), 7.5 (m, 5H), 7.6-7.7 (m, 5H), 8.05 (d, J=7.6 Hz, 1H), 8.21 (s, 1H), 11.7 (s, 1H); HRMS M+ for $C_{25}H_{22}BrN_5O$ predicted 488.1086. found 488.1084.

(Z/E)-N-((2-(1H-imidazol-4-yl)ethylamino)(biphenyl-4-ylamino)methylene)-4-bromobenzamide (II-11): $^1$H NMR (400 MHz, d6-DMSO, 80° C.): δ 2.88 (t, J=6.8 Hz, 2H), 3.75 (q, J=6.4 Hz, 2H), 6.88 (s, 1H), 7.37 (m, 1H), 7.5 (m, 5H), 7.6 (m, 2H), 7.68 (d, J=8.4 Hz, 4H), 8.0 (d, J=8.4 Hz, 2H), 11.7 (s, 1H); HRMS M+ for $C_{25}H_{22}BrN_5O$ predicted 487.1007. found 487.0994.

(Z/E)-N-((2-(1H-imidazol-4-yl)ethylamino)(biphenyl-4-ylamino)methylene)-3-nitrobenzamide (II-12): $^1$H NMR (400 MHz, d6-DMSO, 80° C.): δ 2.9 (t, J=6.4 Hz, 2H), 3.75 (q, J=6.4 Hz, 2H), 6.9 (s, 1H), 7.35 (t, J=7.6 Hz, 1H), 7.5 (m, 5H), 7.7 (m, 5H), 8.3 (d, J=8.4 Hz, 1H), 8.45 (d, J=7.6 Hz, 1H), 8.8 (s, 1H), 11.7 (s, 1H); HRMS m/z for $C_{25}H_{22}N_6O_3$ predicted 454.1753. found 454.1763.

(Z/E)-N-((2-(1H-imidazol-4-yl)ethylamino)(biphenyl-4-ylamino)methylene)-4-nitrobenzamide (II-13): $^1$H NMR (400 MHz, d6-DMSO, 80° C.): δ 2.9 (d, J=7.2 Hz, 2H), 3.75 (q, J=6.4 Hz, 2H), 6.9 (s, 1H), 7.36 (m, 1H), 7.54 (m, 5H), 7.7 (m, 4H), 8.25 (q, J=8.8 Hz, 4H), 11.7 (s, 1H); HRMS m/z for $C_{25}H_{22}N_6O_3$ predicted 454.1753. found 454.1751.

(Z/E)-N-((2-(1H-imidazol-4-yl)ethylamino)(biphenyl-4-ylamino)methylene)-1-naphthamide (II-14): $^1$H NMR (500 MHz, ethanol, 50° C.): δ 3.23 (m, 2H), 4.05 (t, J=7 Hz, 2H), 7.13 (s, 1H), 7.5-7.75 (m, 8H), 7.78 (s, 1H), 7.85 (m, 4H), 8.1 (m, 1H), 8.15 (d, J=8 Hz, 1H), 8.3 (s, 1H), 9.1 (s, 1H); HRMS M+ for $C_{29}H_{25}N_5O$ predicted 460.2137. found 460.2130 ($R_f$=0.5 in 20% $CH_3OH$/80% $CH_2Cl_2$).

(Z/E)-N-((2-(1H-imidazol-4-yl)ethylamino)(biphenyl-4-ylamino)methylene)-2-naphthamide (II-15): $^1$H NMR (500 MHz, d6-acetone): δ 3.0 (broad s, 2H), 3.95 (m, 2H), 7.05 (broad s, 1H), 7.38-8.05 (m, 15H), 8.4 (m, 1H), 8.9 (m, 1H), 12.45 (broad s, 1H); HRMS M+ for $C_{29}H_{25}N_5O$ predicted 460.2137. found 460.2136 ($R_f$=0.55 in 20% $CH_3OH$/80% $CH_2Cl_2$).

(Z/E)-N-((2-(1H-imidazol-4-yl)ethylamino)(biphenyl-4-ylamino)methylene)-2-chloroisonicotinamide (VII-1): $^1$H NMR (500 MHz, d6-acetone): δ 3.02 (t, J=6 Hz, 2H), 4.02 (m, 2H), 7.05 (s, 1H), 7.13 (d, J=8.5 Hz, 1H), 7.4 (t, J=7.5 Hz, 1H), 7.5 (m, 4H), 7.67 (m, 3H), 8.1 (dd, J=2 Hz, J=8.75 Hz, 1H), 8.22 (d, J=7.5 Hz, 1H), 8.26 (d, J=1.5 Hz, 1H), 8.51 (d, J=7.5 Hz, 1H), 10.65 (s, 1H), 11.25 (broad s, 1H), 13.34 (s, 1H); HRMS [M+l]$^+$ for $C_{24}H_{21}ClN_6O$ predicted 445.1544. found 445.1540.

(Z/E)-N-((2-(1H-imidazol-1-yl)ethylamino)(biphenyl-4-ylamino)methylene)-3-chlorobenzamide (IV-2): $^1$H NMR (400 MHz, d6-DMSO, 80° C.): δ 3.82 (q, J=6 Hz, 2H), 7.28 (t, J=6 Hz, 2H), 6.9 (s, 1H), 7.18 (s, 1H), 7.36-7.54 (m, 7H), 7.62 (s, 1H), 7.7 (m, 4H), 8.03 (m, 2H); HRMS m/z for $C_{25}H_{22}ClN_5O$ predicted 443.1513. found 443.1514 ($R_f$=0.7 in 9:1 $CH_2Cl_2/CH_3OH$).

(Z/E)-N-((2-(1H-1,2,4-triazol-3-yl)ethylamino)(biphenyl-4-ylamino)methylene)-3-chlorobenzamide (IV-3): $^1$H NMR (500 MHz, d6-acetone): δ 3.01 (s, 2H), 4.01 (s, 2H), 6.95 (broad s, 1H), 7.47 (m, 6H), 7.67 (m, 5H), 8.27 (m, 2H), 12.2 (broad s, 1H); MS (nominal) M+H+ for $C_{24}H_{21}ClN_6O$ predicted 445.1. found 445.1.

(Z/E)-N-((2-(1H-pyrazol-4-yl)ethylamino)(biphenyl-4-ylamino)methylene)-3-chlorobenzamide (IV-4): $^1$H NMR (400 MHz, d6-DMSO, 80° C.): δ 2.85 (t, J=7.2 Hz, 2H), 3.65 (q, J=6.8 Hz, 2H), 7.34-7.7 (m, 13H), 8.0 (d, J=7.6 Hz, 1H), 8.05 (s, 1H), 12.4 (broad s, 1H); HRMS m/z for $C_{25}H_{22}ClN_5O$ predicted 443.1513. found 443.1504 ($R_f$=0.7 in 9:1 $CH_2Cl_2/CH_3OH$).

(Z/E)-N-((biphenyl-4-ylamino)(2-(2-oxoimidazolidin-1-yl)ethylamino)methylene)-3-chlorobenzamide (IV-7): $^1$H NMR (400 MHz, d6-DMSO, 80° C.): δ 3.24 (t, J=7.8 Hz, 2H), 3.35 (t, J=6 Hz, 2H), 3.45 (t, J=7.8 Hz, 2H), 3.6 (q, J=6 Hz, 2H), 6.13 (s, 1H), 7.35 (t, J=7.2 Hz, 1H), 7.42-7.54 (m, 6H), 7.7 (t, J=7.6 Hz, 4H), 8.05 (d, J=8 Hz, 1H), 8.08 (s, 1H); HRMS m/z for $C_{25}H_{24}ClN_5O_2$ predicted 461.1618. found 461.1610 ($R_f$=0.75 in 10% $CH_3OH$/90% $CH_2Cl_2$).

(R,Z/E)-N-((1-(1H-imidazol-4-yl)propan-2-ylamino)(biphenyl-4-ylamino)methylene)-3-chlorobenzamide (IV-6): $^1$H NMR (400 MHz, d6-DMSO, 80° C.): δ 1.27 (d, J=6.4 Hz, 3H), 2.83 (d, J=6 Hz, 2H), 4.49 (m, 1H), 6.87 (s, 1H), 7.36 (t, J=7.6 Hz, 1H), 7.4-7.54 (m, 7H), 7.69 (m, 4H), 8.01 (d, J=7.6 Hz, 1H), 8.05 (s, 1H), 11.7 (s, 1H); HRMS m/z for $C_{26}H_{24}ClN_5O$ predicted 457.1669. found 457.1686 ($R_f$=0.45 in 9:1 $CH_2Cl_2/CH_3OH$); [α]=+36.9 (c=12.5 mg/1 mL $CHCl_3$).

(S,Z/E)-N-((1-(1H-imidazol-4-yl)propan-2-ylamino)(biphenyl-4-ylamino)methylene)-3-chlorobenzamide (IV-5): $^1$H NMR (400 MHz, d6-DMSO, 80° C.): δ 1.27 (d, J=6.4 Hz, 3H), 2.83 (d, J=6 Hz, 2H), 4.49 (m, 1H), 6.87 (s, 1H), 7.35 (t, J=7.6 Hz, 1H), 7.4-7.54 (m, 7H), 7.69 (m, 4H), 8.01 (d, J=7.6 Hz, 1H), 8.05 (s, 1H), 11.7 (s, 1H); HRMS M+ for $C_{26}H_{24}ClN_5O$ predicted 457.1669. found 457.1680 ($R_f$=0.45 in 9:1 $CH_2Cl_2/CH_3OH$); [α]=−27.6 (c=10.4 mg/1 mL $CHCl_3$).

(Z/E)-N-((1H-indol-4-ylamino)(biphenyl-4-ylamino)methylene)-3-chlorobenzamide (IV-1): $^1$H NMR (400 MHz, d6-DMSO, 80° C.): δ 6.49 (s, 1H), 7.15 (m, 2H), 7.38 (m, 3H), 7.46 (m, 3H), 7.53 (d, J=8 Hz, 1H), 7.6-7.7 (m, 6H), 8.01 (d, J=7.6 Hz, 1H), 8.05 (s, 1H), 9.26 (s, 1H), 11.2 (s, 1H), 11.6 (s, 1H); $^{13}$C NMR (125 MHz, $(CD_3)_2CO$): δ 99.9, 111.4, 116.4, 122.8, 124.7, 124.8, 126.6, 127.4, 127.6, 127.9, 128.3, 128.5, 129.7, 129.9, 130.4, 131.7, 134.3, 137.9, 138.3, 138.5, 141.2, 141.8, 158.3, 176.4; HRMS m/z for $C_{28}H_{21}ClN_4O$ predicted 464.1404. found 464.1408 ($R_f$=0.6 in 50% ethyl acetate/50% hexanes).

(Z/E)-N-((1H-indol-5-ylamino)(biphenyl-4-ylamino)methylene)-3-chlorobenzamide (IV-8): $^1$H NMR (400 MHz, d6-DMSO, 80° C.): δ 6.48 (s, 1H), 7.15 (d, J=8.4 Hz, 1H), 7.35 (m, 2H), 7.45 (m, 4H), 7.52 (d, J=7.6 Hz, 1H), 7.56-7.7 (m, 7H), 8.0 (d, J=7.6 Hz, 1H), 8.04 (s, 1H), 9.37 (s, 1H), 11.02 (s, 1H), 11.13 (s, 1H); HRMS m/z for $C_{28}H_{21}ClN_4O$ predicted 464.1404. found 464.1407 ($R_f$=0.6 in 50% ethyl acetate/50% hexanes).

Example 2

Enantiomerically pure 1-(1H-imidazol-4-yl)propan-2-amine can be prepared using the synthetic scheme show below. See Elz, et al., 1989 Eur. J. Med. Chem. 259-262 and Tet Lett. 30, 1989, 7313 for additional synthetic procedures.

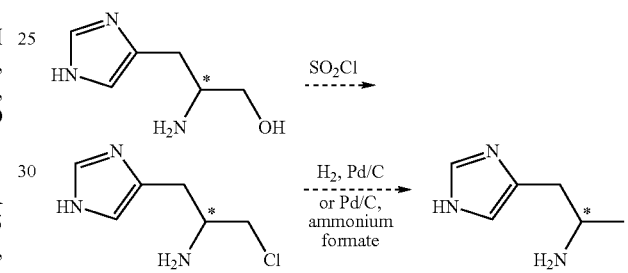

Example 3

The compounds listed in Table 9 were tested for activity against $F_1F_0$-ATPase by measuring ATP synthesis and ATP hydrolysis. In addition, the compounds were assessed for cytotoxicity in Ramos cells Inhibition of ATP synthesis and hydrolysis by the $F_1F_0$-ATPase and cytotoxicity in Ramos cells was measured as described in K. M. Johnson et al. *Chemistry & Biology* 2005, 12, 485-496.

TABLE 9

| Compound | Cell Death (Ramos Cells) ($EC_{50}$ μM) | ATP Synthesis ($IC_{40}$ μM) | ATP Hydrolysis ($IC_{40}$ μM) |
| --- | --- | --- | --- |
| I-1 | >30 | >20 | >30 |
| I-2 | >10 | <10 | <10 |
| I-3 | >30 | >20 | >30 |
| I-4 | >20 | >10 | >20 |
| I-5 | >20 | >10 | >10 |
| I-7 | >30 | >20 | >30 |
| I-8 | >20 | >10 | >10 |
| II-9 | >30 | >20 | >30 |
| II-1 | >30 | >10 | >10 |
| II-2 | >30 | >10 | >10 |
| II-3 | <10 | >10 | >10 |
| II-4 | <10 | >10 | >10 |
| II-5 | <10 | >10 | >10 |
| II-6 | >30 | >20 | >30 |
| II-7 | >30 | >20 | >10 |
| II-8 | <10 | >10 | >10 |
| II-10 | <10 | >10 | >10 |
| II-11 | >30 | >10 | >20 |
| II-12 | >30 | >10 | >10 |

TABLE 9-continued

| Compound | Cell Death (Ramos Cells) (EC$_{50}$ µM) | ATP Synthesis (IC$_{40}$ µM) | ATP Hydrolysis (IC$_{40}$ µM) |
|---|---|---|---|
| II-13 | >30 | >20 | >30 |
| II-16 | <10 | <10 | <10 |
| III-1 | >30 | >20 | >30 |
| III-2 | >20 | <10 | >20 |
| III-3 | >10 | <10 | >10 |
| III-6 | <10 | <10 | >10 |
| III-7 | <10 | <10 | >10 |
| III-8 | >30 | >10 | >30 |
| III-9 | >30 | >10 | >20 |
| III-10 | >10 | >10 | >20 |
| III-11 | >30 | >10 | >30 |
| III-12 | >30 | >20 | >30 |
| III-13 | >30 | >10 | >30 |
| III-14 | >30 | >20 | >30 |
| III-15 | >30 | >20 | >30 |
| III-16 | >30 | >20 | >30 |
| III-17 | >30 | >10 | >20 |
| III-18 | >10 | >10 | >20 |
| III-19 | >10 | >10 | >30 |
| III-20 | >10 | >10 | >10 |
| III-21 | <10 | <10 | >30 |
| III-23 | >20 | >20 | >20 |
| III-24 | >10 | <10 | <10 |
| III-25 | >10 | >10 | <10 |
| III-26 | >10 | >10 | >10 |
| III-27 | >10 | <10 | >10 |
| III-29 | <10 | >10 | >10 |
| III-31 | <10 | >10 | >10 |
| III-34 | <10 | <10 | >10 |
| III-35 | <10 | <10 | >10 |
| III-36 | >30 | >20 | >30 |
| III-37 | >30 | >20 | >30 |
| III-38 | >30 | >20 | >30 |
| III-39 | >30 | >20 | >30 |
| III-40 | >30 | >20 | >30 |
| III-41 | >30 | >10 | >10 |
| III-42 | >20 | <10 | >20 |
| III-43 | >10 | >10 | >20 |
| III-45 | <10 | <10 | >30 |
| IV-1 | >10 | >10 | >30 |
| IV-2 | >10 | <10 | >10 |
| IV-3 | >10 | <10 | <10 |
| IV-4 | <10 | <10 | >10 |
| IV-5 | <10 | <10 | <10 |
| IV-6 | <10 | <10 | <10 |
| IV-7 | >30 | >20 | >30 |
| IV-8 | <10 | >10 | >30 |
| IV-9 | >30 | >20 | >30 |
| V-1 | >30 | >10 | >10 |
| V-2 | >20 | >10 | >20 |
| V-3 | >20 | >10 | <10 |
| V-4 | >30 | >10 | >10 |
| VI-1 | >10 | <10 | >10 |
| VI-2 | >10 | <10 | >10 |
| VI-3 | <10 | <10 | >10 |
| VI-4 | >10 | <10 | >10 |
| VI-5 | >10 | >10 | >30 |
| VI-6 | >10 | <10 | >30 |
| VI-7 | >10 | <10 | >10 |
| VI-8 | >10 | <10 | >10 |
| VI-9 | <10 | <10 | <10 |
| VI-10 | <10 | <10 | >10 |
| VI-11 | <10 | <10 | >10 |
| VI-12 | >10 | <10 | >30 |
| VI-13 | <10 | <10 | >30 |
| VI-14 | >10 | <10 | >10 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by Formula I:

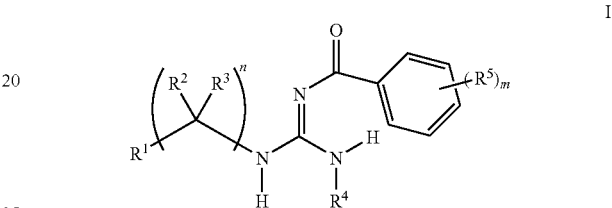

including salts and esters thereof, wherein,

R$^1$ is imidazolidonyl or a heteroaryl containing at least 1 ring nitrogen atom;

R$^2$ and R$^3$ represent independently for each occurrence hydrogen or (C$_1$-C$_4$)alkyl;

R$^4$ is

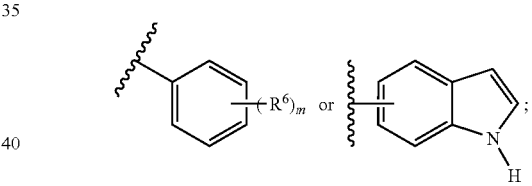

R$^5$ represents independently for each occurrence hydrogen, halogen, alkyl, haloalkyl, aryl, heteroaryl, —NO$_2$, —CN, —C(O)aryl, —C(O)heteroaryl, —C(O)N(R$^2$)aryl, or —C(O)N(R$^2$)heteroaryl;

R$^6$ represents independently for each occurrence hydrogen, halogen, alkyl, haloalkyl, alkoxy, aryl, heteroaryl, —NO$_2$, —CN, —SO$_2$alkyl, or —SO$_2$N(alkyl)$_2$;

n is 0, 1, 2, 3, or 4;

m represents independently for each occurrence 1 or 2; and the stereochemical configuration at a stereocenter in a compound represented by Formula I is R, S, or a mixture thereof.

2. The compound of claim 1, wherein R$^1$ is

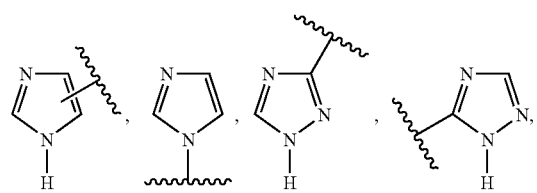

-continued

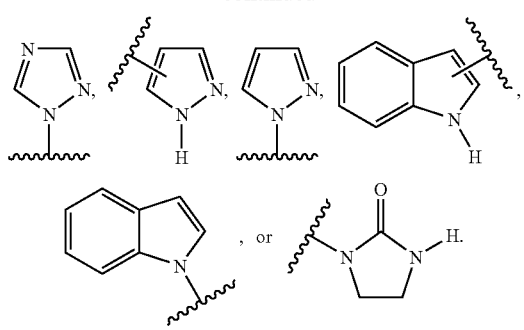

3. The compound of claim 1, wherein $R^1$ is

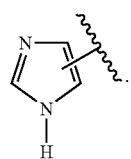

4. The compound of claim 1, wherein n is 2, and $R^2$ and $R^3$ are hydrogen.

5. The compound of claim 1, wherein $R^4$ is

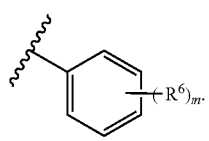

6. The compound of claim 1, wherein $R^6$ is

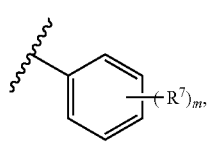

and $R^7$ represents independently for each occurrence hydrogen, halogen, alkyl, alkoxy, or —CN.

7. The compound of claim 1, wherein $R^5$ represents independently for each occurrence halogen, alkyl, haloalkyl, —$NO_2$, or —CN.

8. The compound of claim 1, wherein m is 1.

9. The compound of claim 1, wherein $R^1$ is

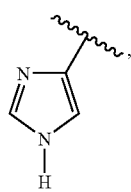

n is 2, $R^2$ and $R^3$ are hydrogen, and $R^4$ is

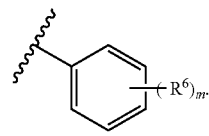

10. The compound of claim 1, wherein $R^1$ is

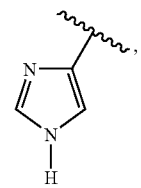

n is 2, $R^2$ and $R^3$ are hydrogen, $R^4$ is

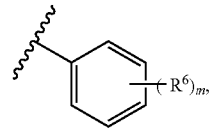

$R^5$ is halogen, alkyl, haloalkyl, —$NO_2$, or —CN, and m is 1.

11. The compound of claim 1, wherein the compound is one of the following:

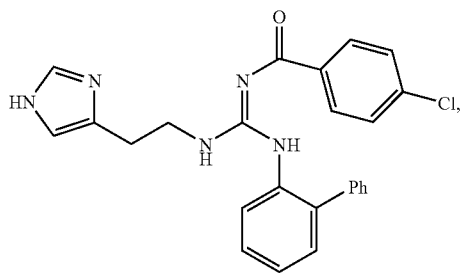

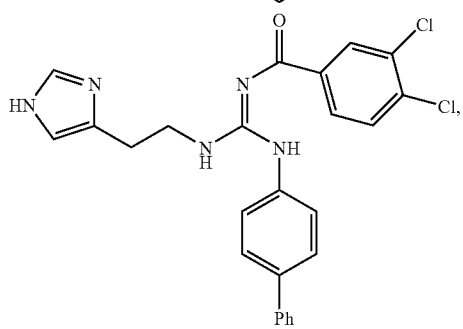

69
-continued
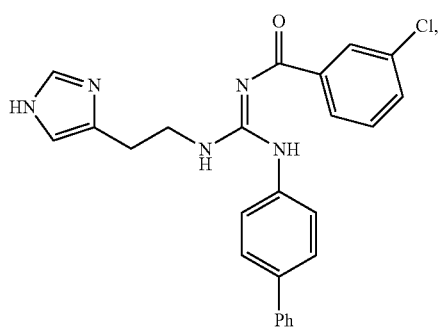
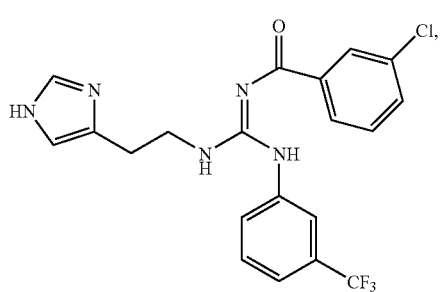
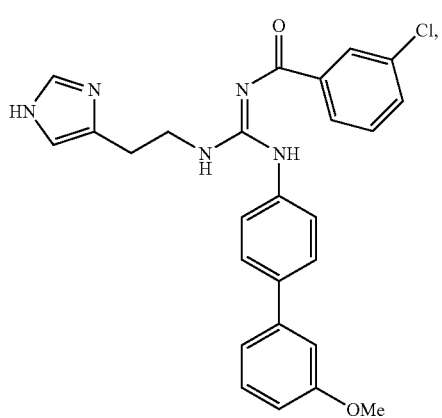
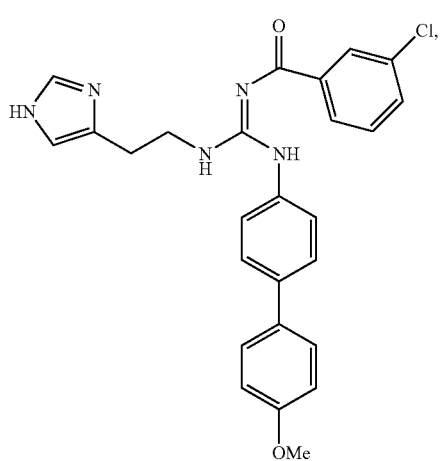
70
-continued
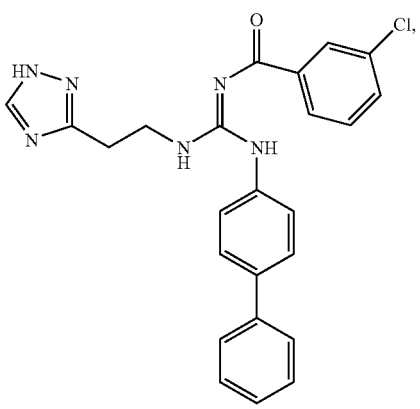

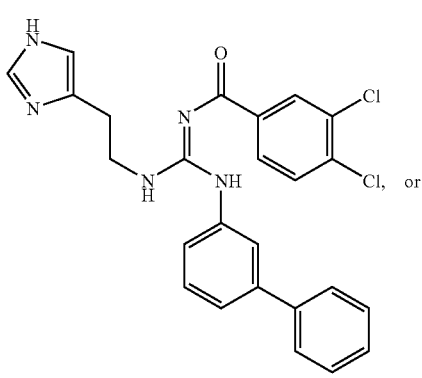

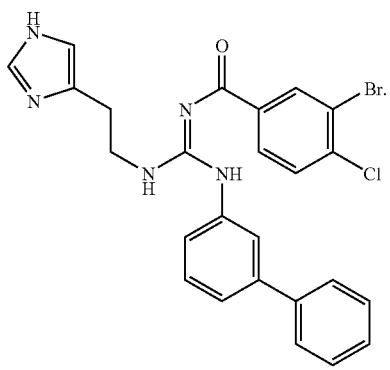

12. A pharmaceutical composition comprising a compound of claim 1 and a pharmaceutically acceptable carrier.

13. The compound of claim 1, wherein the compound has the following formula:

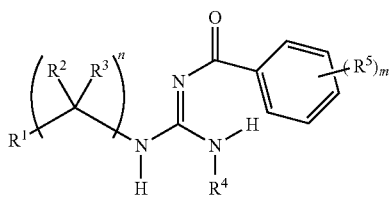

including salts thereof, wherein, $R^1$ is a heteroaryl containing at least 1 ring nitrogen atom;
$R^2$ and $R^3$ represent independently for each occurrence hydrogen or $(C_1-C_4)$alkyl;
$R^4$ is

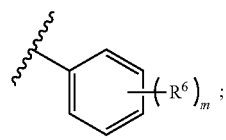

$R^5$ represents independently for each occurrence hydrogen, halogen, alkyl, haloalkyl, aryl, heteroaryl, —$NO_2$, —CN, —C(O)aryl, —C(O)heteroaryl, —C(O)N($R^2$)aryl, or —C(O)N($R^2$)heteroaryl;
$R^6$ represents independently for each occurrence hydrogen, halogen, alkyl, haloalkyl, alkoxy, aryl, heteroaryl, —$NO_2$, —CN, —$SO_2$alkyl, or —$SO_2$N(alkyl)$_2$;
n is 0, 1, 2, 3, or 4;
m represents independently for each occurrence 1 or 2; and
the stereochemical configuration at a stereocenter in a compound represented by said formula is R, S, or a mixture thereof.

14. The compound of claim 13, wherein $R^5$ represents independently for each occurrence halogen, alkyl, or haloalkyl.

15. The compound of claim 14, wherein $R^6$ represents independently for each occurrence halogen, alkyl, or haloalkyl.

* * * * *